(12) United States Patent
Sakamoto et al.

(10) Patent No.: US 10,550,134 B2
(45) Date of Patent: Feb. 4, 2020

(54) HETEROCYCLIC COMPOUND AND ORGANIC ELECTROLUMINESCENCE DEVICE INCLUDING THE SAME

(71) Applicant: SAMSUNG DISPLAY CO., LTD., Yongin-si, Gyeonggi-do (KR)

(72) Inventors: Asami Sakamoto, Yokohama (JP); Hisayuki Kawamura, Yokohama (JP)

(73) Assignee: Samsung Display Co., Ltd., Yongin-si (KR)

( * ) Notice: Subject to any disclaimer, the term of this patent is extended or adjusted under 35 U.S.C. 154(b) by 238 days.

(21) Appl. No.: 15/801,606

(22) Filed: Nov. 2, 2017

(65) Prior Publication Data

US 2018/0134732 A1 May 17, 2018

(30) Foreign Application Priority Data

Nov. 14, 2016 (KR) .......................... 10-2016-0151398

(51) Int. Cl.
*H01L 51/50* (2006.01)
*C07F 7/08* (2006.01)
(Continued)

(52) U.S. Cl.
CPC .......... *C07F 7/0816* (2013.01); *C07D 407/12* (2013.01); *C07D 409/12* (2013.01); *C09K 11/06* (2013.01); *H01L 51/0073* (2013.01); *H01L 51/0074* (2013.01); *H01L 51/0094* (2013.01); *H01L 51/5016* (2013.01); *C09K 2211/1096* (2013.01); *H01L 51/5056* (2013.01)

(58) Field of Classification Search
CPC . C07D 407/12; C07D 409/12; H01L 51/5056; H01L 51/0094; H01L 51/0074; H01L 151/0073; C09K 2211/1096; C09K 11/06; C07F 7/0816
See application file for complete search history.

(56) References Cited

U.S. PATENT DOCUMENTS

2015/0162542 A1* 6/2015 Ryu ..................... H01L 51/0059
257/40
2015/0295181 A1 10/2015 Mujica-Fernaud et al.
2015/0318501 A1 11/2015 Watanabe et al.

FOREIGN PATENT DOCUMENTS

JP 3924799 B2 6/2007
JP 2009-029726 A 2/2009
(Continued)

*Primary Examiner* — Gregory D Clark
(74) *Attorney, Agent, or Firm* — Lewis Roca Rothgerber Christie LLP

(57) ABSTRACT

A heterocyclic compound and an organic electroluminescence device including the same, the heterocyclic compound being represented by Formula 1:

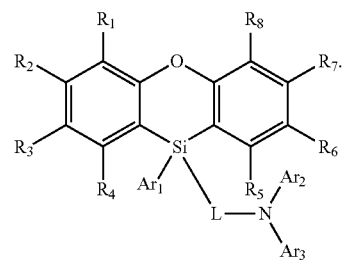

[Formula 1]

20 Claims, 1 Drawing Sheet

(51) Int. Cl.
*C07D 407/12* (2006.01)
*C07D 409/12* (2006.01)
*C09K 11/06* (2006.01)
*H01L 51/00* (2006.01)

(56) References Cited

FOREIGN PATENT DOCUMENTS

| | | | |
|---|---|---|---|
| JP | 2009-267255 A | 11/2009 |
| KR | 10-2014-0025120 A | 3/2014 |
| KR | 10-2015-0079960 A | 7/2015 |
| WO | WO 2014/072017 A1 | 5/2014 |

* cited by examiner

HETEROCYCLIC COMPOUND AND ORGANIC ELECTROLUMINESCENCE DEVICE INCLUDING THE SAME

CROSS-REFERENCE TO RELATED APPLICATION

Korean Patent Application No. 10-2016-0151398, filed on Nov. 14, 2016, in the Korean Intellectual Property Office, and entitled: "Heterocyclic Compound And Organic Electroluminescence Device Including The Same," is incorporated by reference herein in its entirety.

BACKGROUND

1. Field

Embodiments relate to a heterocyclic compound and an organic electroluminescence device including the same.

2. Description of the Related Art

Development of an organic electroluminescence display as an image display is being actively conducted. An organic electroluminescence display is different from a liquid crystal display and is a self-luminescent display that accomplishes display by recombining holes and electrons injected from a first electrode and a second electrode in an emission layer and emitting light from a luminescent material which is an organic compound included in the emission layer.

As an organic electroluminescence device may include, e.g., an organic device composed of a first electrode, a hole transport layer disposed on the first electrode, an emission layer disposed on the hole transport layer, an electron transport layer disposed on the emission layer, and a second electrode disposed on the electron transport layer. Holes are injected from the first electrode, and the injected holes move via the hole transport layer to be injected into the emission layer. Meanwhile, electrons are injected from the second electrode, and the injected electrons move via the electron transport layer to be injected into the emission layer. By recombining the holes and electrons injected into the emission layer, excitons are generated in the emission layer. The organic electroluminescence device emits light using light emitted during the transition of the excitons back to a ground state.

SUMMARY

Embodiments are directed to a heterocyclic compound and an organic electroluminescence device including the same.

The embodiments may be realized by providing a heterocyclic compound represented by the following Formula 1:

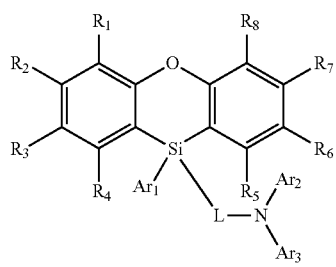

[Formula 1]

wherein, in Formula 1, $R_1$ to $R_8$ are each independently a hydrogen atom, a deuterium atom, a halogen atom, a substituted or unsubstituted silyl group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aryl group having 6 to 30 ring carbon atoms, or a substituted or unsubstituted heteroaryl group having 2 to 30 ring carbon atoms, $R_1$ to $R_8$ being separate or forming a ring by combining adjacent groups with each other, $Ar_1$ to $Ar_3$ are each independently a substituted or unsubstituted aryl group having 6 to 30 ring carbon atoms or a substituted or unsubstituted heteroaryl group having 2 to 30 ring carbon atoms, and L is a direct linkage, a substituted or unsubstituted arylene group having 6 to 30 ring carbon atoms, or a substituted or unsubstituted heteroarylene group having 2 to 30 ring carbon atoms.

$Ar_1$ may be a substituted or unsubstituted aryl group having 6 to 30 ring carbon atoms.

$Ar_1$ may be a substituted or unsubstituted phenyl group or a substituted or unsubstituted biphenyl group.

L may be a group represented by one of the following Formulae L-1 to L-4:

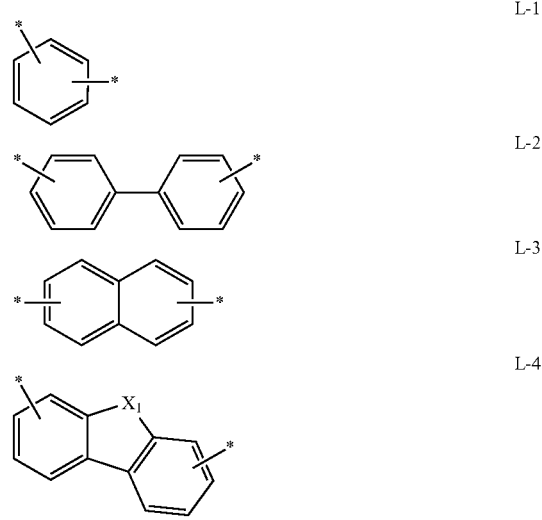

wherein, in Formula L-4, $X_1$ may be O, S, $NR_9$ or $CR_{10}R_{11}$, and $R_9$ to $R_{11}$ may each independently be a hydrogen atom, a deuterium atom, a halogen atom, a substituted or unsubstituted alkyl group having 1 to 30 carbon atoms, a substituted or unsubstituted aryl group having 6 to 30 ring carbon atoms, or a substituted or unsubstituted heteroaryl group having 2 to 30 ring carbon atoms.

At least one of $Ar_2$ or $Ar_3$ may be a substituted or unsubstituted aryl group having 6 to 30 ring carbon atoms.

At least one of $Ar_2$ or $Ar_3$ may be a group represented by the following Formula 2:

*-A-B                    [Formula 2]

wherein, in Formula 2, A may be a substituted or unsubstituted phenylene group, and B may be a substituted or unsubstituted polycyclic aryl group having 6 to 30 ring carbon atoms.

The group represented by Formula 2 is a group represented by the following Formula 2-1:

[Formula 2-1]

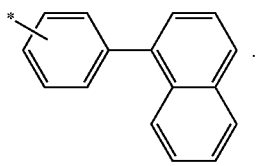

Ar₂ and Ar₃ may be different from each other.

One of Ar₂ and Ar₃ may be a substituted or unsubstituted aryl group having 6 to 30 ring carbon atoms, and the other of Ar₂ and Ar₃ may be a substituted or unsubstituted aryl group having 6 to 30 ring carbon atoms or a group represented by the following Formula 3:

[Formula 3]

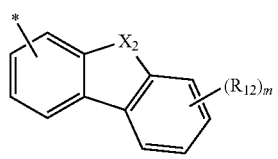

wherein, in Formula 3, $X_2$ may be O or S, m may be an integer of 1 to 4, and $R_{12}$ may be a hydrogen atom, a deuterium atom, or a substituted or unsubstituted aryl group having 6 to 30 ring carbon atoms.

In Formula 3, m may be 0 or 1, and when m is 1, $R_{12}$ may be a substituted or unsubstituted aryl group having 6 to 30 ring carbon atoms.

The heterocyclic compound represented by Formula 1 may be a compound the following Compound Group 1:

[Compound Group 1]

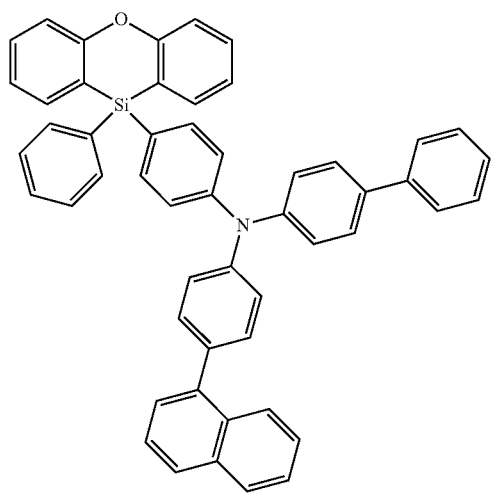

1

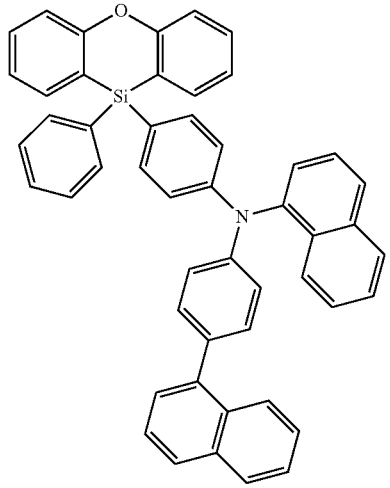

2

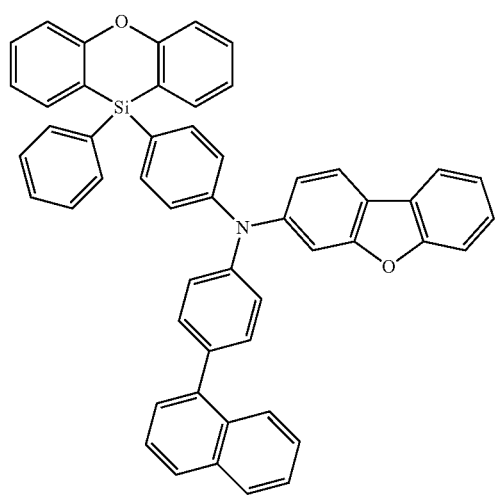

3

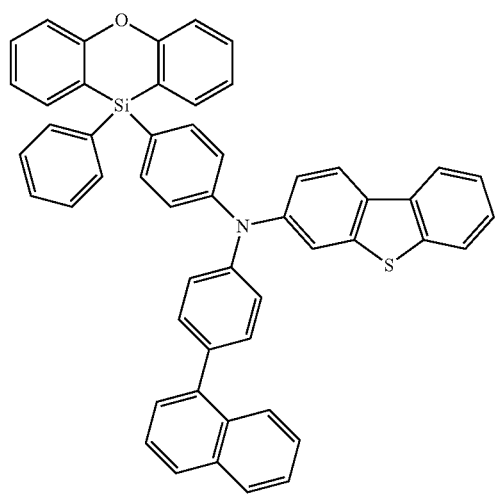

4

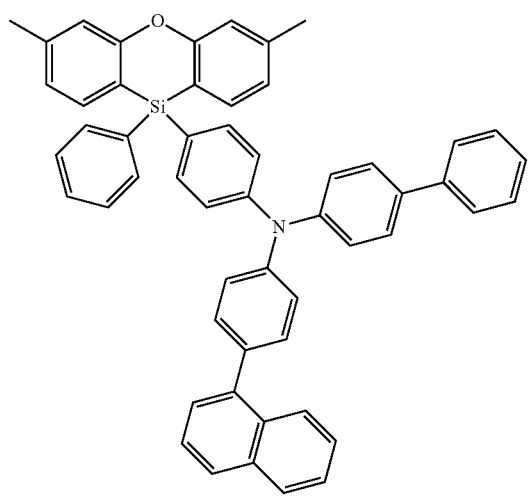
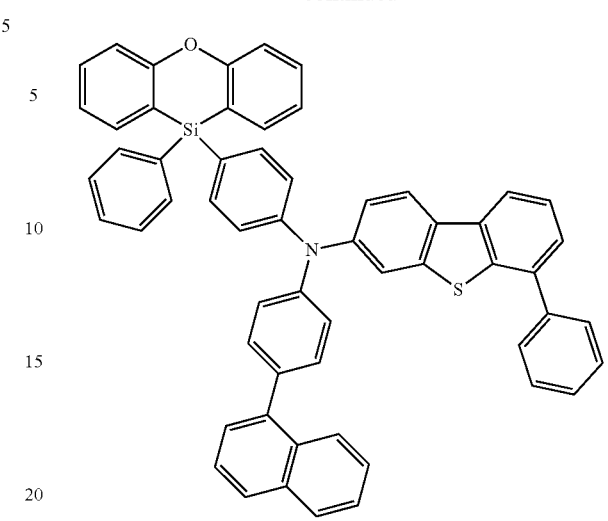

11
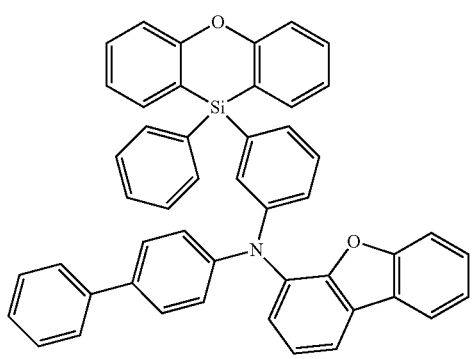
12
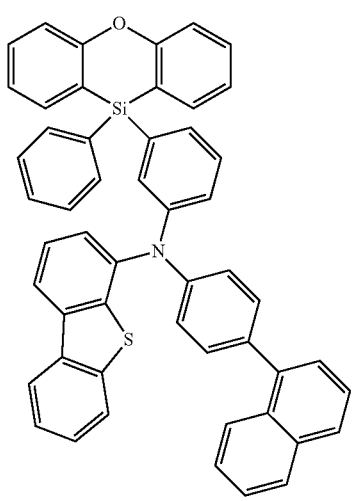
13
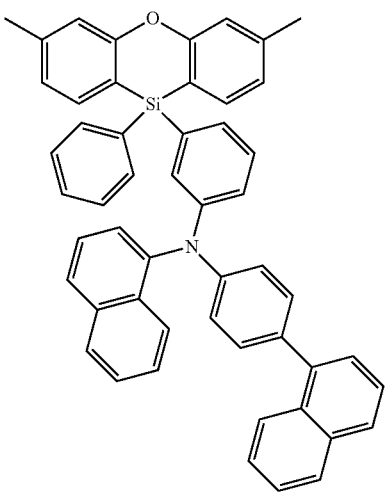
14
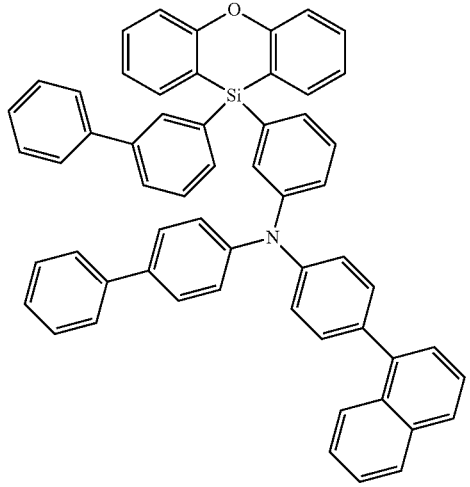
15
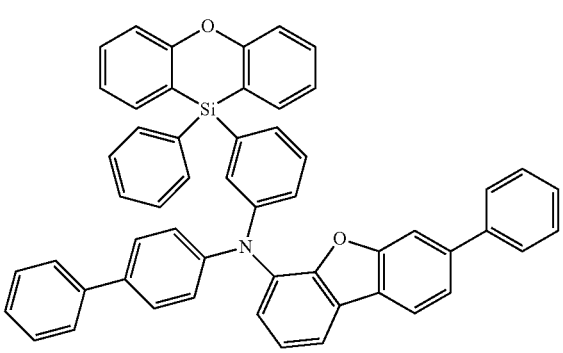
16
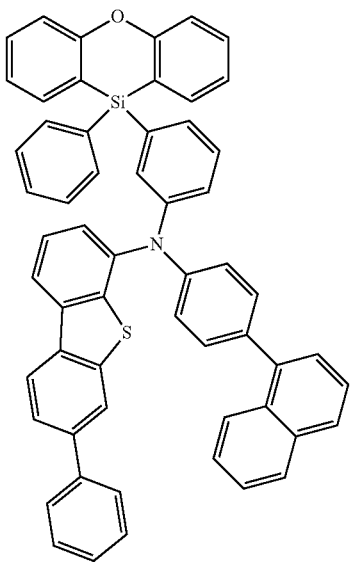

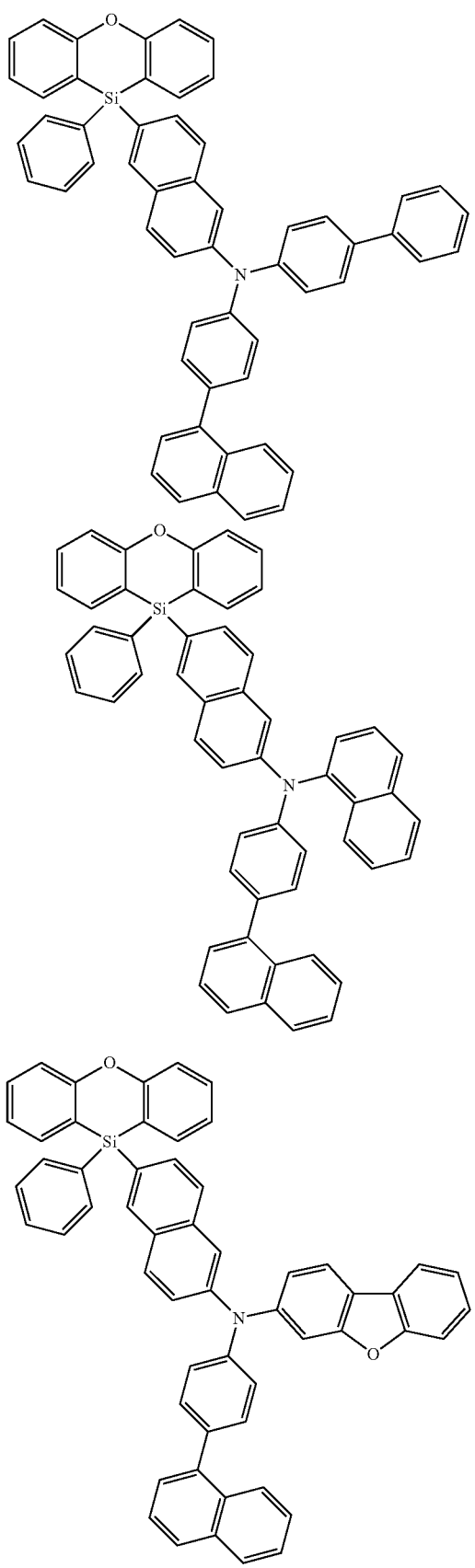
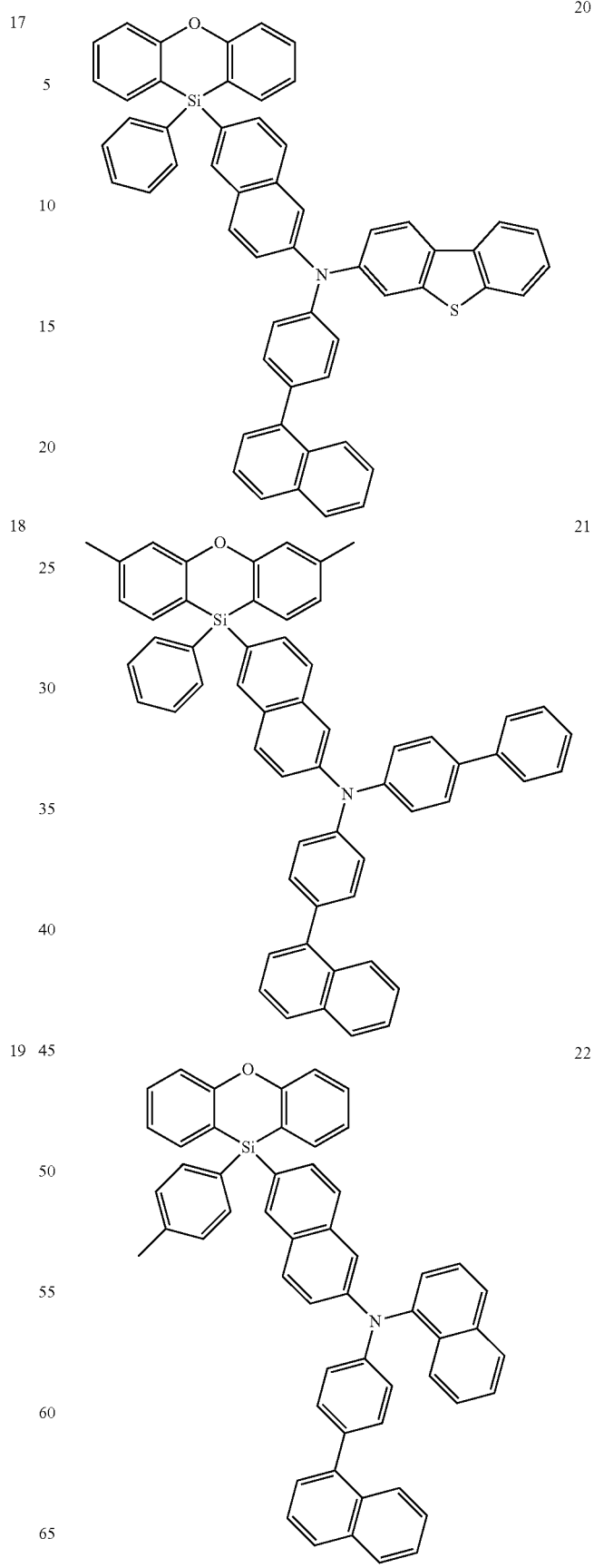

23
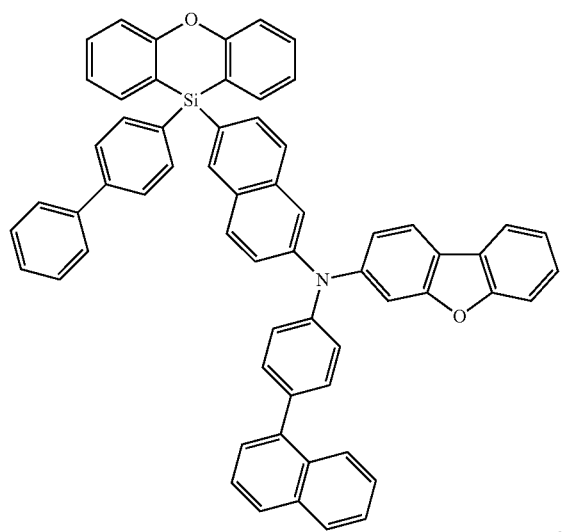
24
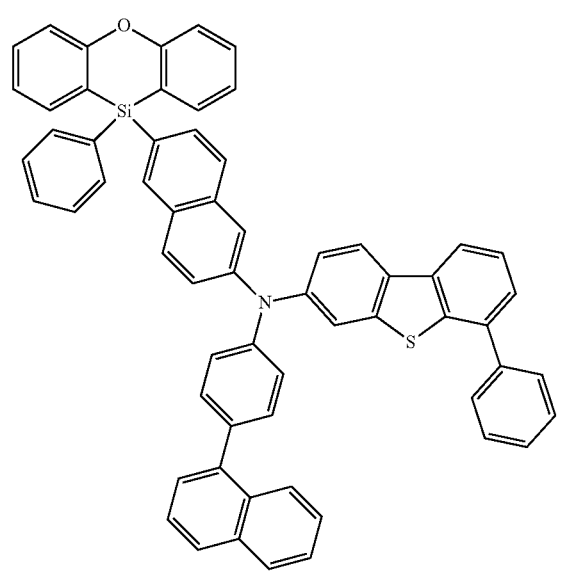
25
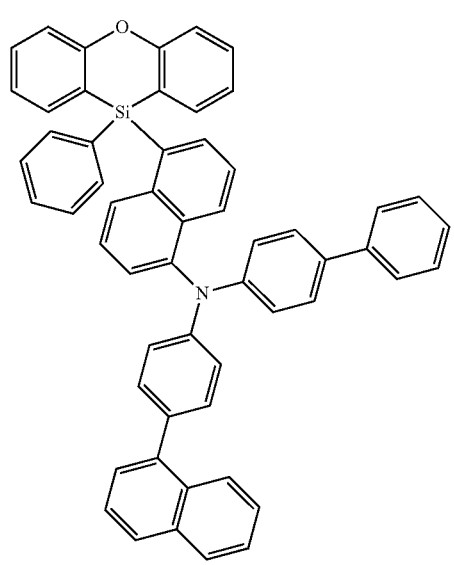
26
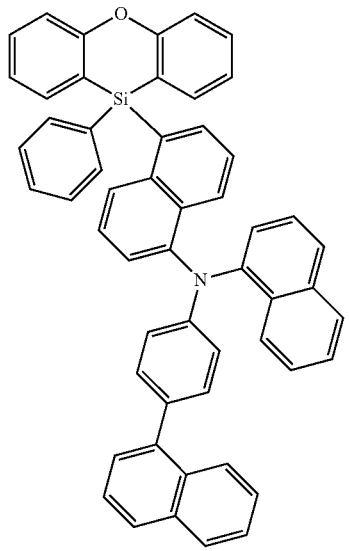
27
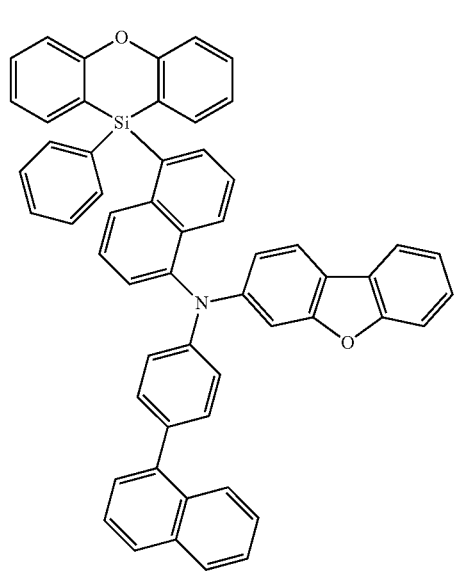
28
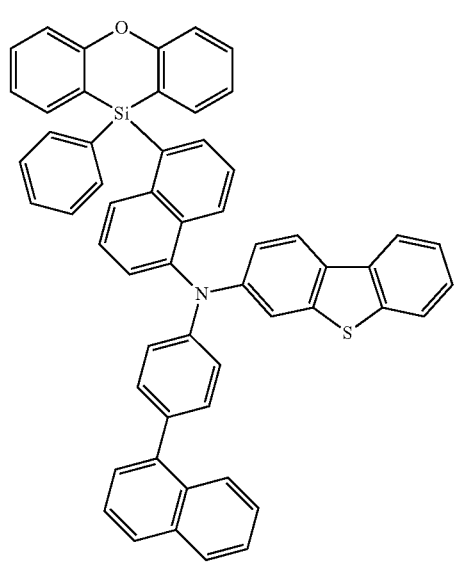

29
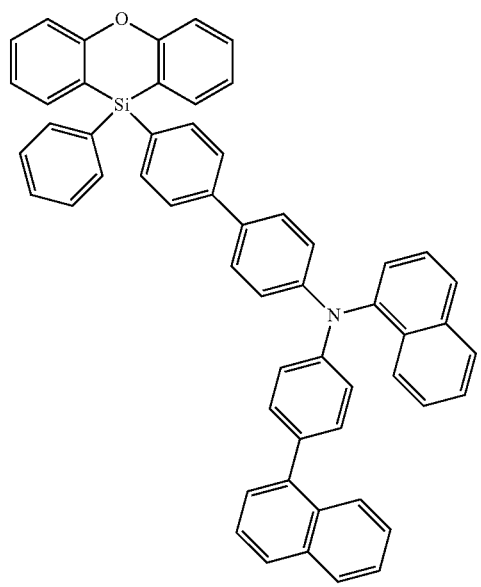
30
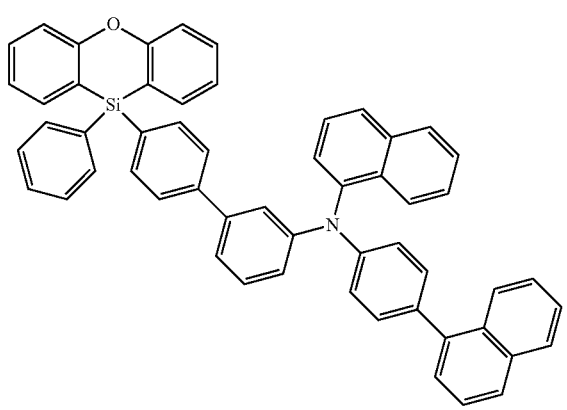
31
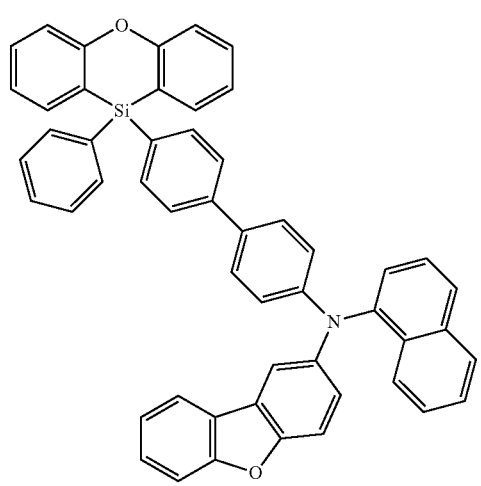
32
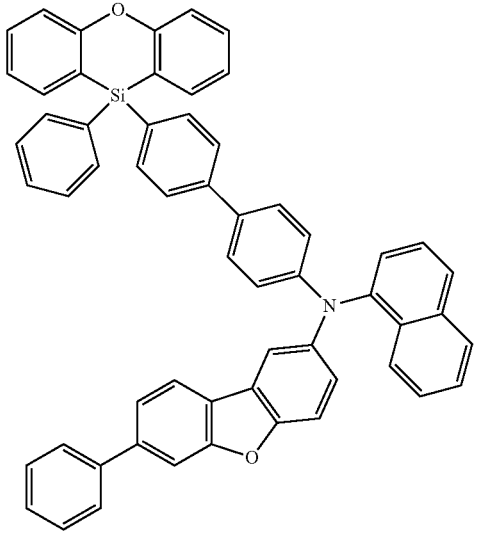
33
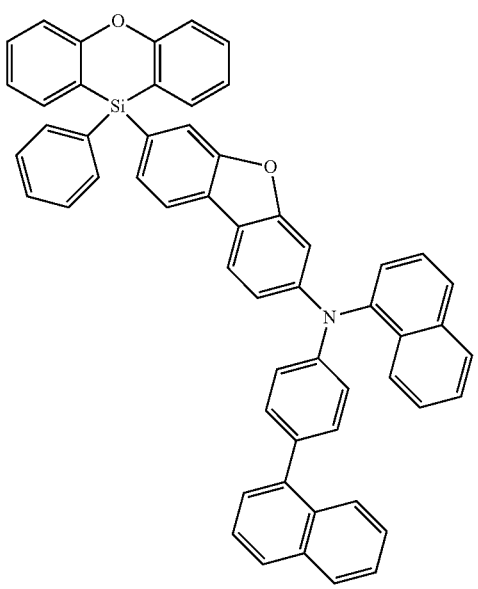

-continued

34
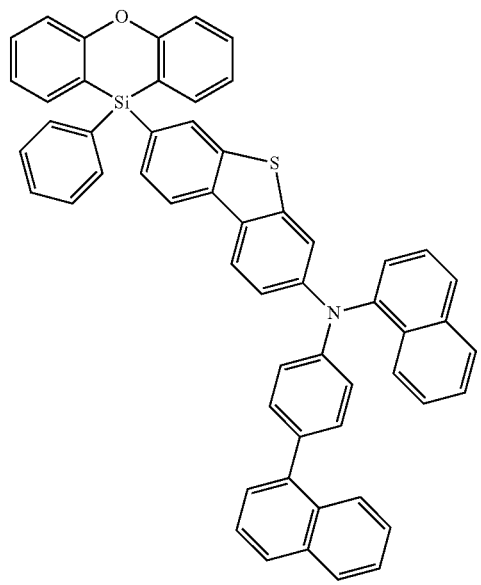

35
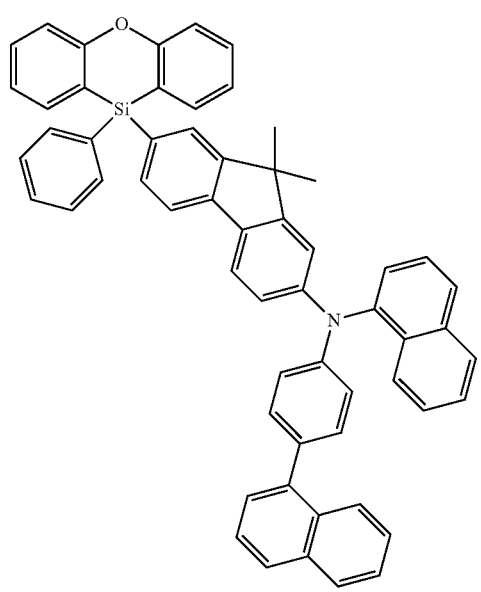

36
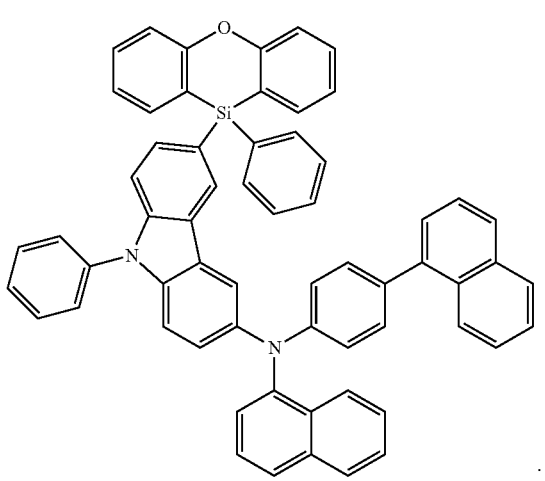

The embodiments may be realized by providing an organic electroluminescence device including a first electrode; a hole transport region on the first electrode; an emission layer on the hole transport region; an electron transport region on the emission layer; and a second electrode on the electron transport region, wherein the hole transport region includes a heterocyclic compound represented by the following Formula 1:

[Formula 1]

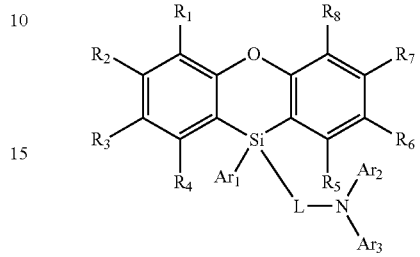

wherein, in Formula 1, $R_1$ to $R_8$ are each independently a hydrogen atom, a deuterium atom, a halogen atom, a substituted or unsubstituted silyl group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aryl group having 6 to 30 ring carbon atoms, or a substituted or unsubstituted heteroaryl group having 2 to 30 ring carbon atoms, $R_1$ to $R_8$ being separate or forming a ring by combining adjacent groups with each other, $Ar_1$ to $Ar_3$ are each independently a substituted or unsubstituted aryl group having 6 to 30 ring carbon atoms or a substituted or unsubstituted heteroaryl group having 2 to 30 ring carbon atoms, and L is a direct linkage, a substituted or unsubstituted arylene group having 6 to 30 ring carbon atoms, or a substituted or unsubstituted heteroarylene group having 2 to 30 ring carbon atoms.

The hole transport region may include a hole injection layer on the first electrode; and a hole transport layer on the hole injection layer, and the hole transport layer the heterocyclic compound represented by Formula 1.

$Ar_1$ may be a substituted or unsubstituted aryl group having 6 to 30 ring carbon atoms.

L may be a group represented by one of the following Formulae L-1 to L-4:

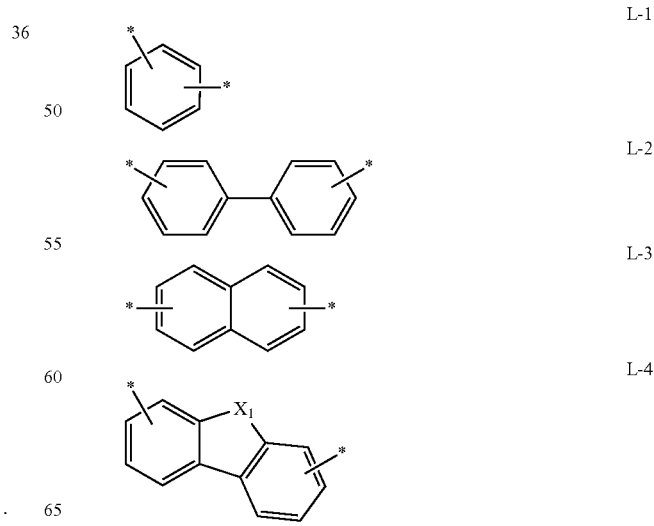

wherein, in Formula L-4, $X_1$ may be O, S, $NR_9$ or $CR_{10}R_{11}$, and $R_9$ to $R_{11}$ may each independently be a hydrogen atom, a deuterium atom, a halogen atom, a substituted or unsubstituted alkyl group having 1 to 30 carbon atoms, a substituted or unsubstituted aryl group having 6 to 30 ring carbon atoms, or a substituted or unsubstituted heteroaryl group having 2 to 30 ring carbon atoms.

At least one of $Ar_2$ or $Ar_3$ may be a substituted or unsubstituted aryl group having 6 to 30 ring carbon atoms.

At least one of $Ar_2$ or $Ar_3$ may be a group represented by the following Formula 2:

*-A-B  [Formula 2]

wherein, in Formula 2, A may be a substituted or unsubstituted phenylene group, and B may be a substituted or unsubstituted polycyclic aryl group having 6 to 30 ring carbon atoms.

$Ar_2$ and $Ar_3$ may be different from each other.

One of $Ar_2$ and $Ar_3$ may be a substituted or unsubstituted aryl group having 6 to 30 ring carbon atoms, and the other of $Ar_2$ and $Ar_3$ may be a substituted or unsubstituted aryl group having 6 to 30 ring carbon atoms or a group represented by the following Formula 3:

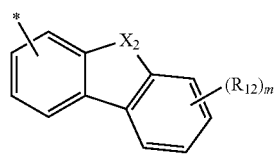

[Formula 3]

wherein, in Formula 3, $X_2$ may be O or S, in may be an integer of 1 to 4, and $R_{12}$ may be a hydrogen atom, a deuterium atom, or a substituted or unsubstituted aryl group having 6 to 30 ring carbon atoms.

The heterocyclic compound represented by Formula 1 may be a compound the following Compound Group 1:

[Compound Group 1]

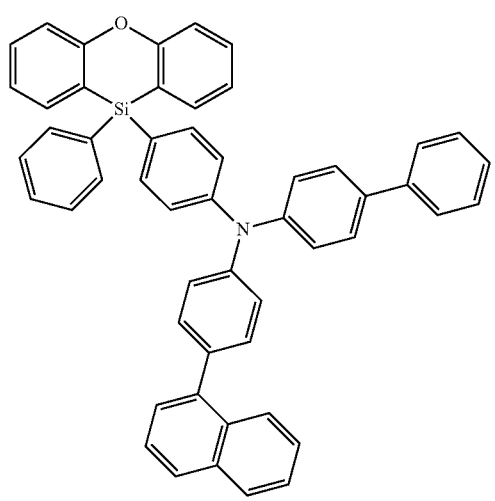

1

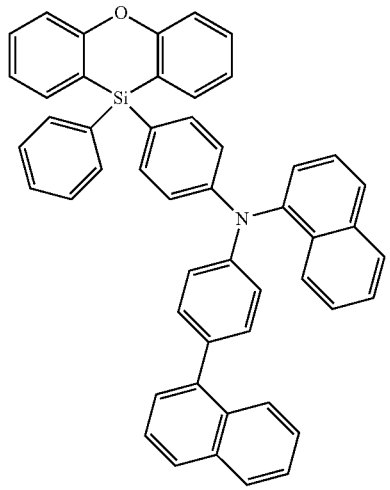

2

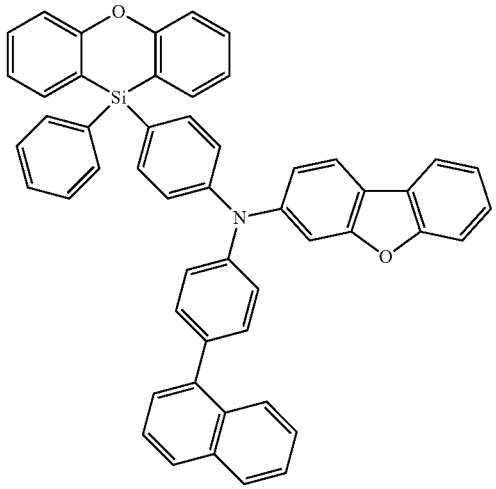

3

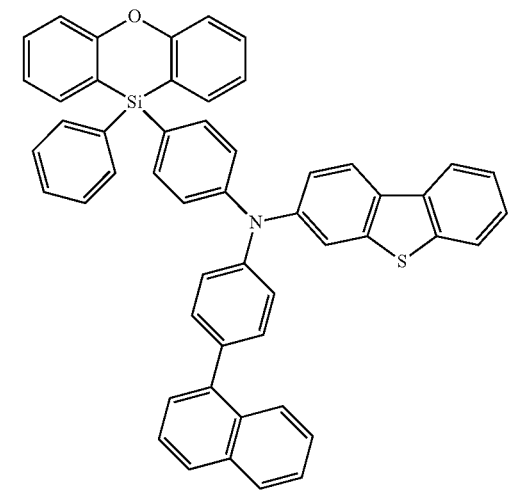

4

-continued
5
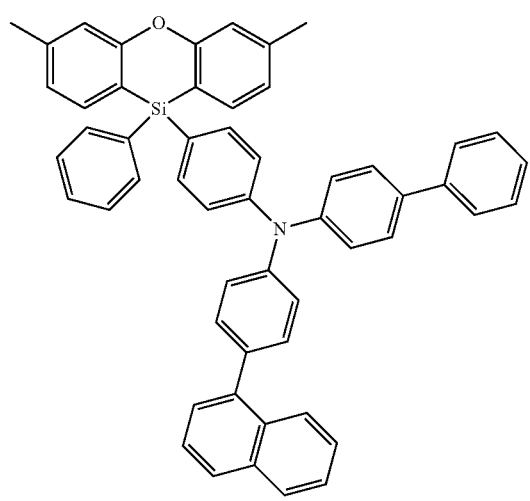
6
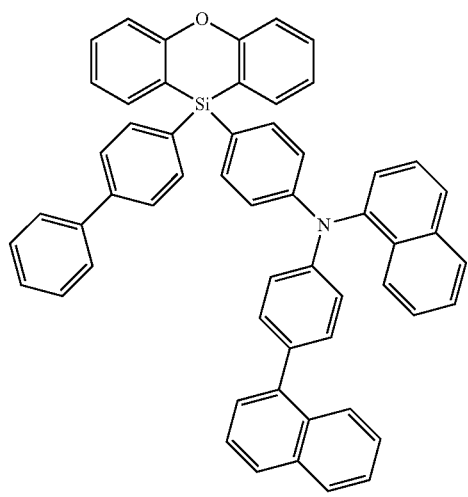
7
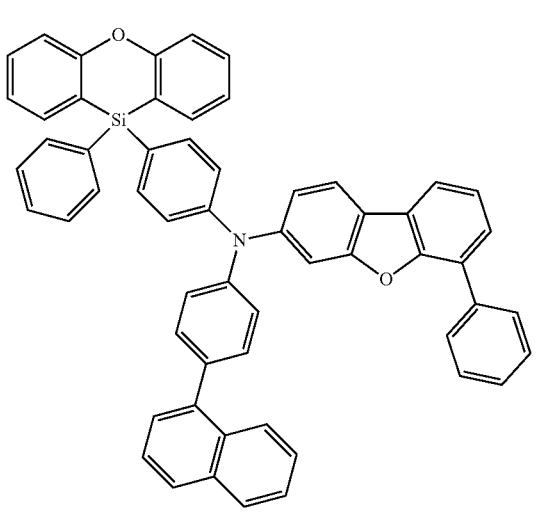
-continued
8
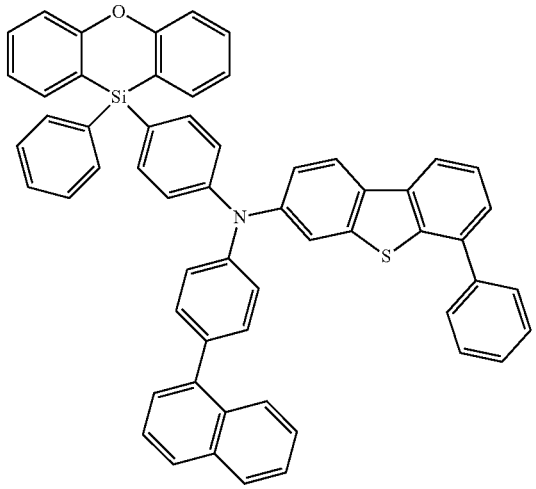
9
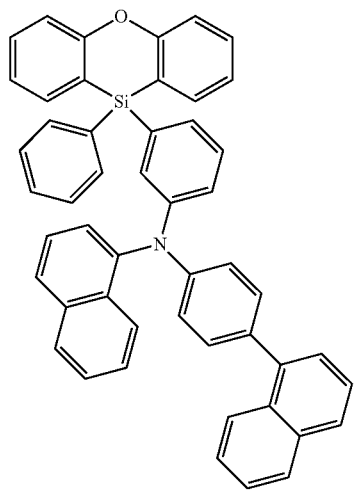
10
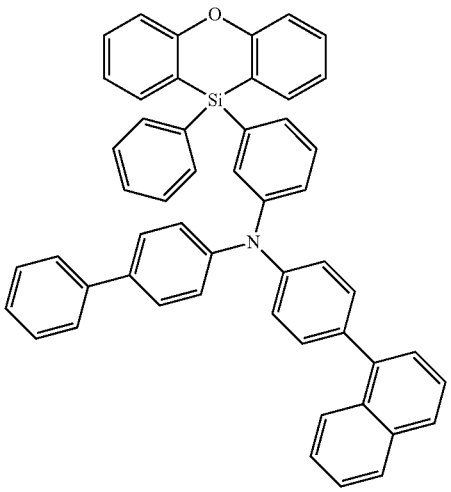

11
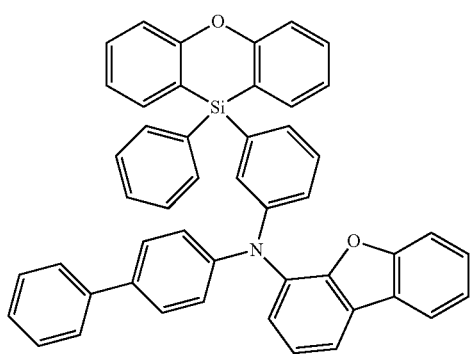
12
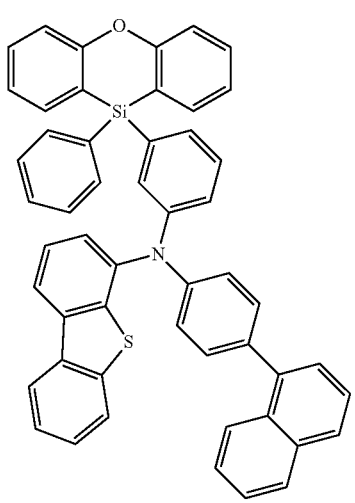
13
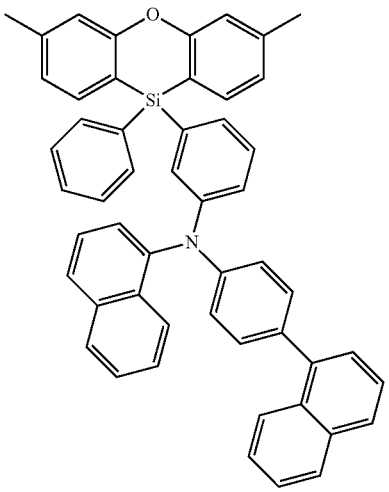
14
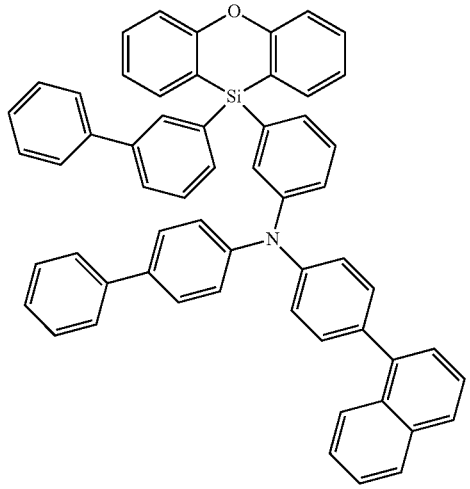
15
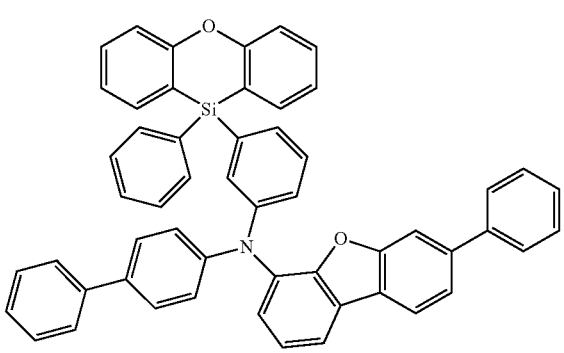
16
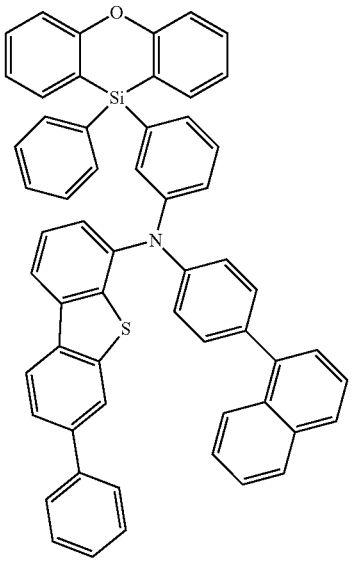

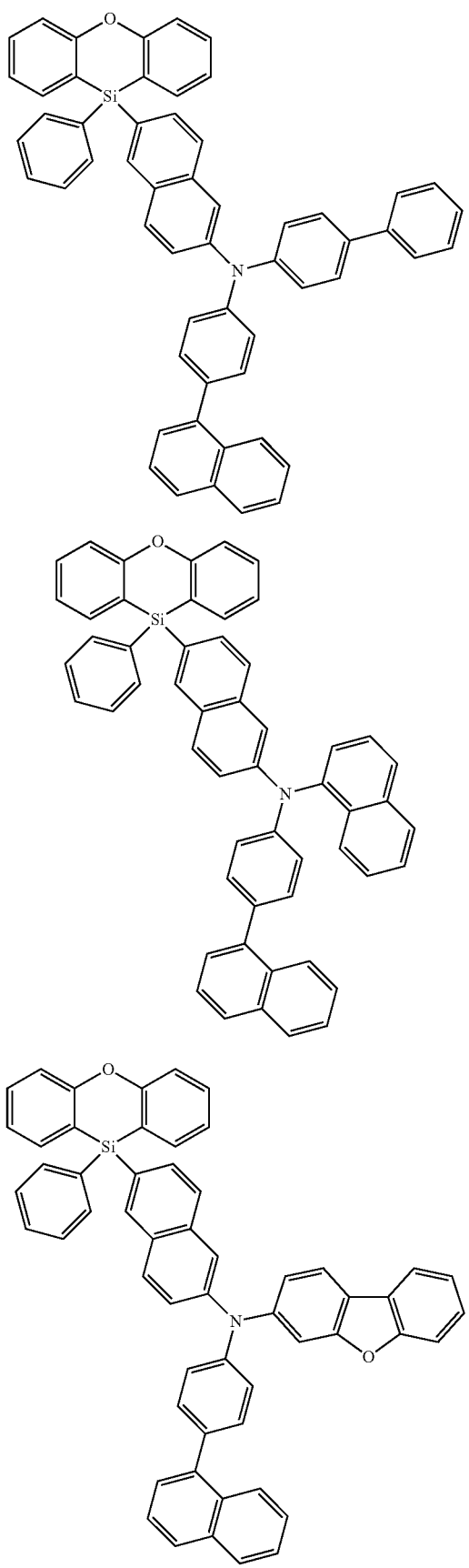
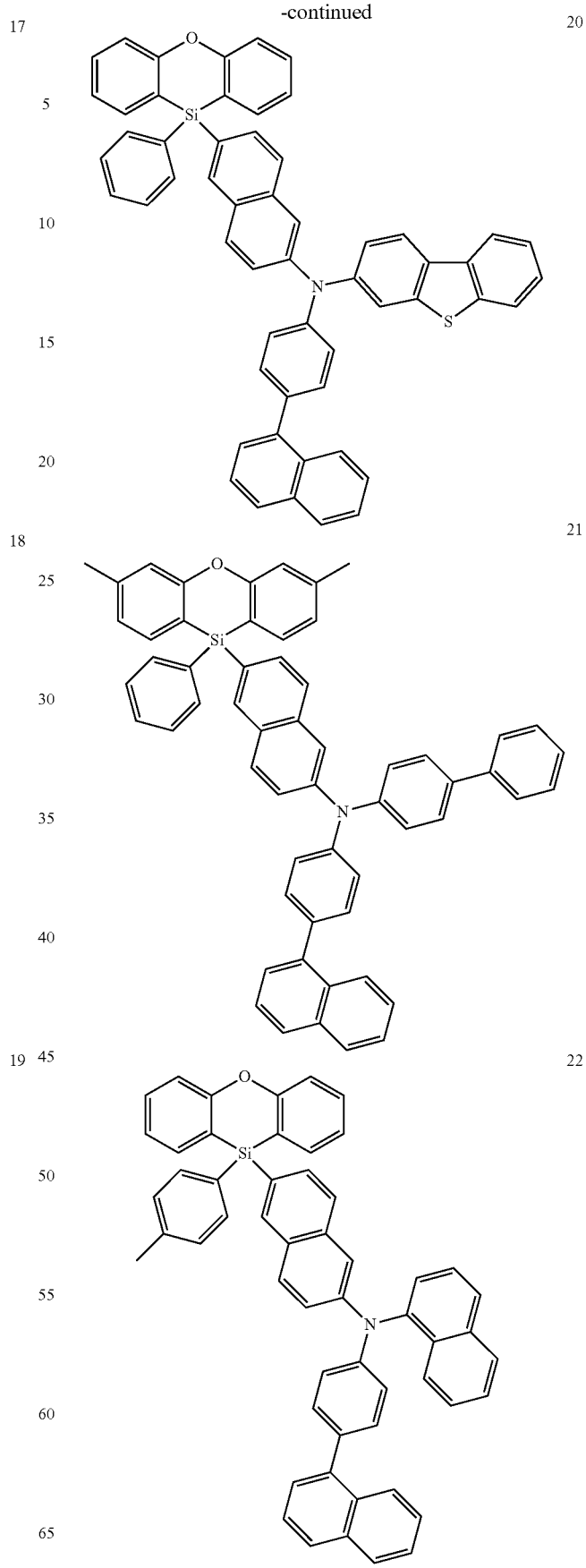

23
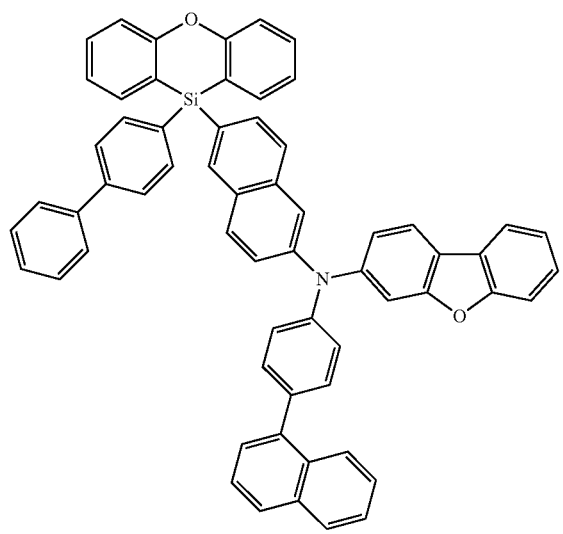
24
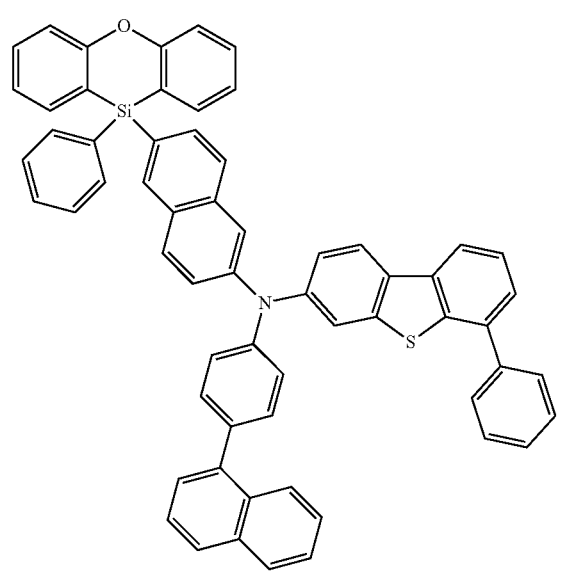
25
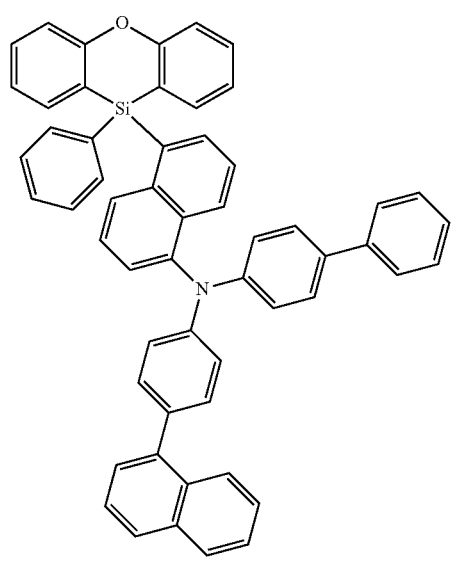
26
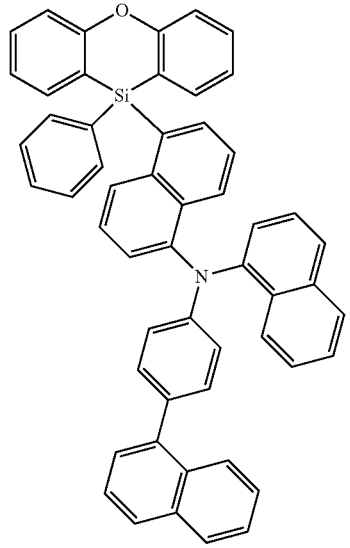
27
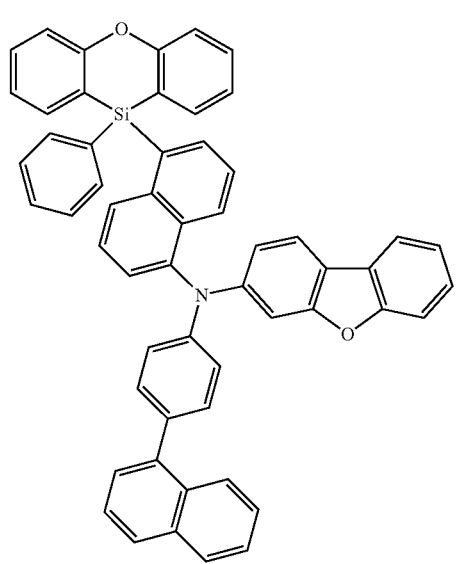
28
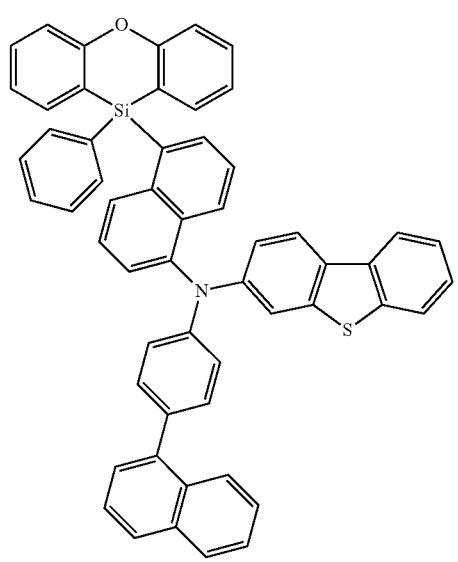

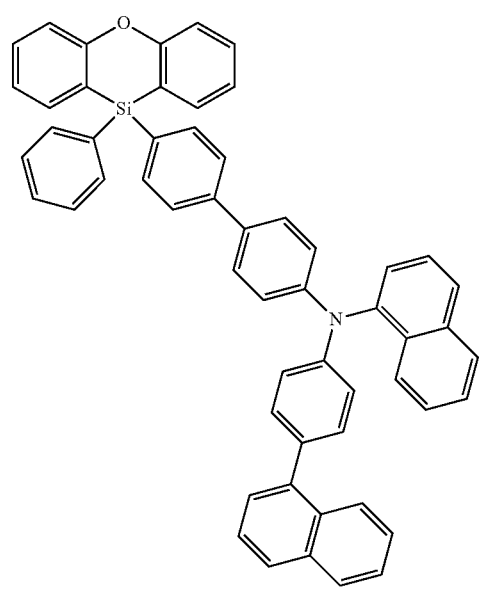
29
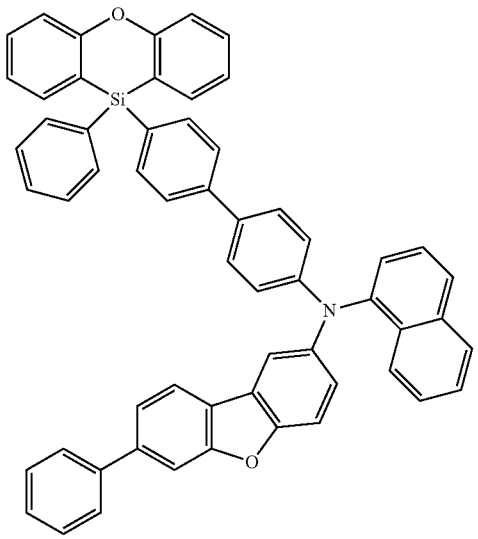
5
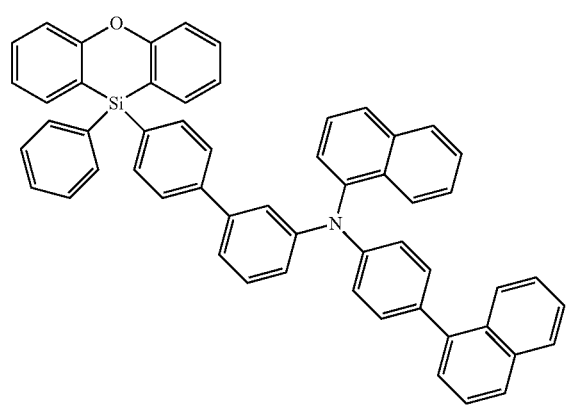
30
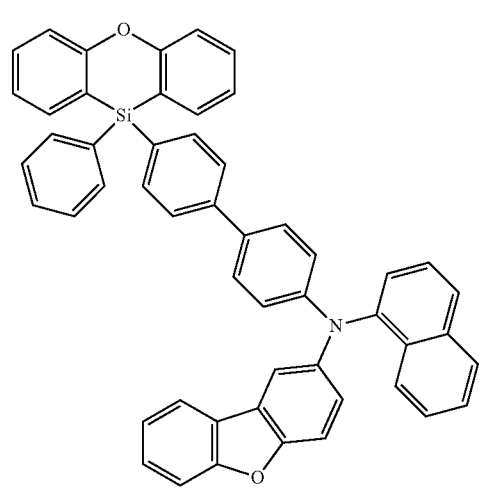
31
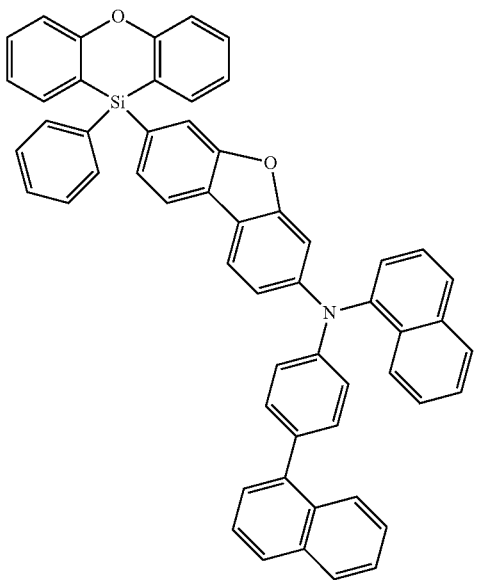
33

-continued

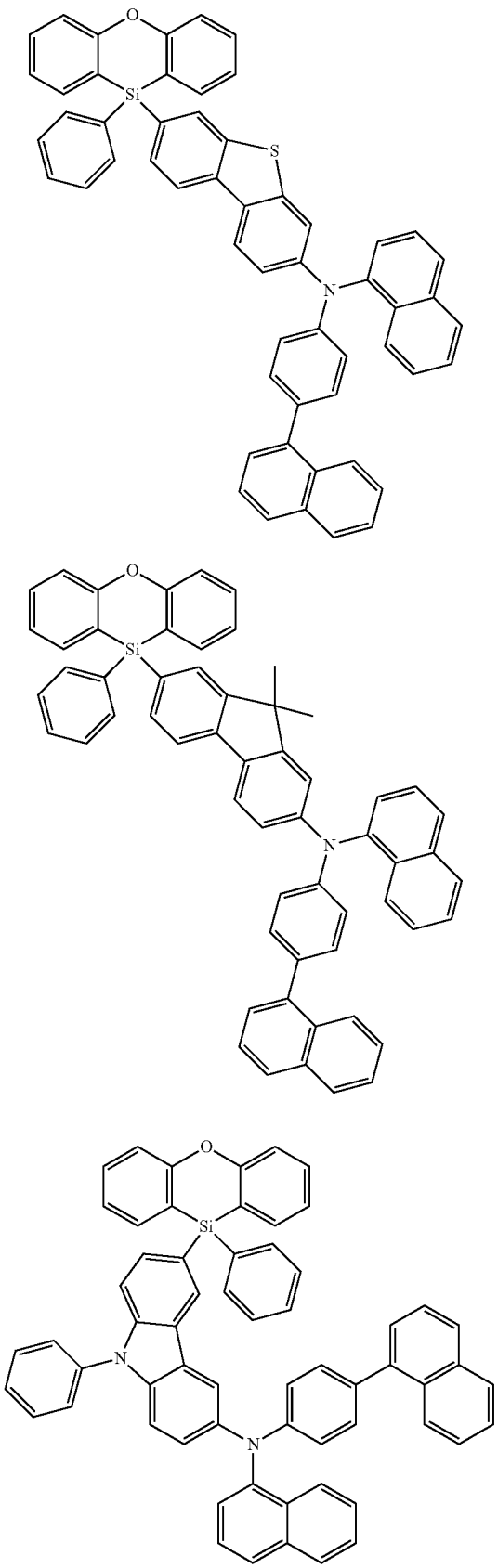

BRIEF DESCRIPTION OF THE DRAWINGS

Features will be apparent to those of skill in the art by describing in detail exemplary embodiments with reference to the attached drawings in which.

DETAILED DESCRIPTION

Figure 1:
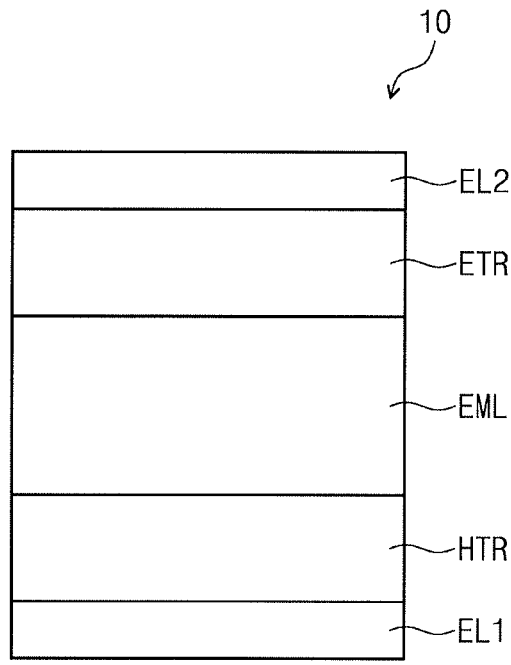
FIG. 1 illustrates a schematic cross-sectional view of an organic electroluminescence device according to an embodiment of the present disclosure.

Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art.

Like reference numerals refer to like elements for explaining each drawing. In the drawings, the sizes of elements may be enlarged for clarity of the present disclosure. It will be understood that, although the terms first, second, etc. may be used herein to describe various elements, these elements should not be limited by these terms. These terms are only used to distinguish one element from another element. For example, a first element discussed below could be termed a second element, and similarly, a second element could be termed a first element. As used herein, the singular forms are intended to include the plural forms as well, unless the context clearly indicates otherwise. As used herein, the term "or" is not an exclusive term, e.g., A or B would include A, B, or A and B.

It will be further understood that the terms "includes," "including," "comprises" or "comprising." when used in this specification, specify the presence of stated features, numerals, steps, operations, elements, parts, or a combination thereof, but do not preclude the presence or addition of one or more other features, numerals, steps, operations, elements, parts, or a combination thereof. It will also be understood that when a layer, a film, a region, a plate, etc. is referred to as being "on" another part, it can be directly on the other part, or intervening layers may also be present. On the contrary, when a layer, a film, a region, a plate, etc. is referred to as being "under" another part, it can be directly under the other part, or intervening layers may also be present.

In the present disclosure, ⎯• means a part to be connected, e.g., a bonding location.

In the present disclosure, "substituted or unsubstituted" may mean unsubstituted or substituted with at least one substituent selected from the group consisting of deuterium, halogen, cyano, nitro, amino, silyl, boron, phosphine oxide, aryl phosphine, phosphine sulfide, alkyl, alkenyl, alkynyl, aryl and heterocyclic group. In addition, each of the substituent illustrated above may be substituted or unsubstituted. For example, biphenyl may be interpreted as aryl, or phenyl substituted with phenyl.

In the present disclosure, the description of forming a ring by combining adjacent groups with each other may mean forming a substituted or unsubstituted hydrocarbon ring or a substituted or unsubstituted heterocycle by combining adjacent groups with each other. The hydrocarbon ring may include an aliphatic hydrocarbon ring and an aromatic hydrocarbon ring. The heterocycle may include an aliphatic heterocycle and an aromatic heterocycle. The hydrocarbon ring and heterocycle may be a monocycle or polycycle. In addition, the ring formed by combining adjacent groups with each other may be connected with another ring to form a spiro structure.

In the present disclosure, "an adjacent group" may mean a substituent at an atom which is directly connected with another atom at which a corresponding substituent is substituted, another substituent at an atom at which a corresponding substituent is substituted, or a substituent stereoscopically disposed at the nearest position to a corresponding substituent. For example, two methyl groups in 1,2-dimethylbenzene may be interpreted as "adjacent groups", and two ethyl groups in 1,1-diethylcyclopentene may be interpreted as "adjacent groups".

In the present disclosure, examples of a halogen atom are a fluorine atom, a chlorine atom, a bromine atom, or an iodine atom.

In the present disclosure, the alkyl group may have a linear, branched or cyclic form. The carbon number of the alkyl group may be 1 to 30, 1 to 20, 1 to 10, or 1 to 6. Examples of the alkyl group may include methyl, ethyl, n-propyl, isopropyl, n-butyl, s-butyl, t-butyl, i-butyl, 2-ethylbutyl, 3,3-dimethylbutyl, n-pentyl, i-pentyl, neopentyl, t-pentyl, cyclopentyl, 1-methylpentyl, 3-methylpentyl, 2-ethylpentyl, 4-methyl-2-pentyl, n-hexyl, 1-methylhexyl, 2-ethylhexyl, 2-butylhexyl, cyclohexyl, 4-methylcyclohexyl, 4-t-butylcyclohexyl, n-heptyl, 1-methylheptyl, 2,2-dimethylheptyl, 2-ethylheptyl, 2-butylheptyl, n-octyl, t-octyl, 2-ethyloctyl, 2-butyloctyl, 2-hexyloctyl, 3,7-dimethyloctyl, cyclooctyl, n-nonyl, n-decyl, adamantyl, 2-ethyldecyl, 2-butyldecyl, 2-hexyldecyl, 2-octyldecyl, n-undecyl, n-dodecyl, 2-ethyldodecyl, 2-butyldodecyl, 2-hexyldodecyl, 2-octyldodecyl, n-tridecyl, n-tetradecyl, n-pentadecyl, n-hexadecyl, 2-ethylhexadecyl, 2-butylhexadecyl, 2-hexylhexadecyl, 2-octylhexadecyl, n-heptadecyl, n-octadecyl, n-nonadecyl, n-eicosyl, 2-ethyl eicosyl, 2-butyl eicosyl, 2-hexyl eicosyl, 2-octyl eicosyl, n-heneicosyl, n-docosyl, n-tricosyl, n-tetracosyl, n-pentacosyl, n-hexacosyl, n-heptacosyl, n-octacosyl, n-nonacosyl, n-triacontyl, etc., without limitation.

In the present disclosure, the aryl group means any functional group or substituent derived from an aromatic hydrocarbon ring. The aryl group may be monocyclic aryl or polycyclic aryl. The carbon number of the aryl group for forming a ring may be 6 to 30, 6 to 20, or 6 to 15. Examples of the aryl group may include phenyl, naphthyl, fluorenyl, anthracenyl, phenanthryl, biphenyl, terphenyl, quaterphenyl, quinqphenyl, sexiphenyl, triphenylene, pyrenyl, benzofluoranthenyl, chrysenyl, etc., without limitation.

In the present disclosure, the fluorenyl group may be substituted, and two substituents may be combined with each other to form a spiro structure.

In the present disclosure, the above explanation on the aryl group may be applied to the arylene group, except that the arylene is divalent.

In the present disclosure, the heteroaryl group may be heteroaryl including at least one of O, N, P, Si, or S as a heteroatom. The carbon number of the heteroaryl group for forming a ring may be 2 to 30, 2 to 20, or 2 to 15. The heteroaryl group may be monocyclic heteroaryl or polycyclic heteroaryl. Polycyclic heteroaryl may have bicyclic or tricyclic structure, for example. Examples of the heteroaryl may include thienyl, furanyl, pyrrolyl, imidazole, thiazole, oxazole, oxadiazole, triazole, pyridyl, bipyridyl, pyrimidyl, triazine, triazole, acridyl, pyridazine, pyrazinyl, quinolinyl, quinazoline, quinoxalinyl, phenoxazyl, phthalazinyl, pyrido pyrimidinyl, pyrido pyrazinyl, pyrazino pyrazinyl, isoquinoline, indole, carbazole, N-arylcarbazole, N-heteroaryl carbazole, N-alkyl carbazole, benzoxazole, benzoimidazole, benzothiazole, benzocarbazole, benzothienyl, dibenzothiophenyl, thienothienyl, benzofuranyl, phenanthroline, thiazolyl, isoxazolyl, oxadiazolyl, thiadiazolyl, benzothiazolyl, phenothiazinyl, dibenzosilole, dibenzofuranyl, etc., without limitation.

The above explanation on the heteroaryl group may be applied to the heteroarylene group, except that the heteroarylene is divalent.

In the present disclosure, the silyl group may include alkyl silyl and aryl silyl. Examples of the silyl group may include trimethylsilyl, triethylsilyl, t-butyl dimethylsilyl, vinyl dimethylsilyl, propyl dimethylsilyl, triphenylsilyl, diphenylsilyl, phenylsilyl, etc., without limitation.

In the present disclosure, the boron group may include alkyl boryl and aryl boron. Examples of the boron group may include trimethyl boron, triethyl boron, t-butyl dimethyl boron, triphenyl boron, diphenyl boron, phenyl boron, etc., without limitation.

In the present disclosure, the alkenyl group may be linear or branched. The carbon number is not specifically limited, and may be 2 to 30, 2 to 20, or 2 to 10. Examples of the alkenyl group may include vinyl, 1-butenyl, 1-pentenyl, 1,3-butadienyl aryl, styrenyl, styrylvinyl, etc., without limitation.

In the present disclosure, the carbon number of the alkynyl group is not specifically limited, and may be 2 to 30, 2 to 20, or 2 to 10.

In the present disclosure, a direct linkage may include a single bond.

In the present disclosure, the carbon number of the amino group is not specifically limited, and may be 1 to 30. The amino group may include alkyl amino and aryl amino. Examples of the amino group may include methylamino, dimethylamino, phenylamino, diphenylamino, naphthylamino, 9-methyl-anthracenylamino, triphenylamino, etc., without limitation.

Hereinafter, the heterocyclic compound according to an embodiment of the present disclosure will be explained.

The heterocyclic compound according to an embodiment of the present disclosure may be represented by the following Formula 1:

[Formula 1]

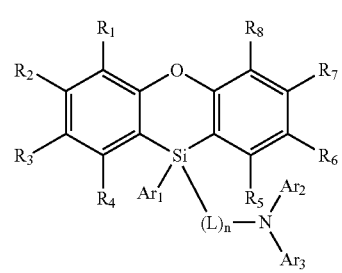

In Formula 1, $R_1$ to $R_8$ may each independently be or include, e.g., a hydrogen atom, a deuterium atom, a halogen atom, a substituted or unsubstituted silyl group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aryl group having 6 to 30 ring carbon atoms, or a substituted or unsubstituted heteroaryl group having 2 to 30 ring carbon atoms. In an implementation, $R_1$ to $R_8$ may be separate or may form a ring by combining adjacent groups with each other. $Ar_1$ to $Ar_3$ may each independently be or include, e.g., a substituted or unsubstituted aryl group having 6 to 30 ring carbon atoms or a substituted or unsubstituted heteroaryl group having 2 to 30 ring carbon atoms. L may be or may include, e.g., a direct linkage, a substituted or unsubstituted arylene group having 6 to 30 ring carbon atoms, or a substituted or unsubstituted heteroarylene group having 2 to 30 ring carbon atoms.

In an implementation, $Ar_1$ may be or may include, e.g., a substituted or unsubstituted aryl group having 6 to 30 ring carbon atoms. For example, $Ar_1$ may be a substituted or unsubstituted phenyl group or a substituted or unsubstituted biphenyl group. In an implementation, $Ar_1$ may be, e.g., a phenyl group which is unsubstituted or substituted with alkyl.

In an implementation, L may be or may include, e.g., a substituted or unsubstituted arylene group having 6 to 30 ring carbon atoms or a substituted or unsubstituted heteroarylene group having 2 to 30 ring carbon atoms. In an implementation, L may be a substituted or unsubstituted arylene group having 6 to 15 ring carbon atoms or a substituted or unsubstituted heteroarylene group having 2 to 15 ring carbon atoms.

In an implementation, L may be, e.g., a group represented by one of the following Formulae L-1 to L-4, each of which may be substituted or unsubstituted:

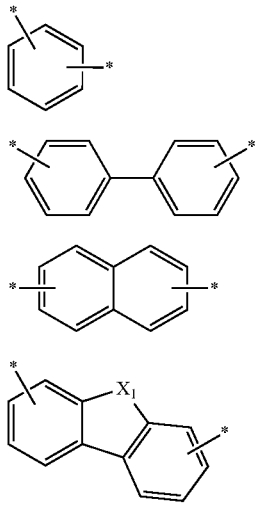

L-1

L-2

L-3

L-4

In Formula L-4, $X_1$ may be, e.g., O, S, $NR_9$ or $CR_{10}R_{11}$, and $R_9$ to $R_{11}$ may each independently be or include, e.g., a hydrogen atom, a deuterium atom, a halogen atom, a substituted or unsubstituted alkyl group having 1 to 30 carbon atoms, a substituted or unsubstituted aryl group having 6 to 30 ring carbon atoms, or a substituted or unsubstituted heteroaryl group having 2 to 30 ring carbon atoms.

In an implementation, in Formula L-4, when $X_1$ is $NR_9$, $R_9$ may be a substituted or unsubstituted aryl group having 6 to 30 ring carbon atoms, e.g., a substituted or unsubstituted phenyl.

In an implementation, in Formula L-4, when $X_1$ is $CR_{10}R_{11}$, each of $R_{10}$ and $R_{11}$ may independently be, e.g., a substituted or unsubstituted alkyl group having 1 to 30 carbon atoms or a substituted or unsubstituted aryl group having 6 to 30 ring carbon atoms. In an implementation, in Formula L-4, when $X_1$ is $CR_{10}R_{11}$, at least one of $R_{10}$ or $R_{11}$ may be, e.g., a substituted or unsubstituted alkyl group having 1 to 30 carbon atoms. In an implementation, in Formula L-4, when $X_1$ is $CR_{10}R_{11}$, $R_{10}$ and $R_{11}$ may be, e.g., a substituted or unsubstituted methyl.

In an implementation, L may be, e.g., a group represented by one of the following formulae, each of which may be substituted or unsubstituted:

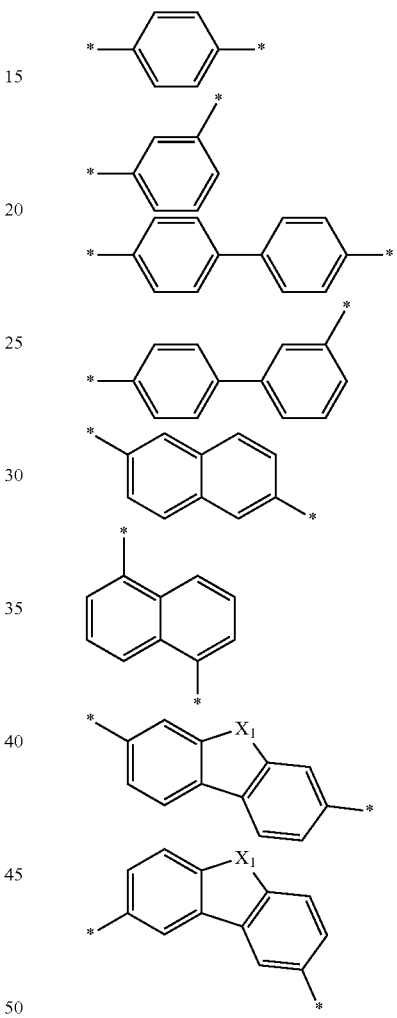

In the above formulae, $X_1$ may be the same as defined above with respect to Formula L-4.

In an implementation, in Formula 1, at least one of $Ar_2$ or $Ar_3$ may be, e.g., a substituted or unsubstituted aryl group having 6 to 30 ring carbon atoms. In an implementation, in Formula 1, at least one of $Ar_2$ or $Ar_3$ may be, e.g., a substituted or unsubstituted aryl group having 6 to 15 ring carbon atoms.

In an implementation, at least one of $Ar_2$ or $Ar_3$ may be a group represented by the following Formula 2.

\*-A-B  [Formula 2]

In Formula 2, A may be or may include, e.g., a substituted or unsubstituted phenylene group, and B may be or may include, e.g., a substituted or unsubstituted polycyclic aryl group having 6 to 30 ring carbon atoms. For example, B may be a bicyclic or tricyclic aryl group. In an implementation, B may be or may include, e.g., a substituted or unsubstituted polycyclic aryl group having 10 to 30 ring carbon atoms.

In an implementation, the group represented by Formula 2 may be a group represented by the following Formula 2-1:

[Formula 2-1]

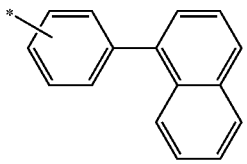

In an implementation, in Formula 1, one of $Ar_2$ and $Ar_3$ may be or include, e.g., a substituted or unsubstituted aryl group having 6 to 30 ring carbon atoms, and the other of $Ar_2$ and $Ar_3$ may be or include, e.g., a substituted or unsubstituted aryl group having 6 to 30 ring carbon atoms or a group represented by the following Formula 3. In an implementation, $Ar_2$ and $Ar_3$ may be different from each other.

[Formula 3]

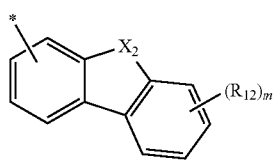

In Formula 3, $X_2$ may be, e.g., O or S, m may be, e.g., an integer of 1 to 4, and $R_{12}$ may be or may include, e.g., a hydrogen atom, a deuterium atom, or a substituted or unsubstituted aryl group having 6 to 30 ring carbon atoms.

In an implementation, in Formula 3, m may be, e.g., 0 or 1. In an implementation, when m is 1, $R_{12}$ may be or may include, e.g., a substituted or unsubstituted aryl group having 6 to 30 ring carbon atoms. In an implementation, in Formula 3, when m is 1, $R_{12}$ may be or include, e.g., a substituted or unsubstituted phenyl. In an implementation, the group represented by Formula 3 may be a group represented by one of the following formulae:

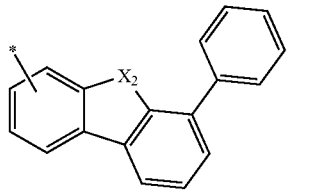

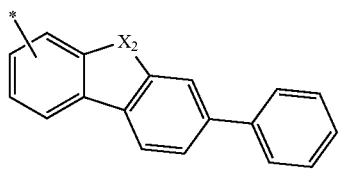

In an implementation, in Formula 1, each of $R_1$ to $R_8$ may be, e.g., a hydrogen atom. In an implementation, at least one of $R_1$ to $R_8$ may be substituted with a substituent other than hydrogen. In an implementation, at least one of $R_1$ to $R_8$ may be or may include a substituted or unsubstituted alkyl group having 1 to 30 carbon atoms, e.g., a substituted or unsubstituted alkyl group having 1 to 10 carbon atoms.

In an implementation, the compound represented by Formula 1 may be a compound represented by the following Formula 1-1.

[Formula 1-1]

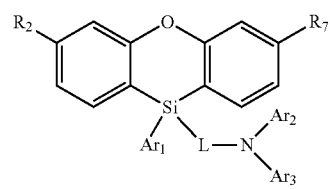

In Formula 1-1, $R_2$, $R_7$, $Ar_1$ to $Ar_3$, and L may be the same as defined above with respect to Formula 1. In an implementation, at least one of $R_2$ or $R_7$ may be a substituted or unsubstituted alkyl group having 1 to 30 carbon atoms, e.g., a substituted or unsubstituted alkyl group having 1 to 10 carbon atoms.

In an implementation, the compound represented by Formula 1 may be a monoamine compound.

In an implementation, the heterocyclic compound represented by Formula 1 may be a compound of the following Compound Group 1.

[Compound Group 1]

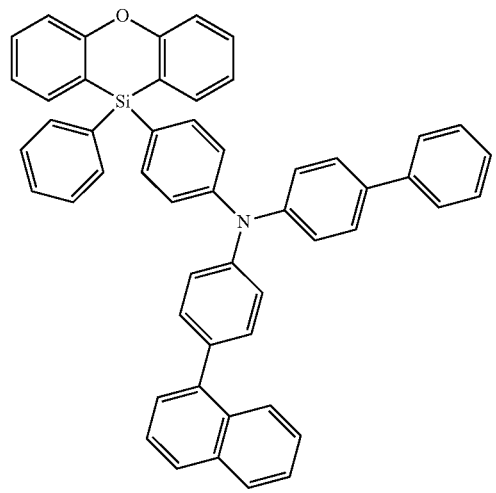

1

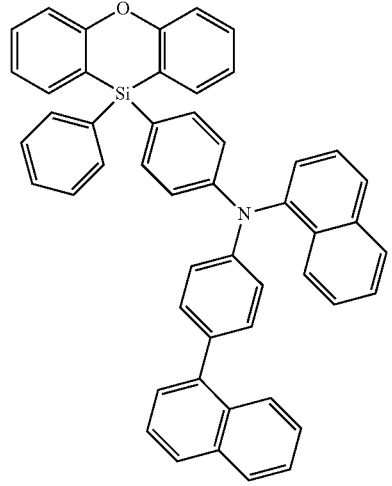

2

-continued
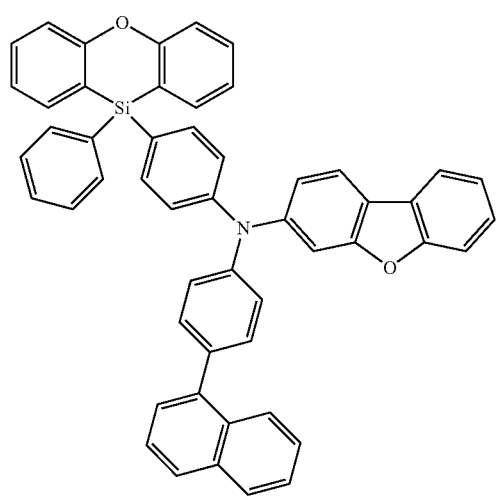
3
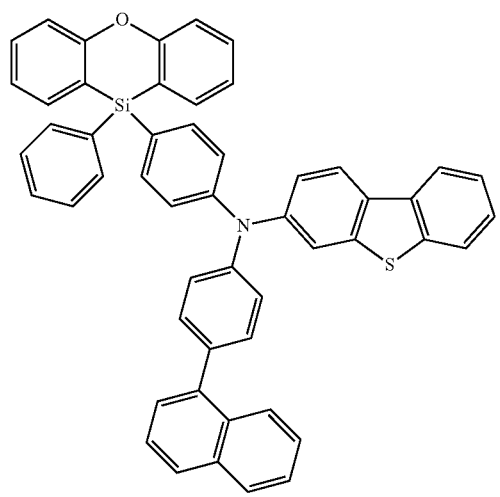
4
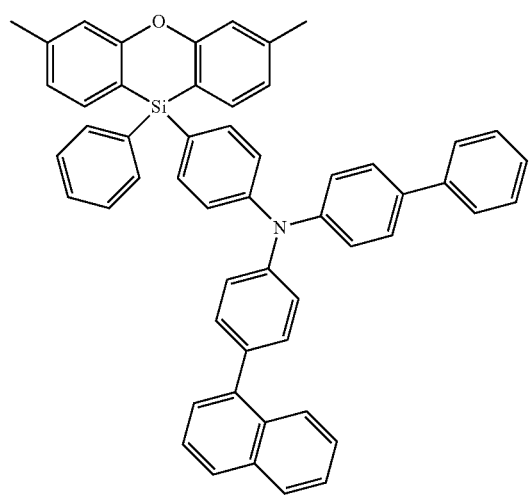
5
-continued
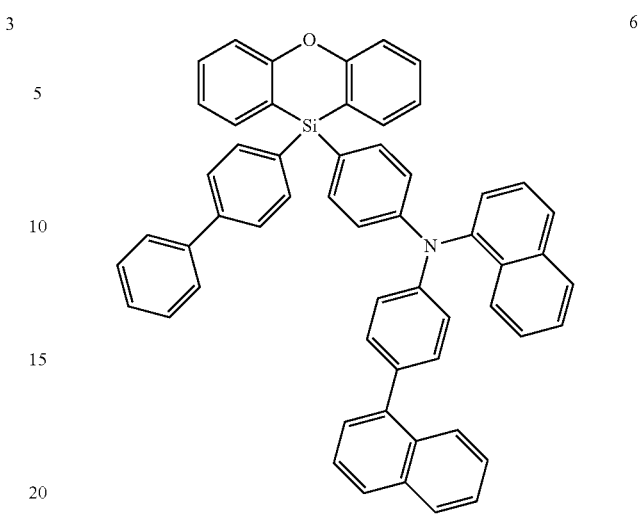
6
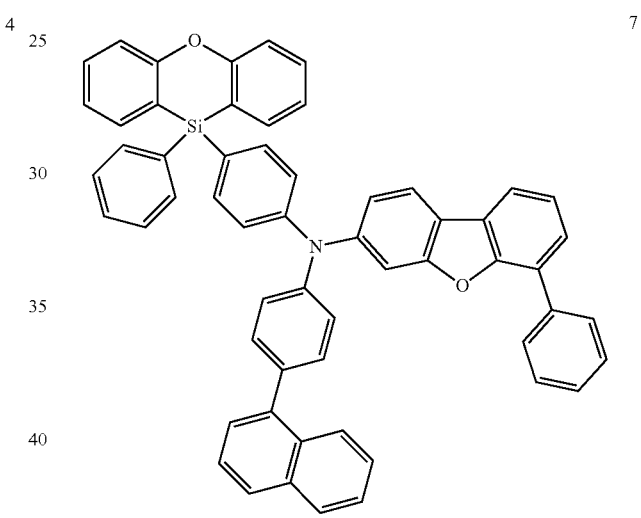
7
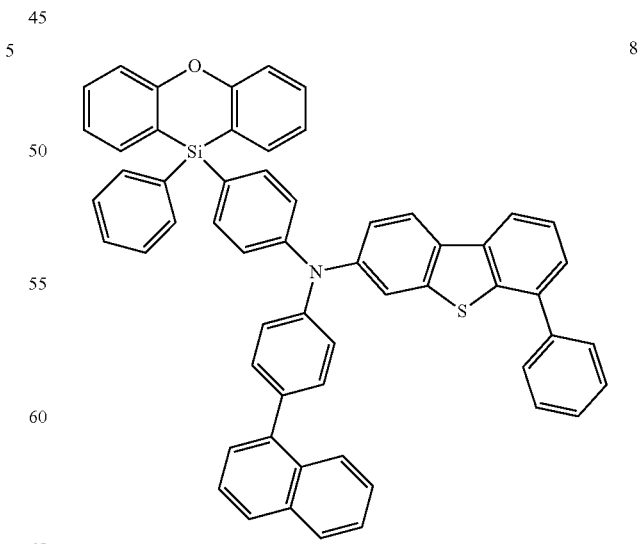
8

9
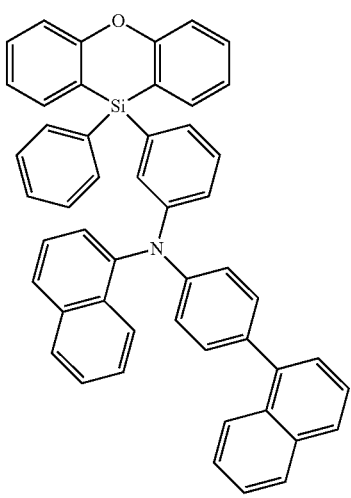
10
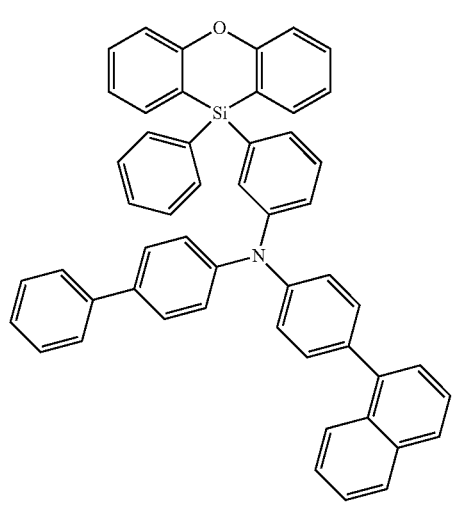
11
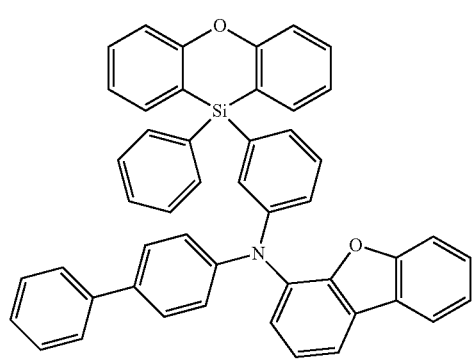
12
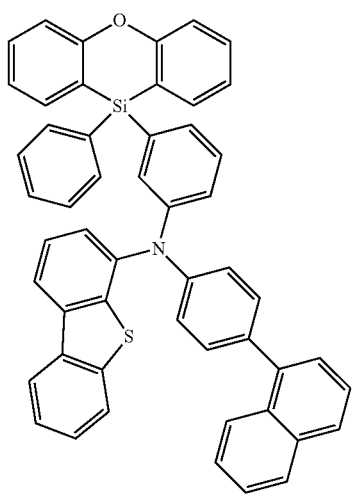
13
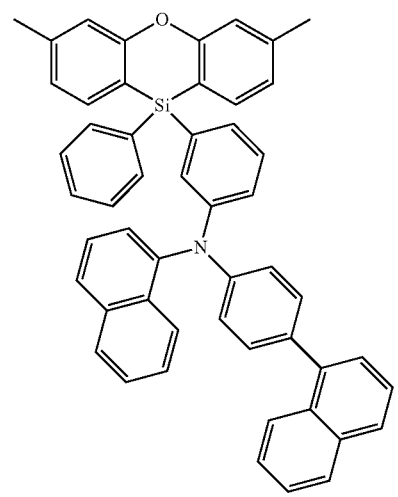
14
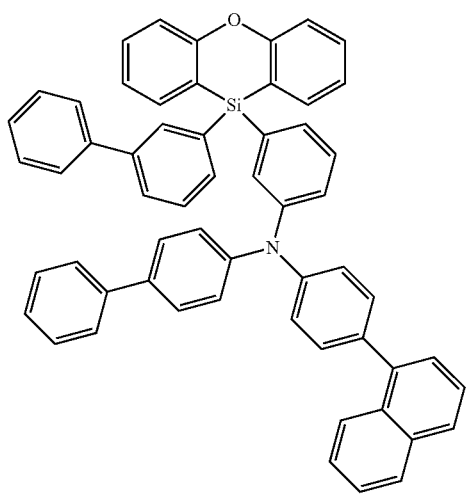

15
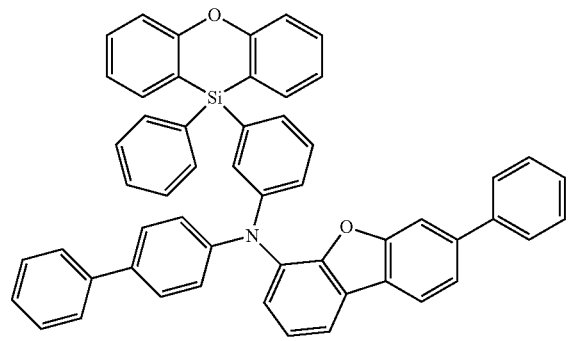
16
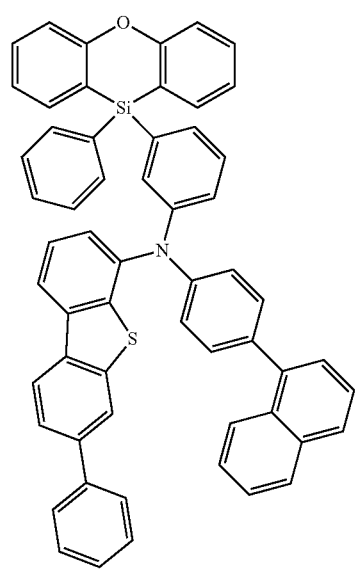
17
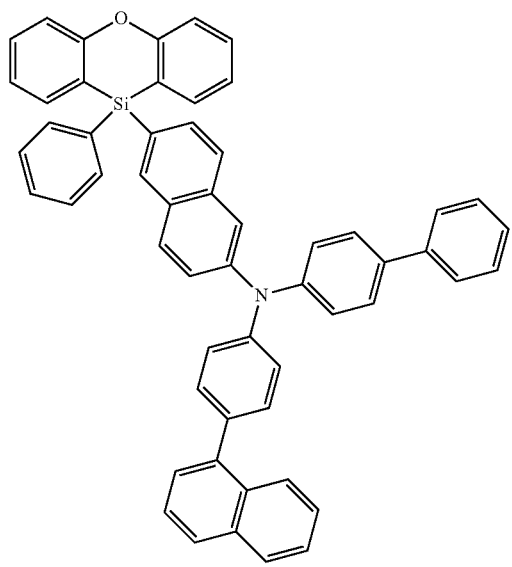
18
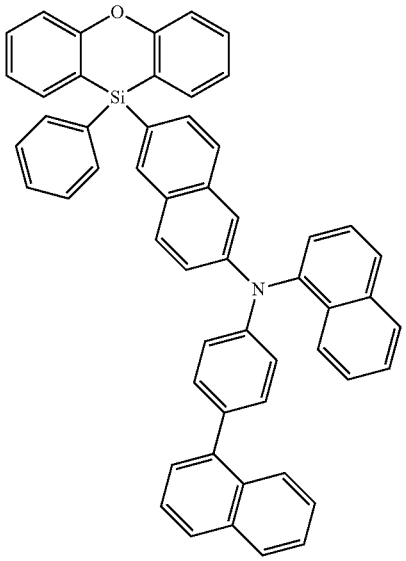
19
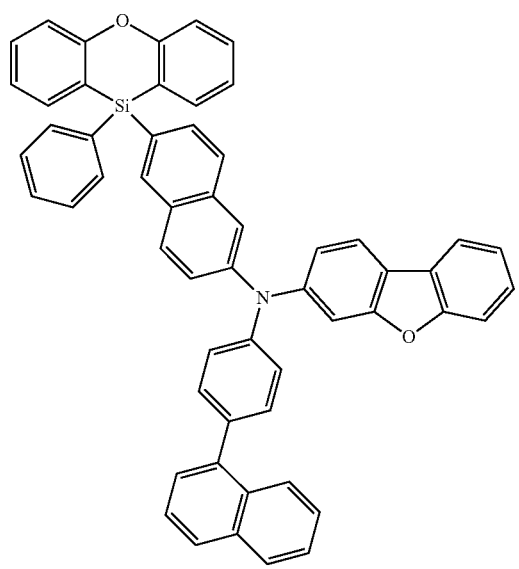
20
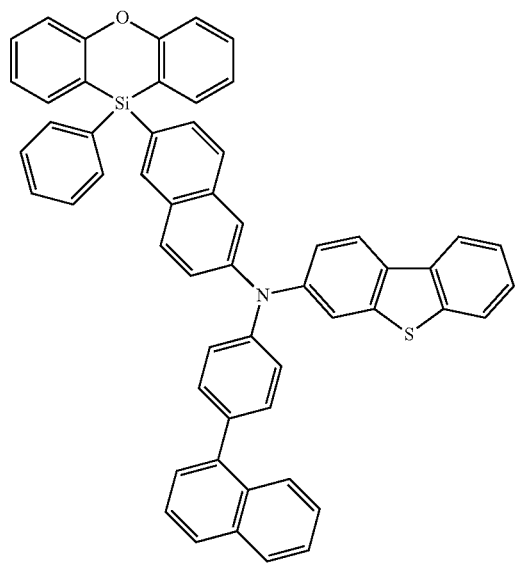

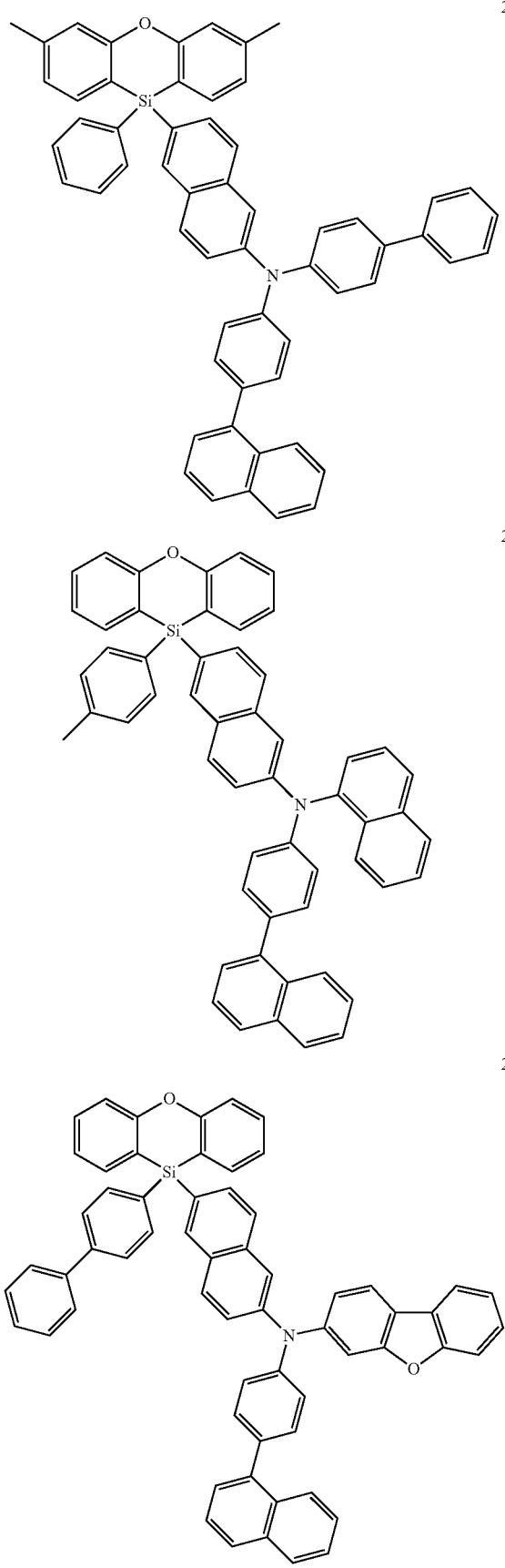
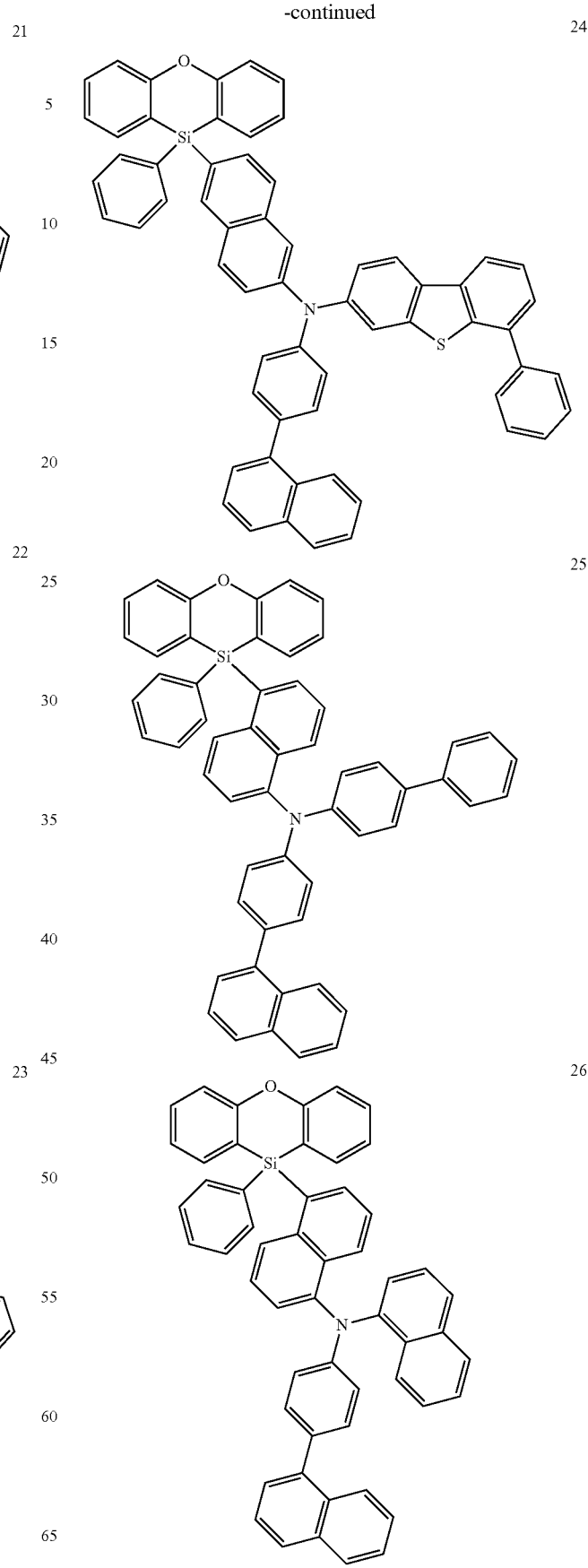

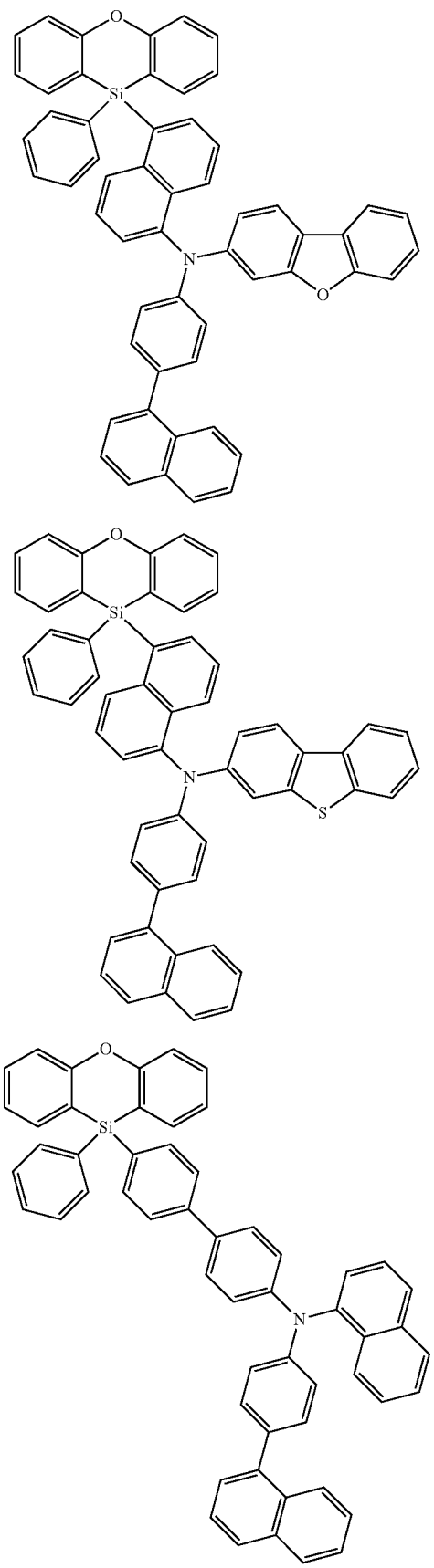
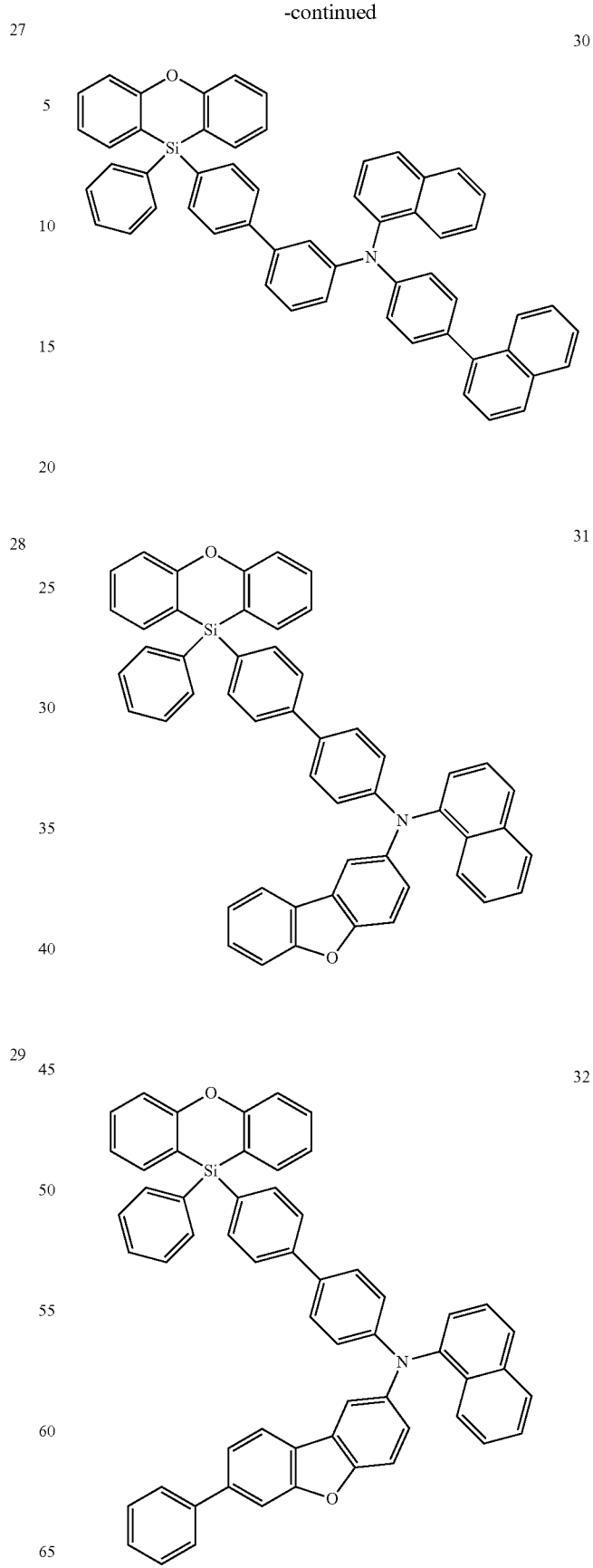

-continued

33

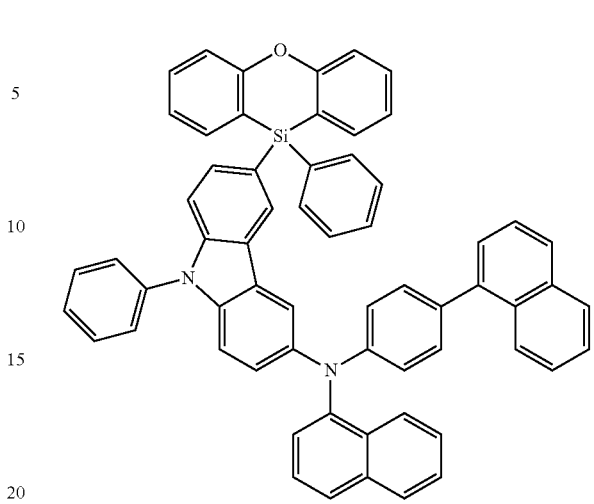

-continued

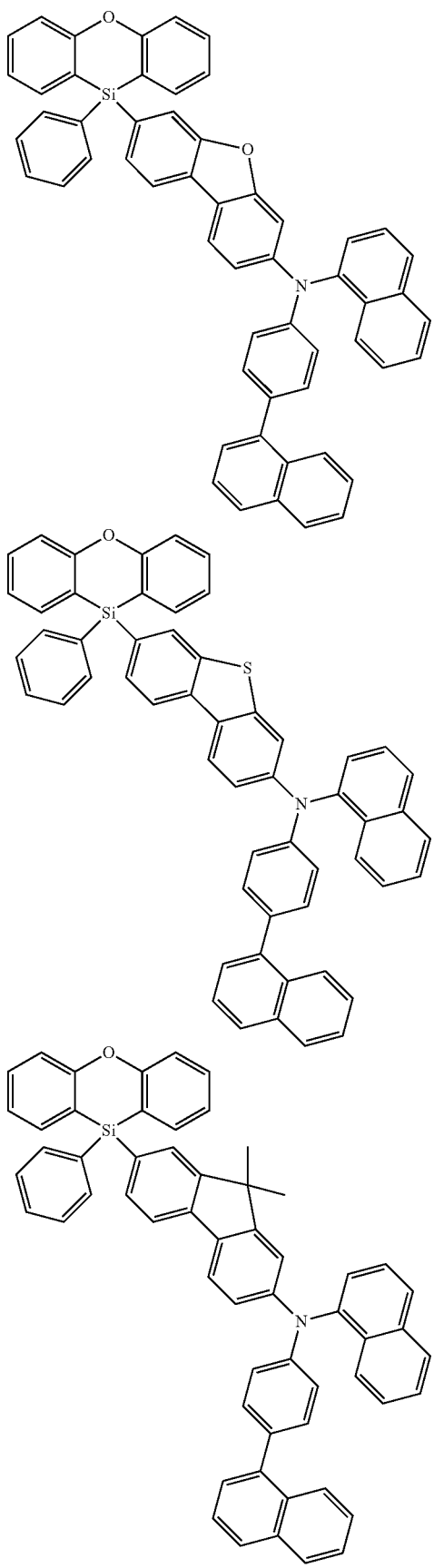

The heterocyclic compound represented by Formula 1 may be used as a material for an organic electroluminescence device. For example, the heterocyclic compound represented by Formula 1 may be used as a hole transport material.

When the heterocyclic compound according to an embodiment of the present disclosure is applied to an organic electroluminescence device, the device may attain a high efficiency and/or long life effect.

Hereinafter, an organic electroluminescence device according to an embodiment will be explained. The explanation will be mainly given with features different from the heterocyclic compound according to an embodiment of the present disclosure, and unexplained parts will follow the above-description on the heterocyclic compound according to an embodiment of the present disclosure.

An organic electroluminescence device according to an embodiment of the present disclosure may include the above-mentioned heterocyclic compound.

Figure 2:
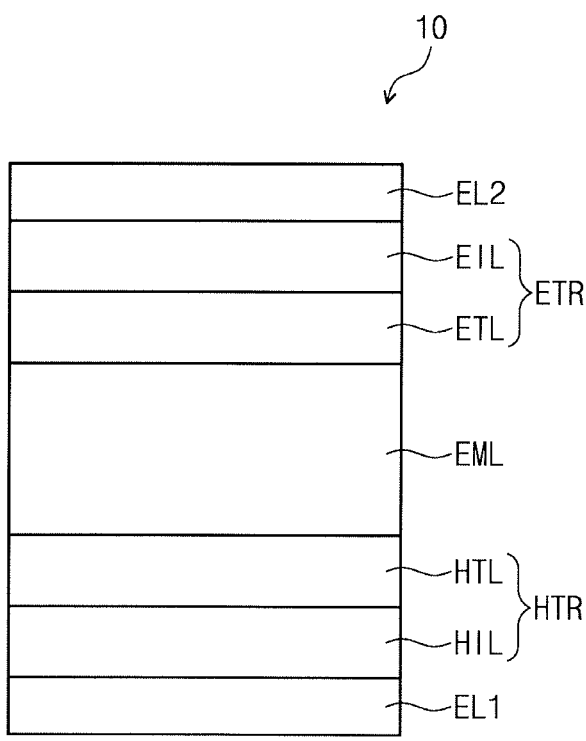
FIG. 2 illustrates a schematic cross-sectional view of an organic electroluminescence device according to an embodiment of the present disclosure.

FIG. 1 illustrates a schematic cross-sectional view of an organic electroluminescence device according to an embodiment of the present disclosure. FIG. 2 illustrates a schematic cross-sectional view of an organic electroluminescence device according to an embodiment of the present disclosure.

Referring to FIGS. 1 and 2, an organic electroluminescence device 10 according to an embodiment of the present disclosure may include, e.g., a first electrode EL1, a hole transport region HTR, an emission layer EML, an electron transport region ETR, and a second electrode EL2.

The first electrode EL1 has conductivity. The first electrode EL1 may be a pixel electrode or an anode. The first electrode EL1 may be a transmissive electrode, a transflective electrode, or a reflective electrode. In case the first electrode EL1 is the transmissive electrode, the first electrode EL1 may include a transparent metal oxide, e.g., indium tin oxide (ITO), indium zinc oxide (IZO), zinc oxide (ZnO), or indium tin zinc oxide (ITZO). In case the first electrode EL1 is the transflective electrode or reflective electrode, the first electrode EL1 may include, e.g., Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). In an implementation, the first electrode EL1 may have a structure including a plurality of layers including a reflective layer or transflective layer formed using the above materials, and a transparent conductive layer formed using ITO, IZO, ZnO, or ITZO.

The thickness of the first electrode EL1 may be from about 1,000 Å to about 10,000 Å, e.g., from about 1,000 Å to about 3,000 Å.

The hole transport region HTR may be disposed on the first electrode EL1. The hole transport region HTR may include at least one of a hole injection layer HIL, a hole transport layer HTL, a hole buffer layer, or an electron blocking layer. The thickness of the hole transport region HTR may be, e.g., from about 1,000 Å to about 1,500 Å.

Hereinafter, a case where the heterocyclic compound according to an embodiment of the present disclosure is included in a hole transport region HTR, will be explained. In an implementation, the heterocyclic compound according to an embodiment of the present disclosure may be included in at least one organic layer provided between the first electrode EL1 and the second electrode EL2. For example, the heterocyclic compound according to an embodiment of the present disclosure may be included in the emission layer EML.

The hole transport region HTR may include the heterocyclic compound according to an embodiment of the present disclosure. For example, the hole transport region HTR may include the heterocyclic compound represented by the following Formula 1:

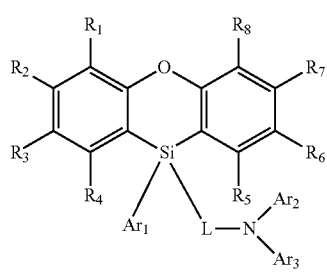

[Formula 1]

In Formula 1, particular explanation on $R_1$ to $R_8$, $Ar_1$ to $Ar_3$, and L is the same as described above, and will be omitted. In an implementation, the compound represented by Formula 1 included in the hole transport region HTR may be a monoamine compound.

The hole transport region HTR may have a single layer formed using a single material, a single layer formed using a plurality of different materials, or a multilayer structure including a plurality of layers formed using a plurality of different materials.

For example, the hole transport region HTR may have a single layer structure of a hole injection layer HIL or a hole transport layer HTL, or may have a single layer structure formed using a hole injection material and a hole transport material. In an implementation, the hole transport region HTR may have, e.g., a single layer structure formed using a plurality of different materials, or a laminated structure of hole injection layer HIL/hole transport layer HTL, hole injection layer HIL/hole transport layer HTL/hole buffer layer, hole injection layer HIL/hole buffer layer, hole transport layer HTL/hole buffer layer, or hole injection layer HIL/hole transport layer HTL/electron blocking layer, laminated in order from the first electrode ELL.

In an implementation, when the hole transport region HTR includes a structure of hole injection layer HIL/hole transport layer HTL, the heterocyclic compound according to an embodiment of the present disclosure may be included in the hole transport layer HTL. In an implementation, when the hole transport region HTR has a multilayer structure, the heterocyclic compound according to an embodiment of the present disclosure may be included in a layer contacting with the emission layer EML, and may be included in each of the layer contacting with the emission layer EML and the hole transport layer HTL. In an implementation, when the hole transport layer HTL includes the heterocyclic compound according to an embodiment of the present disclosure, the hole transport layer HTL may include one or more heterocyclic compound according to an embodiment of the present disclosure.

The hole transport region HTR may be formed using various methods such as a vacuum deposition method, a spin coating method, a cast method, a Langmuir-Blodgett (LB) method, an inkjet printing method, a laser printing method, and a laser induced thermal imaging (LITI) method.

The hole injection layer HIL may include, e.g., a phthalocyanine compound such as copper phthalocyanine; N,N'-diphenyl-N,N'-bis-[4-(phenyl-m-tolyl-amino)-phenyl]-biphenyl-4,4'-diamine (DNTPD), 4,4',4''-tris(3-methylphenylphenylamino)triphenylamine (m-MTDATA), 4,4',4''-tris(N,N-diphenylamino)triphenylamine (TDATA), 4,4',4''-tris{N-(2-naphthyl)-N-phenylamino}-triphenylamine (2-TNATA), poly(3,4-ethylenedioxythiophene)/poly(4-styrenesulfonate) (PEDOT/PSS), polyaniline/dodecylbenzenesulfonic acid (PANI/DBSA), polyaniline/camphor sulfonic acid (PANI/CSA), polyaniline/poly(4-styrenesulfonate) (PANI/PSS), N,N'-di(naphthalen-1-yl)-N,N'-diphenyl-benzidine (NPB), triphenylamine-containing polyether ketone (TPAPEK), 4-isopropyl-4'-methyldiphenyliodonium tetrakis(pentafluorophenyl)borate, dipyrazino[2,3-f: 2',3'-h]quinoxaline-2,3,6,7,10,11-hexacarbonitrile (HAT-CN), etc.

When the hole transport layer HTL includes the heterocyclic compound according to an embodiment of the present disclosure, it may further include an additional material in addition to the heterocyclic compound according to an embodiment of the present disclosure. For example, the hole transport layer HTL may further include carbazole derivatives such as N-phenyl carbazole and polyvinyl carbazole, fluorine-based derivatives. N,N'-bis(3-methylphenyl)-N,N'-diphenyl-[1,1-biphenyl]-4,4'-diamine (TPD), triphenylamine-based derivatives such as 4,4',4''-tris(N-carbazolyl)triphenylamine (TCTA), N,N-di(1-naphthalen-1-yl)-N,N'-diphenyl-benzidine (NPB), 4,4'-cyclohexylidene bis[N,N-bis(4-methylphenyl)benzenamine] (TAPC), 4,4'-bis[N,N'-(3-tolyl)amino]-3,3'-dimethylbiphenyl (HMTPD), etc.

The thickness of the hole transport region HTR may be from about 100 Å to about 10,000 Å, e.g., from about 100 Å to about 1,000 Å. In case the hole transport region HTR includes both of the hole injection layer HIL and the hole transport layer HTL, the thickness of the hole injection layer HIL may be from about 100 Å to about 10,000 Å, e.g., from about 100 Å to about 1,000 Å, and the thickness of the hole transport layer HTL may be from about 30 Å to about 1,000 Å. In case the thicknesses of the hole transport region HTR, the hole injection layer HIL and the hole transport layer HTL satisfy the above-described ranges, satisfactory hole transport properties may be obtained without the substantial increase of a driving voltage.

The hole transport region HTR may further include a charge generating material in addition to the above-described materials to improve conductivity. The charge generating material may be dispersed in the hole transport region HTR uniformly or non-uniformly. The charge generating material may be, e.g., a p-dopant. The p-dopant may include, e.g., quinone derivatives, metal oxides, or cyano group-containing compounds. Examples of the p-dopant may include quinone derivatives such as tetracyanoquinodimethane (TCNQ), and 2,3,5,6-tetrafluoro-tetracyanoquinodimethane (F4-TCNQ), metal oxides such as tungsten oxide and molybdenum oxide.

As described above, the hole transport region HTR may further include at least one of a hole buffer layer or an electron blocking layer in addition to the hole injection layer HIL and the hole transport layer HTL. The hole buffer layer may help compensate an optical resonance distance according to the wavelength of light emitted from the emission layer EML and increase light emission efficiency. Materials included in the hole transport region HTR may be used as materials included in the hole buffer layer. The electron blocking layer is a layer preventing electron injection from the electron transport region ETR into the hole transport region HTR.

The emission layer EML may be disposed on the hole transport region HTR. The emission layer EML emits fluorescent or phosphorescent light, and the thickness of the emission layer EML may be, e.g., from about 100 Å to about 600 Å.

The emission layer EML may have a single layer formed using a single material, a single layer formed using a plurality of different materials, or a multilayer structure having a plurality of layers formed using a plurality of different materials.

The material of the emission layer EML may include a suitable emission material, e.g., fluoranthene derivatives, pyrene derivatives, arylacetylene derivatives, fluorene derivatives, perylene derivatives, chrysene derivatives, anthracene derivatives, benzoanthracene derivatives, triphenylene derivatives, or the like. For example, pyrene derivatives, perylene derivatives, or anthracene derivatives. For example, as the host material of the emission layer EML, anthracene derivatives represented by Formula 4 may be used.

[Formula 4]

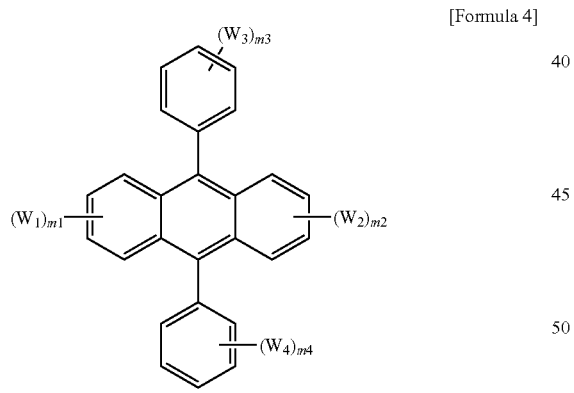

In Formula 4, $W_1$ to $W_4$ may each independently be or include, e.g., a hydrogen atom, a deuterium atom, a halogen atom, a substituted or unsubstituted silyl group, a substituted or unsubstituted alkyl group having 1 to 20 carbon atoms, a substituted or unsubstituted aryl group having 6 to 30 ring carbon atoms, or a substituted or unsubstituted heteroaryl group having 2 to 30 ring carbon atoms, m1 and m2 may each independently be, e.g., an integer of 0 to 4, and m3 and m4 may each independently be, e.g., an integer of 0 to 5. In an implementation, $W_3$ and $W_4$ may be each independently combined with an adjacent group to form a saturated or unsaturated ring.

In case m1 is 2 or more, a plurality of $W_1$ may be the same or different from each other. In case m2 is 2 or more, a plurality of $W_2$ may be the same or different from each other. In case m3 is 2 or more, a plurality of $W_3$ may be the same or different from each other. In case m4 is 2 or more, a plurality of $W_4$, may be the same or different from each other.

In an implementation, the compound represented by Formula 4 may include. e.g., a compound represented by one of the following formulae a-1 to a-12.

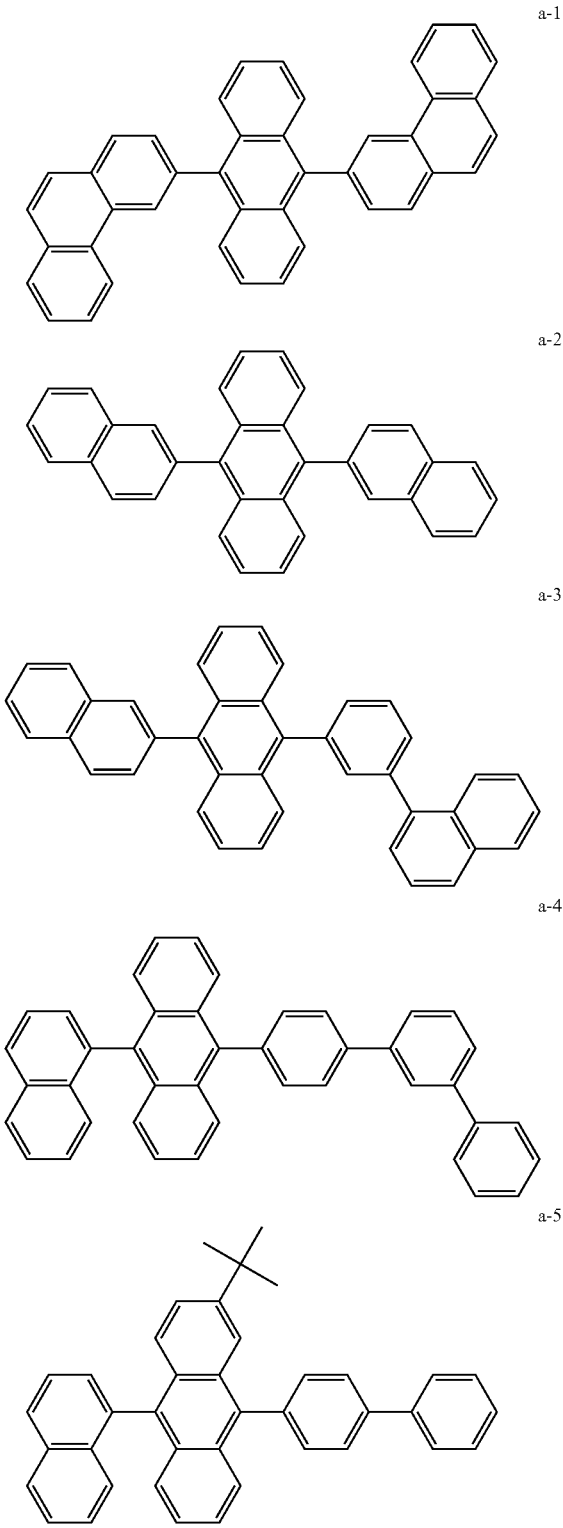

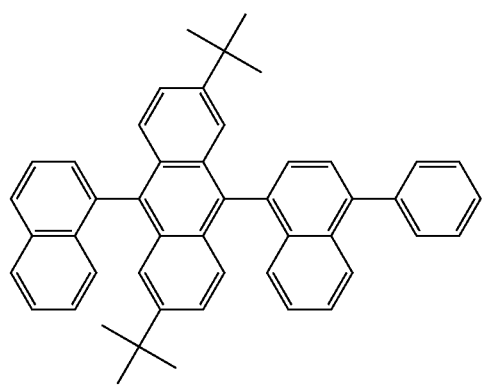

a-6

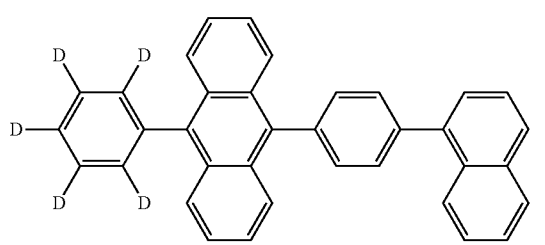

a-7

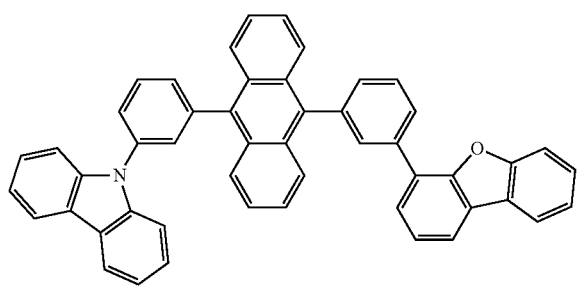

a-8

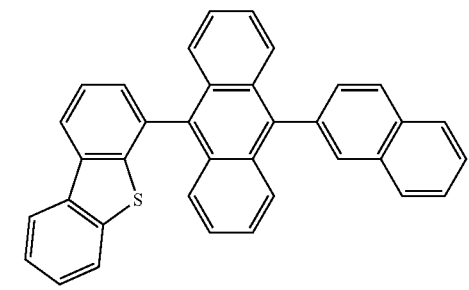

a-9

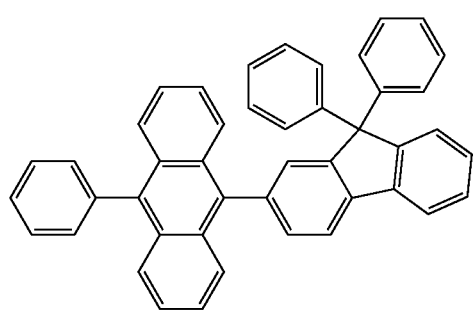

a-10

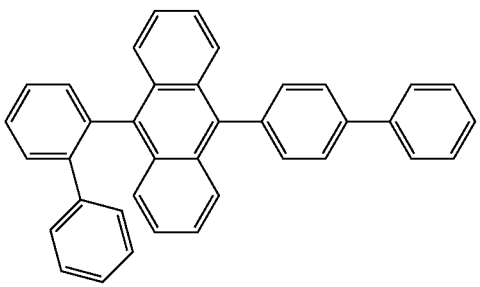

a-11

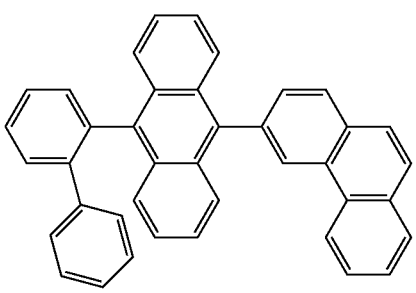

a-12

The emission layer EML may include a fluorescent material including, e.g., spiro-DPVBi, 2,2',7,7'-tetrakis(biphenyl-4-yl)-9,9'-spirobifluorene(spiro-sexiphenyl) (spiro-6P), distyryl-benzene (DSB), distyryl-arylene (DSA), polyfluorene (PFO)-based polymer and poly(p-phenylene vinylene) (PPV)-based polymer.

The emission layer EML may further include a suitable dopant. The dopant may include, e.g., styryl derivatives (for example, 1,4-bis[2-(3-N-ethylcarbazolyl)vinyl]benzene (BCzVB), 4-(di-p-tolylamino)-4'-[(di-p-tolylamino)styryl] stilbene (DPAVB), N-(4-((E)-2-(6-((E)-4-(diphenylamino) styryl)naphthalen-2-yl)vinyl)phenyl)-N-phenylbenzenamine (N-BDAVBi)), perylene and the derivatives thereof (for example, 2,5,8,11-tetra-t-butylperylene (TBPe)), pyrene and the derivatives thereof (for example, 1,1-dipyrene, 1,4-dipyrenylbenzene, 1,4-bis(N,N-diphenylamino)pyrene), 2,5, 8,11-tetra-t-butylperylene (TBP), 1,3,5-tris(N-phenylbenzimidazol-2-yl)benzene (TPBi), bis[2-(4,6-difluorophenyl) pyridinato-$C^2$,N](picolinato) (Flrpic), etc.

The emission layer EML may include, e.g., tris(8-hydroxyquinolino)aluminum (Alq3), 4,4'-bis(N-carbazolyl)-1, 1'-biphenyl (CBP), poly(N-vinylcarbazole) (PVK), 9,10-di (naphthalen-2-yl)anthracene (ADN), 4,4',4"-tris(carbazol-9-yl)-triphenylamine (TCTA), 1,3,5-tris(N-phenylbenzimidazol-2-yl)benzene (TPBi), 3-tert-butyl-9, 10-di(naphth-2-yl)anthracene (TBADN), distyrylarylene (DSA), 4,4'-bis(9-carbazolyl)-2,2'-dimethyl-biphenyl (CDBP), 2-methyl-9,10-bis(naphthalen-2-yl)anthracene (MADN), bis[2-(diphenylphosphino)phenyl]ether oxide (DPEPO), hexaphenyl cyclotriphosphazene (CP1), 1,4-bis (triphenylsilyl)benzene (UGH2), hexaphenylcyclotrisiloxane (DPSiO$_3$), octaphenylcyclotetrasiloxane (DPSiO$_4$), 1,3-Bis(N-carbazolyl)benzene (mCP), 2,8-bis (diphenylphosphoryl)dibenzofuran (PPF), etc.

In an implementation, the emission layer EML may include, e.g., a layer that emits blue light. In an implementation, the emission layer EML may include a layer that emits green light and/or a layer which emits red light.

The electron transport region ETR may be provided on the emission layer EML. In an implementation, the electron transport region ETR may include at least one of a hole blocking layer, an electron transport layer ETL or an electron injection layer EIL.

The electron transport region ETR may have a single layer formed using a single material, a single layer formed using a plurality of different materials, or a multilayer structure having a plurality of layers formed using a plurality of different materials.

For example, the electron transport region ETR may have a single layer structure of the electron injection layer EIL or the electron transport layer ETL, or a single layer structure formed using an electron injection material and an electron transport material. In an implementation, the electron transport region ETR may have, e.g., a single layer structure having a plurality of different materials, or a laminated structure of electron transport layer ETL/electron injection layer EIL, or hole blocking layer/electron transport layer ETL/electron injection layer EIL, laminated in order from the emission layer EML. The thickness of the electron transport region ETR may be, e.g., from about 100 Å to about 1,500 Å.

The electron transport region ETR may be formed using various methods such as a vacuum deposition method, a spin coating method, a cast method, a Langmuir-Blodgett (LB) method, an inkjet printing method, a laser printing method, and a laser induced thermal imaging (LITI) method.

When the electron transport region ETR includes the electron transport layer ETL, the electron transport region ETR may include, e.g., tris(8-hydroxyquinolinato)aluminum (Alq3), 1,3,5-tri[(3-pyridyl)-phen-3-yl]benzene, 2,4,6-tris(3'-(pyridin-3-yl)biphenyl-3-yl)-1,3,5-triazine, 2-(4-(N-phenylbenzoimidazolyl-1-ylphenyl)-9,10-dinaphthylanthracene, 1,3,5-tri(1-phenyl-1H-benzo[d]imidazol-2-yl)phenyl (TPBi), 2,9-dimethyl-4,7-diphenyl-1,10-phenanthroline (BCP), 4,7-diphenyl-1,10-phenanthroline (Bphen), 3-(4-biphenylyl)-4-phenyl-5-tert-butylphenyl-1,2,4-triazole (TAZ), 4-(naphthalen-1-yl)-3,5-diphenyl-4H-1,2,4-triazole (NTAZ), 2-(4-biphenylyl)-5-(4-tert-butylphenyl)-1,3,4-oxadiazole (tBu-PBD), bis(2-methyl-8-quinolinolato-N1,08)-(1,1'-biphenyl-4-olato) aluminum (BAlq), berylliumbis(benzoquinolin-10-olate (Bebq$_2$), 9,10-di(naphthalene-2-yl)anthracene (ADN), or a mixture thereof. The thickness of the electron transport layer ETL may be from about 100 Å to about 1,000 Å, e.g., from about 150 Å to about 500 Å. If the thickness of the electron transport layer ETL satisfies the above-described range, satisfactory electron transport properties may be obtained without substantial increase of a driving voltage.

When the electron transport region ETR includes the electron injection layer EIL, the electron transport region ETR may include, e.g., LiF, lithium quinolate (LiQ), Li$_2$O, BaO, NaCl, CsF, a metal in lanthanoids such as Yb, or metal halides such as RbCl and RbI, without. The electron injection layer EIL also may be formed using a mixture material of an electron transport material and an insulating organo metal salt. The organo metal salt may be a material having an energy band gap of about 4 eV or more. For example, the organo metal salt may include a metal acetate, a metal benzoate, a metal acetoacetate, a metal acetylacetonate, or a metal stearate. The thickness of the electron injection layer EIL may be from about 1 Å to about 100 Å, e.g., from about 3 Å to about 90 Å. In case the thickness of the electron injection layer EIL satisfies the above described range, satisfactory electron injection properties may be obtained without inducing the substantial increase of a driving voltage.

The electron transport region ETR may include a hole blocking layer, as described above. In an implementation, the hole blocking layer may include, e.g., at least one of 2,9-dimethyl-4,7-diphenyl-1,10-phenanthroline (BCP), or 4,7-diphenyl-1,10-phenanthroline (Bphen).

The second electrode EL2 may be disposed on the electron transport region ETR. The second electrode EL2 may be a common electrode or a cathode. The second electrode EL2 may be a transmissive electrode, a transflective electrode or a reflective electrode. In case the second electrode EL2 is the transmissive electrode, the second electrode EL2 may be formed using transparent metal oxides, e.g., ITO, IZO, ZnO, ITZO, etc.

In case the second electrode EL2 is the transflective electrode or the reflective electrode, the second electrode EL2 may include, e.g., Ag, Mg, Cu, Al, Pt, Pd, Au, Ni, Nd, Ir, Cr, Li, Ca, LiF/Ca, LiF/Al, Mo, Ti, a compound thereof, or a mixture thereof (for example, a mixture of Ag and Mg). The second electrode EL2 may have a multilayered structure including a reflective layer or a transflective layer formed using the above-described materials and a transparent conductive layer formed using ITO, IZO, ZnO, ITZO, etc.

The thickness of the second electrode EL2 may be from about 700 Å to about 10,000 Å, e.g., from about 700 Å to about 2,000 Å.

In an implementation, the second electrode EL2 may be connected with an auxiliary electrode. In case the second electrode EL2 is connected with the auxiliary electrode, the resistance of the second electrode EL2 may decrease.

In the organic electroluminescence device 10, according to the application of a voltage to each of the first electrode EL1 and second electrode EL2, holes injected from the first electrode EL1 may move via the hole transport region HTR to the emission layer EML, and electrons injected from the second electrode EL2 may move via the electron transport region ETR to the emission layer EML. The electrons and the holes are recombined in the emission layer EML to generate excitons, and light may be emitted via the transition of the excitons from an excited state to a ground state.

The organic electroluminescence device according to an embodiment of the present disclosure includes the heterocyclic compound represented by Formula 1 in the hole transport region, thereby securing a high efficiency and/or long life.

The following Examples and Comparative Examples are provided in order to highlight characteristics of one or more embodiments, but it will be understood that the Examples and Comparative Examples are not to be construed as limiting the scope of the embodiments, nor are the Comparative Examples to be construed as being outside the scope of the embodiments. Further, it will be understood that the embodiments are not limited to the particular details described in the Examples and Comparative Examples.

SYNTHESIS EXAMPLES

The heterocyclic compounds according to an embodiment of the present disclosure may be synthesized, e.g., as follows.

1. Synthesis of Compound 1

Compound 1 was synthesized by the following reaction.

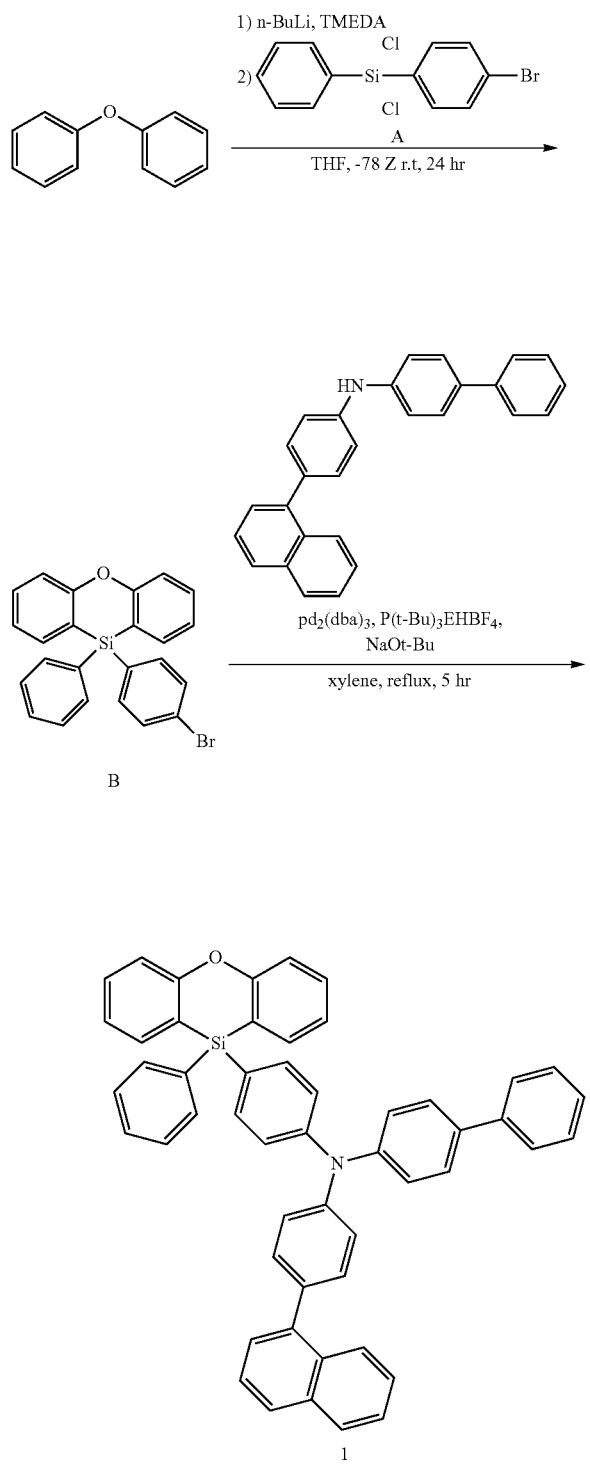

(Synthesis of Compound A)

Under an argon (Ar) atmosphere, 28.83 g of p-dibromobenzene and 240 mL of dehydrated THF were injected to a 1 L three neck flask, and 75 mL of 1.6 M n-BuLi was added thereto dropwise at about −78° C. After stirring for about 2 hours, 25.38 g of trichlorosilane dissolved in 60 mL of dehydrated THF was added thereto dropwise at about −78° C. After stirring for about 1 hour, the temperature was elevated to ambient temperature, and then the reactant was stirred for about 16 hours. After adding water to the reaction solution, the mixture was extracted with ethyl acetate. An organic layer was separated and taken, and solvents were evaporated. The crude product was purified by silica gel column chromatography (a mixture of dichloromethane and hexane) to obtain 18.23 g (yield 45%) of Compound A as a white solid.

(Synthesis of Compound B)

Under an argon (Ar) atmosphere, 13.39 g of TMEDA and 80 mL of dehydrated THF were injected to a 200 mL three neck flask, and 37.8 mL of 1.6 M n-BuLi was added thereto dropwise at about 0° C. Under an argon (Ar) atmosphere, 9.36 g of diphenyl ether was dissolved in 150 mL of dehydrated THF in a 500 mL three neck flask, and the above-mentioned reaction solution was added thereto dropwise at about −78° C. After stirring at about −78° C. for about 2 hours, 18.2 g of Compound A dissolved in 150 mL of dehydrated THF was added thereto dropwise at about −78° C. After stirring at about −78° C. for about 2 hours, the reactant was returned to ambient temperature, and then stirred for about 24 hours. After the reactant was extracted with ethyl acetate, an organic layer was separated and taken, and solvents were evaporated. The crude product was purified by silica gel column chromatography (a mixture of dichloromethane and hexane) to obtain 8.26 g (yield 35%) of Compound B as a white solid;

(Synthesis of Compound 1)

Under an argon (Ar) atmosphere, 8.26 g of Compound B, 7.15 g of biphenylnaphthylphenylamine, 0.35 g of $Pd_2(dba)_3$, 0.89 g of $P(t-Bu)_3 \cdot HBF_4$, 2.59 g of sodium t-butoxide and 77 mL of dehydrated xylene were injected to a 300 mL three neck flask and the mixture was heated and stirred for about 5 hours. After cooling in the air, water was added thereto and the mixture was extracted with toluene. An organic layer was separated and taken, and solvents were evaporated. The crude product was purified by silica gel column chromatography (using a mixture of dichloromethane and hexane) and recrystallized by a mixture of toluene/hexane to obtain 11.55 g (yield 60%) of Compound 1 as a white solid.

The molecular weight of Compound 1 measured by FAB-MS was 719.

2. Synthesis of Compound 29

Compound 29 was synthesized by conducting the same synthetic method of Compound 1 except for using 4,4'-dibromobiphenyl instead of p-dibromobenzene and biphenylnaphtylphenylamine instead of 4-bromophenyl.

The molecular weight of Compound 29 measured by FAB-MS was 769.

3. Synthesis of Compound 3

Under an argon (Ar) atmosphere, 7.65 g of Compound B, 5.98 g of N-([1,1'-biphenyl]-4-yl)dibenz[b,d]furan-3-amine, 0.33 g of $Pd_2(dba)_3$, 40.41 g of $P(t-Bu)_3 \cdot HBF_4$, 2.40 g of sodium t-butoxide and 71 mL of dehydrated xylene were injected to a 300 mL three neck flask and the mixture was heated and stirred for about 4 hours. After cooling in the air, water was added thereto and the mixture was extracted with toluene. An organic layer was separated and taken, and solvents were evaporated. The crude product was purified by silica gel column chromatography (using a mixture of dichloromethane and hexane) and recrystallized by a mixture of toluene/hexane to obtain 11.16 g (yield 75%) of Compound 3 as a white solid.

The molecular weight of Compound 3 measured by FAB-MS was 683.

4. Synthesis of Compound 25

(Synthesis of Compound C)

Compound C was synthesized by conducting the same synthetic method of Compound A except for using 1,5'-dibromonaphthalene instead of p-dibromobenzene.

(Synthesis of Compound D)

Compound D was synthesized by conducting the same synthetic method of Compound B except for using Compound C instead of Compound A.

(Synthesis of Compound 25)

Compound 25 was synthesized by conducting the same synthetic method of Compound 1 except for using Compound D instead of Compound B.

The molecular weight of Compound 25 measured by FAB-MS was 769.

In Synthesis Examples 1 to 4, the molecular weight of compounds was measured by FAB-MS using JMS-700V (JEOL Korea Ltd.).

(Device Manufacturing Examples)

Organic electroluminescence devices of Examples 1 to 4 were manufactured by using the above Compounds 1, 29, 3, and 25 as hole transport layer materials.

[Example Compounds]

Compound 1

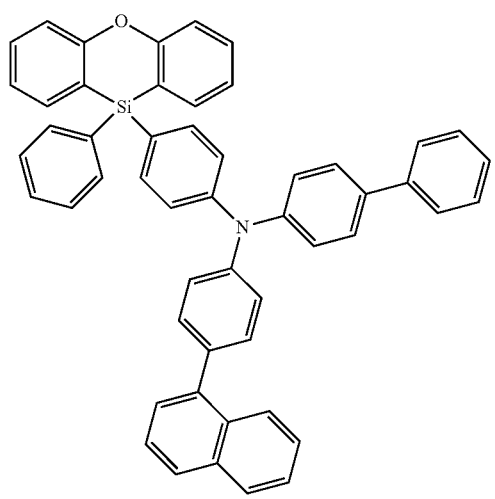

Compound 29

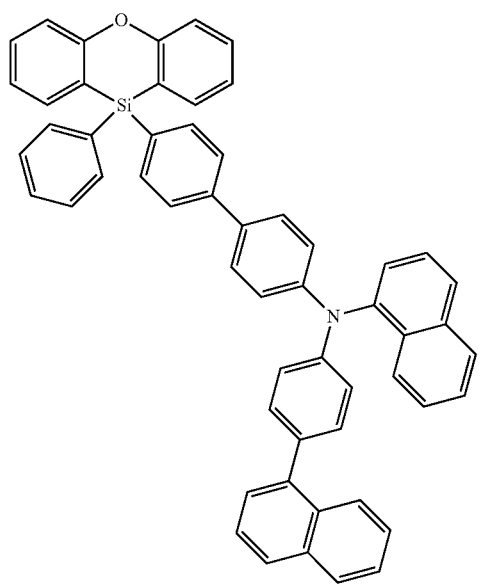

Compound 3

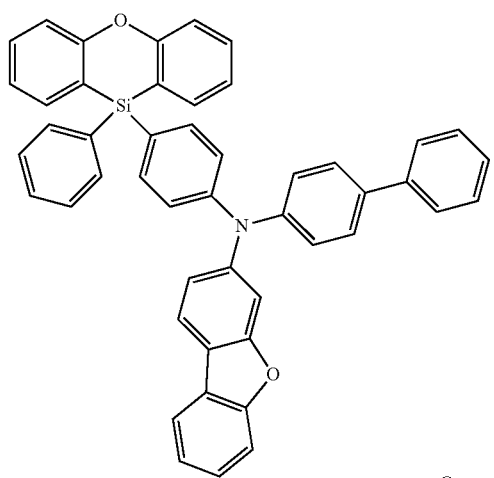

Compound 4

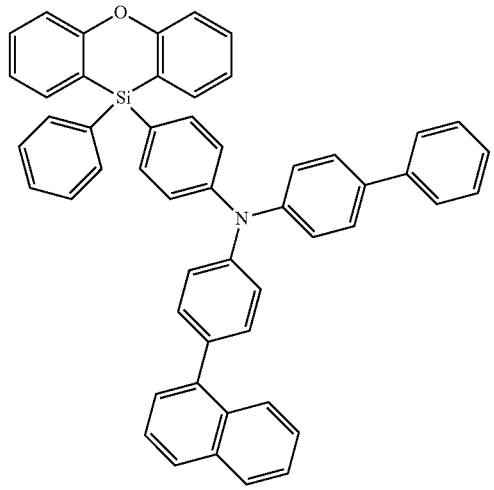

Organic electroluminescent devices of Comparative Examples 1 to 4 were manufactured by using the following Comparative Compounds c-1 to c-4 as hole transport layer materials.

[Comparative Compounds]

Comparative Compound c-1

Comparative Compound c-2

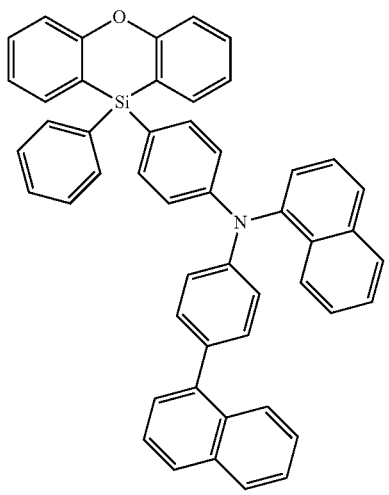

Comparative Compound c-3

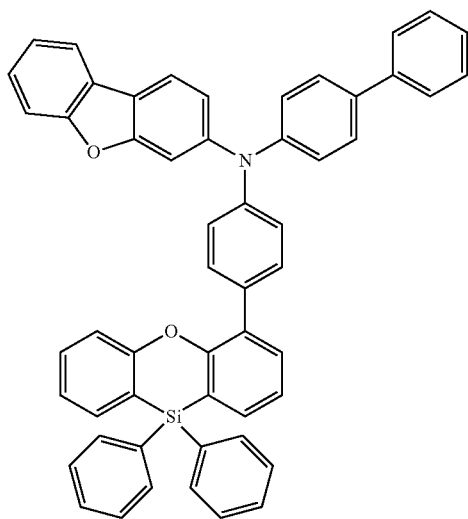

Comparative Compound c-4

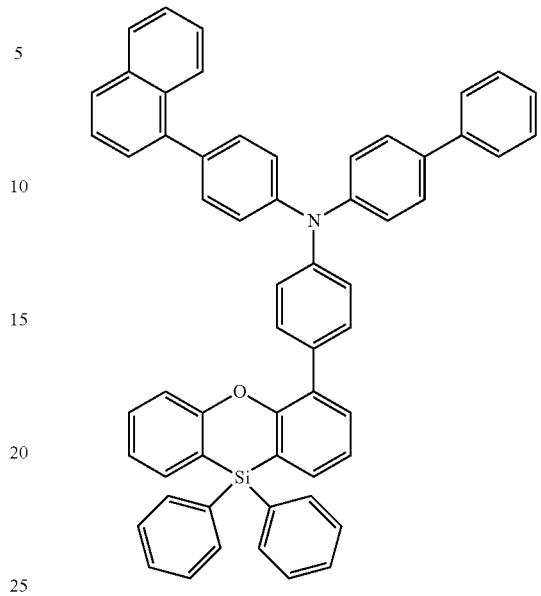

The organic electroluminescence devices according to Examples 1 to 4 and Comparative Examples 1 to 4 were manufactured by forming a first electrode using ITO to a thickness of about 150 nm, a hole injection layer using TNATA to a thickness of about 60 nm, a hole transport layer using the example compounds or the comparative compounds to a thickness of about 30 nm, an emission layer using 9,10-di(naphthalen-2-yl)anthracene (ADN) doped with 3% 2,5,8,11-tetra-t-butylperylene (TBP) to a thickness of about 25 nm, an electron transport layer using $Alq_3$ to a thickness of about 25 nm, an electron injection layer using LiF to a thickness of about 1 nm, and a second electrode using Al to a thickness of about 100 nm. Each layer was formed by a vacuum deposition method.

The current density, driving voltage, emission efficiency, and life of the manufactured organic electroluminescence devices were evaluated. The current density, driving voltage, emission efficiency, and life were measured in a dark room by using Source Meter, 2400 Series (Keithley Instruments, Inc.), color brightness measurement system CS-200 (Konica Minolta Holdings, Inc.), and National Instrument (NI) PC Program LabVIEW 8.2 for measurement (National Instruments Corporation, Japan), respectively. Evaluation results are shown in Table 1 below.

TABLE 1

| Device manufacturing example | Hole transport layer material | Current density (mA/cm$^2$) | Driving voltage (V) | Emission efficiency (cd/A) | Life LT50 (h) |
|---|---|---|---|---|---|
| Example 1 | Example Compound 1 | 10 | 5.5 | 6.3 | 2,150 |
| Example 2 | Example Compound 29 | 10 | 5.7 | 6.0 | 2,000 |
| Example 3 | Example Compound 3 | 10 | 5.5 | 6.1 | 2,300 |
| Example 4 | Example Compound 25 | 10 | 5.8 | 6.0 | 1,950 |
| Comparative Example 1 | Comparative Compound c-1 | 10 | 6.5 | 5.3 | 1,450 |
| Comparative Example 2 | Comparative Compound c-2 | 10 | 6.6 | 5.5 | 1,350 |
| Comparative Example 3 | Comparative Compound c-3 | 10 | 6.5 | 5.8 | 1,500 |
| Comparative Example 4 | Comparative Compound c-4 | 10 | 6.5 | 5.2 | 1,300 |

Referring to the results in Table 1, it may be seen that the heterocyclic compounds of the Examples had an effect of improving emission efficiency of the device. In addition, effects of extended device life and decreased driving voltage were also observed.

Comparing Example 1 with Comparative Example 1, and Example 2 with Comparative Example 2, it may be seen that hole transport materials having a core structure with oxygen and silicon used in the Examples exhibited an effect of extended device life and high efficiency, compared with those having no silicon used in Comparative Examples.

Comparing Example 1 with Comparative Examples 3 and 4, it may be seen that a hole transport material with aryl amine group substituted at silicon atom used in Example 1 exhibited an effect of extended device life and high efficiency compared with those with aryl amine group substituted at benzene ring instead of silicon atom used in the Comparative Examples.

The embodiments may provide a heterocyclic compound that may be used as a hole transport material and an organic electroluminescence device including the same in a hole transport region.

The heterocyclic compound according to an embodiment of the present disclosure may exhibit excellent emission efficiency.

The organic electroluminescence device including the heterocyclic compound according to an embodiment of the present disclosure may attain high emission efficiency.

The organic electroluminescence device including the heterocyclic compound according to an embodiment of the present disclosure may attain a long life.

Example embodiments have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following claims.

What is claimed is:

1. A heterocyclic compound represented by the following Formula 1:

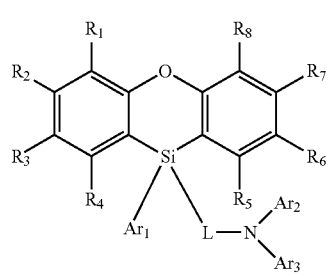

[Formula 1]

wherein, in Formula 1, $R_1$ to $R_8$ are each independently a hydrogen atom, a deuterium atom, a halogen atom, a substituted or unsubstituted silyl group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aryl group having 6 to 30 ring carbon atoms, or a substituted or unsubstituted heteroaryl group having 2 to 30 ring carbon atoms, $R_1$ to $R_8$ being separate or forming a ring by combining adjacent groups with each other, $Ar_1$ to $Ar_3$ are each independently a substituted or unsubstituted aryl group having 6 to 30 ring carbon atoms or a substituted or unsubstituted heteroaryl group having 2 to 30 ring carbon atoms, and L is a direct linkage, a substituted or unsubstituted arylene group having 6 to 30 ring carbon atoms, or a substituted or unsubstituted heteroarylene group having 2 to 30 ring carbon atoms.

2. The heterocyclic compound as claimed in claim 1, wherein $Ar_1$ is a substituted or unsubstituted aryl group having 6 to 30 ring carbon atoms.

3. The heterocyclic compound as claimed in claim 1, wherein $Ar_1$ is a substituted or unsubstituted phenyl group or a substituted or unsubstituted biphenyl group.

4. The heterocyclic compound as claimed in claim 1, wherein L is a group represented by one of the following Formulae L-1 to L-4:

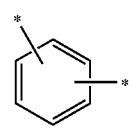

L-1

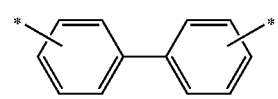

L-2

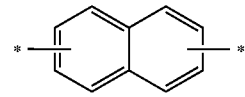

L-3

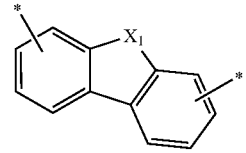

L-4 wherein, in Formula L-4, $X_1$ is O, S, $NR_9$ or $CR_{10}R_{11}$, and $R_9$ to $R_{11}$ are each independently a hydrogen atom, a deuterium atom, a halogen atom, a substituted or unsubstituted alkyl group having 1 to 30 carbon atoms, a substituted or unsubstituted aryl group having 6 to 30 ring carbon atoms, or a substituted or unsubstituted heteroaryl group having 2 to 30 ring carbon atoms.

5. The heterocyclic compound as claimed in claim 1, wherein at least one of $Ar_2$ or $Ar_3$ is a substituted or unsubstituted aryl group having 6 to 30 ring carbon atoms.

6. The heterocyclic compound as claimed in claim 1, wherein at least one of $Ar_2$ or $Ar_3$ is a group represented by the following Formula 2:

*-A-B    [Formula 2]

wherein, in Formula 2,

A is a substituted or unsubstituted phenylene group, and

B is a substituted or unsubstituted polycyclic aryl group having 6 to 30 ring carbon atoms.

7. The heterocyclic compound as claimed in claim 6, wherein the group represented by Formula 2 is a group represented by the following Formula 2-1:

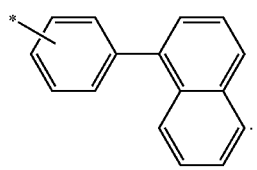

[Formula 2-1]

8. The heterocyclic compound as claimed in claim 1, wherein $Ar_2$ and $Ar_3$ are different from each other.

9. The heterocyclic compound as claimed in claim 1, wherein:

one of $Ar_2$ and $Ar_3$ is a substituted or unsubstituted aryl group having 6 to 30 ring carbon atoms, and the other of $Ar_2$ and $Ar_3$ is a substituted or unsubstituted aryl group having 6 to 30 ring carbon atoms or a group represented by the following Formula 3:

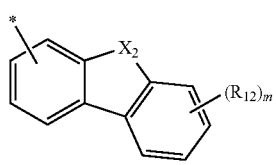

[Formula 3]

wherein, in Formula 3, $X_2$ is O or S, m is an integer of 1 to 4, and $R_{12}$ is a hydrogen atom, a deuterium atom, or a substituted or unsubstituted aryl group having 6 to 30 ring carbon atoms.

10. The heterocyclic compound as claimed in claim 9, wherein, in Formula 3, m is 0 or 1, and when m is 1, $R_{12}$ is a substituted or unsubstituted aryl group having 6 to 30 ring carbon atoms.

11. The heterocyclic compound as claimed in claim 1, wherein the heterocyclic compound represented by Formula 1 is a compound the following Compound Group 1:

[Compound Group 1]

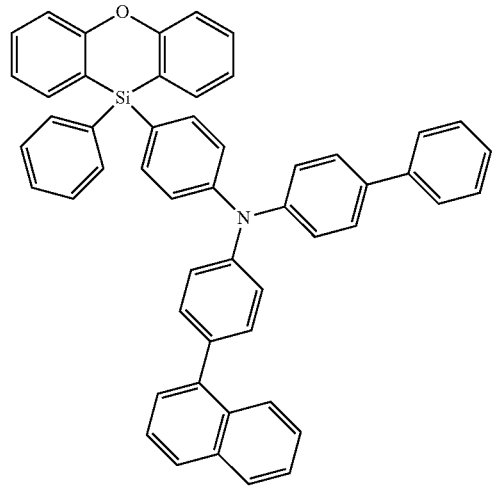

1

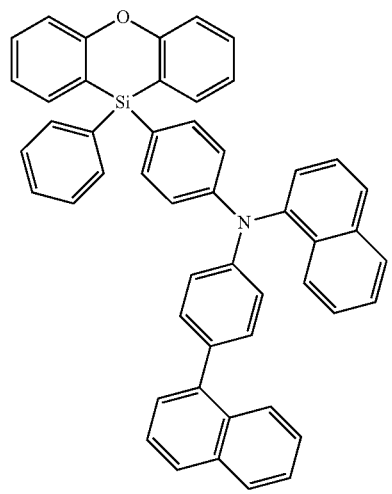

2

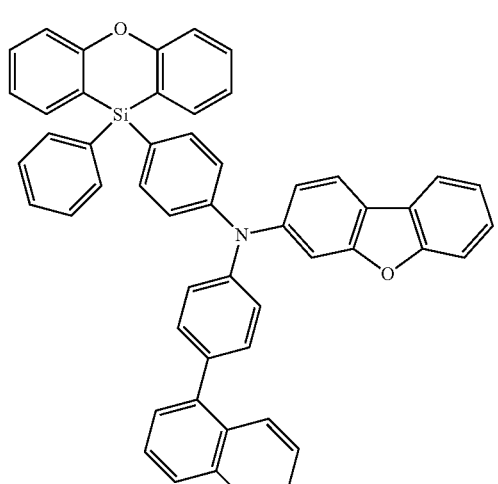

3

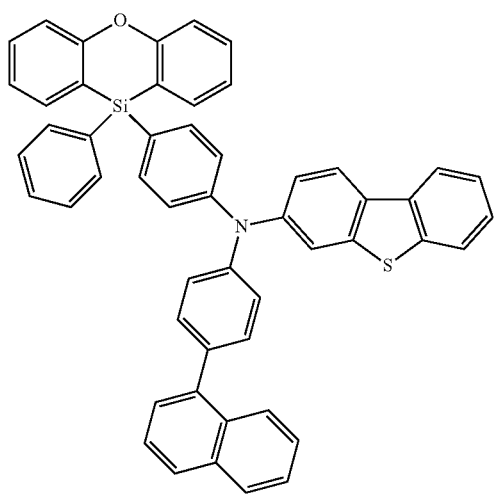
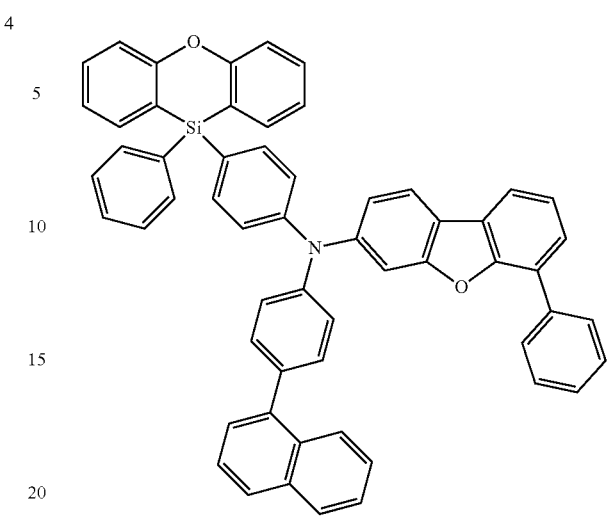
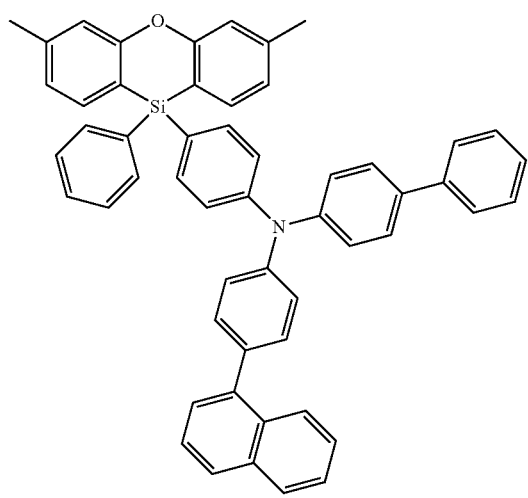
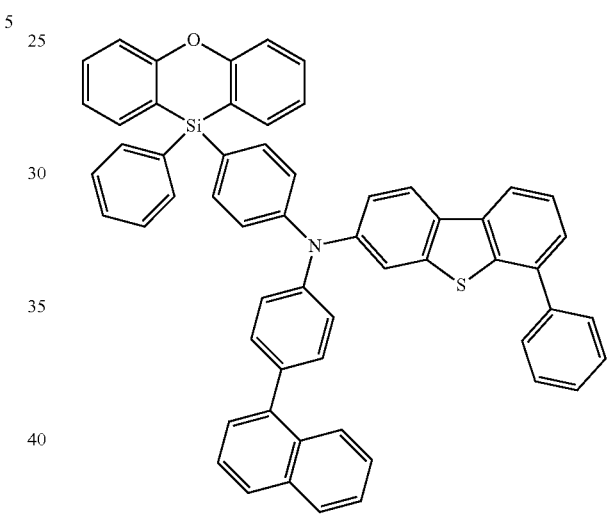
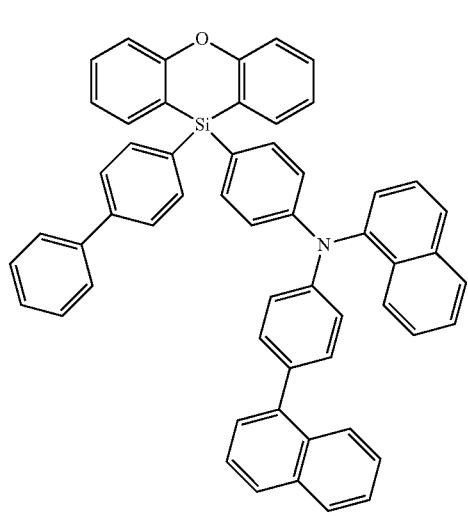
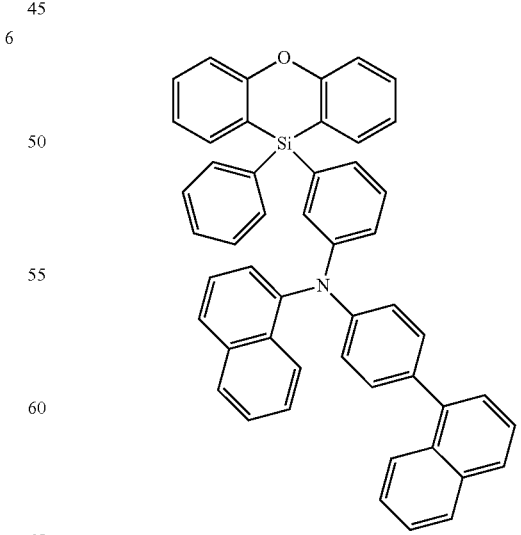

71
-continued
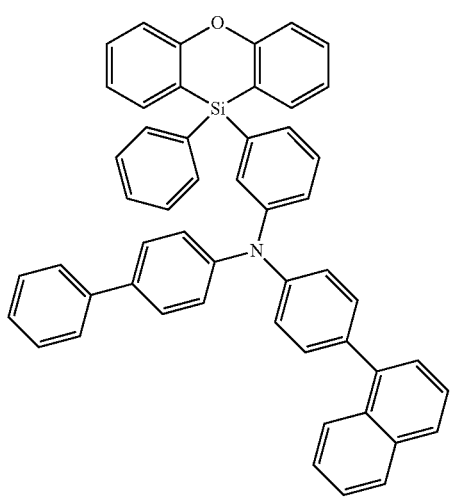
10
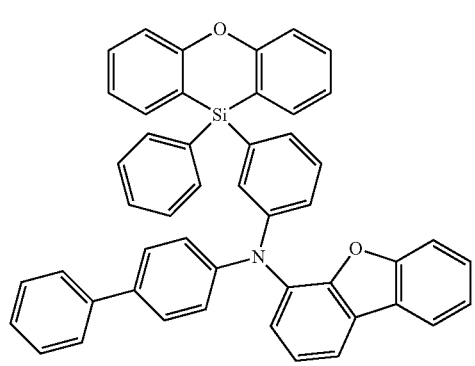
11
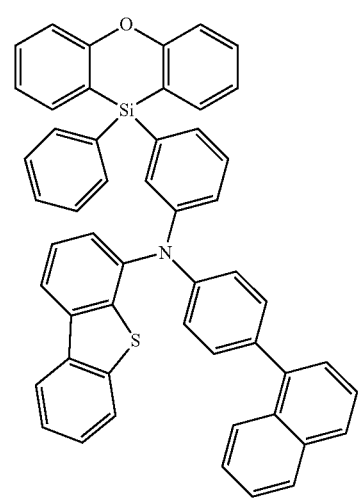
12
72
-continued
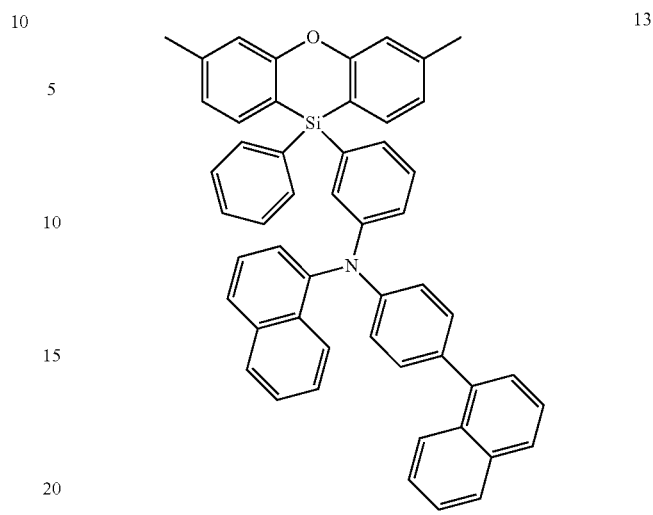
13
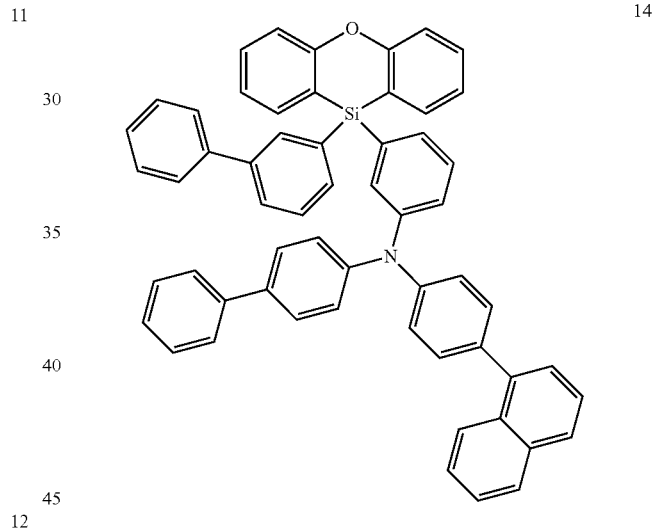
14
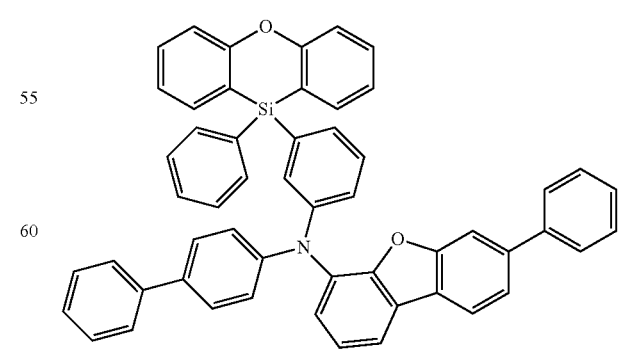
15

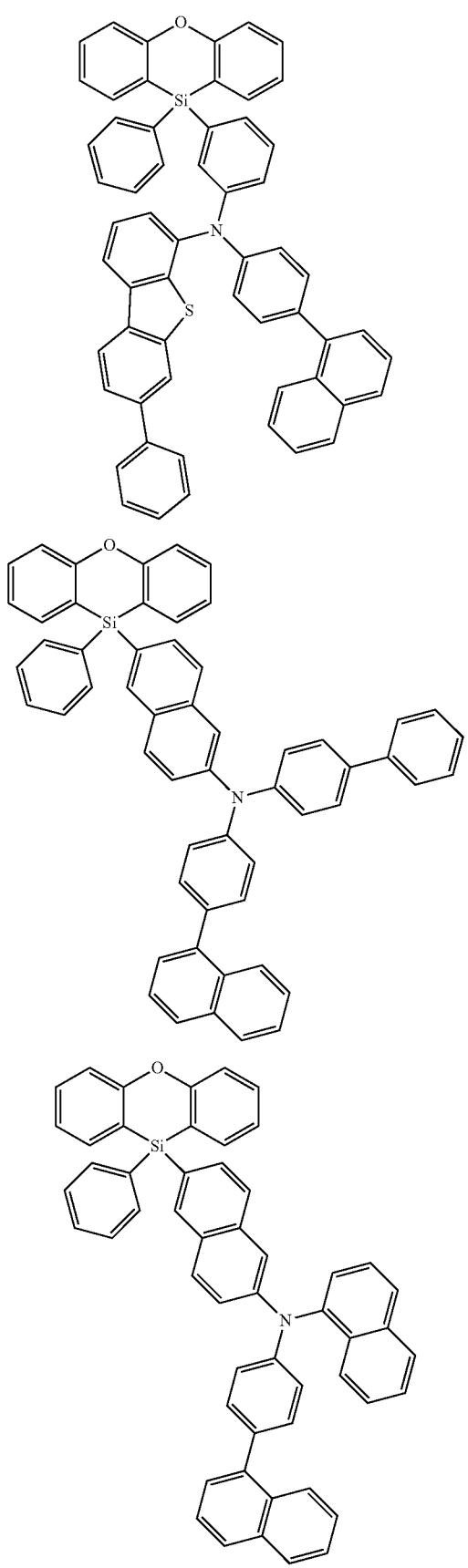
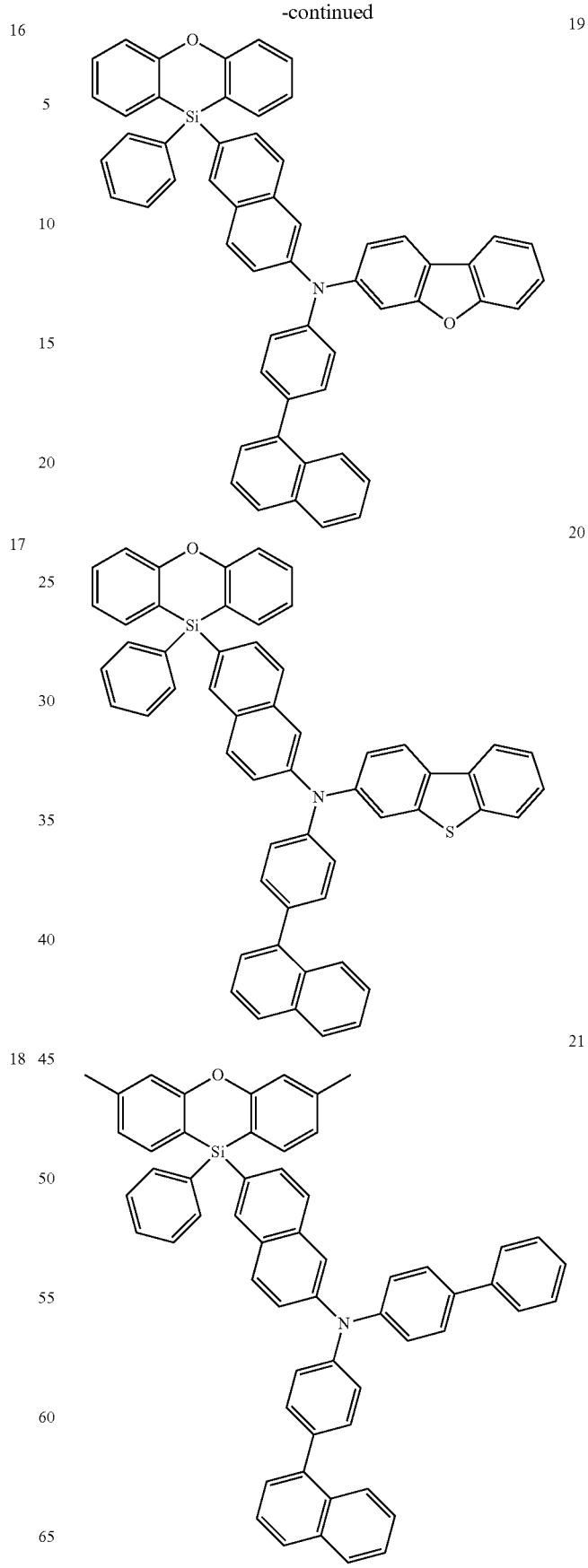

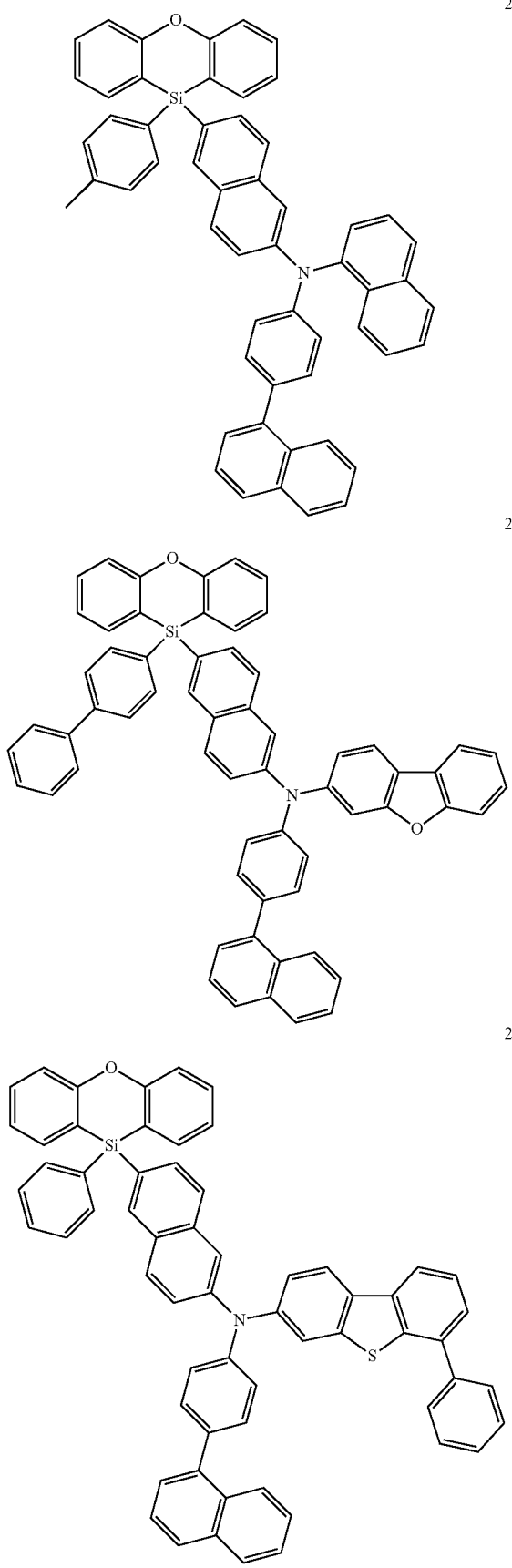
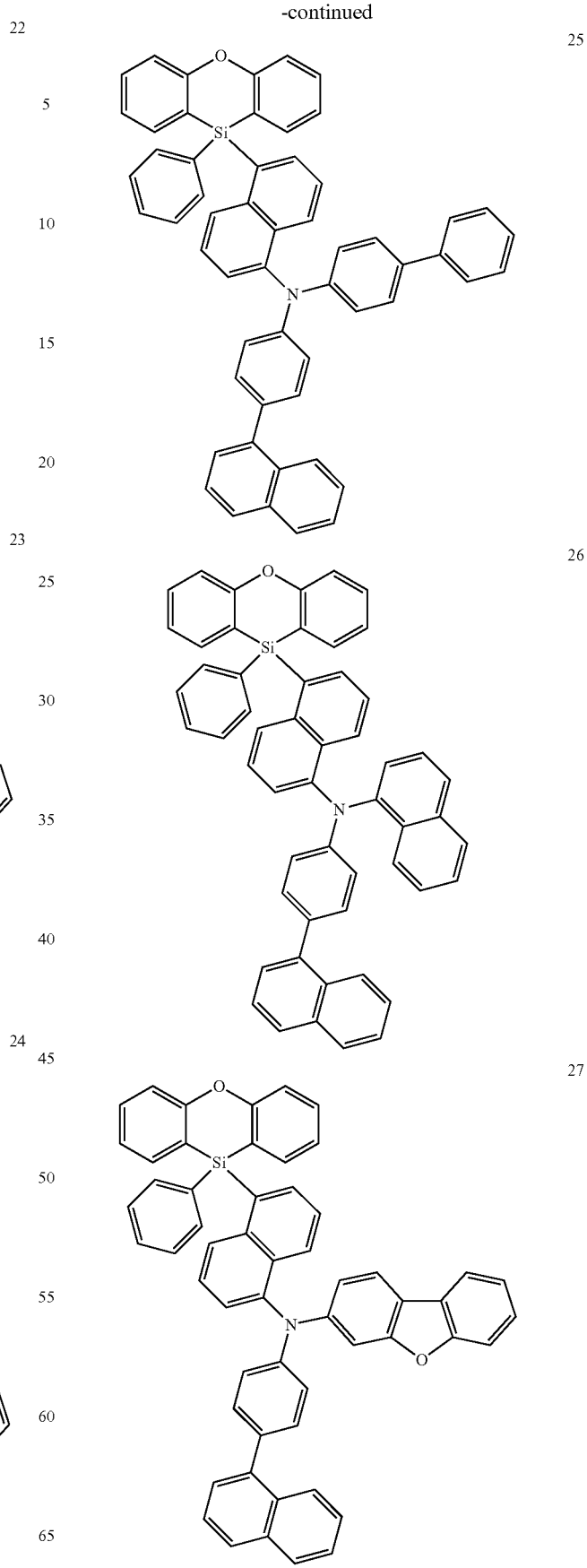

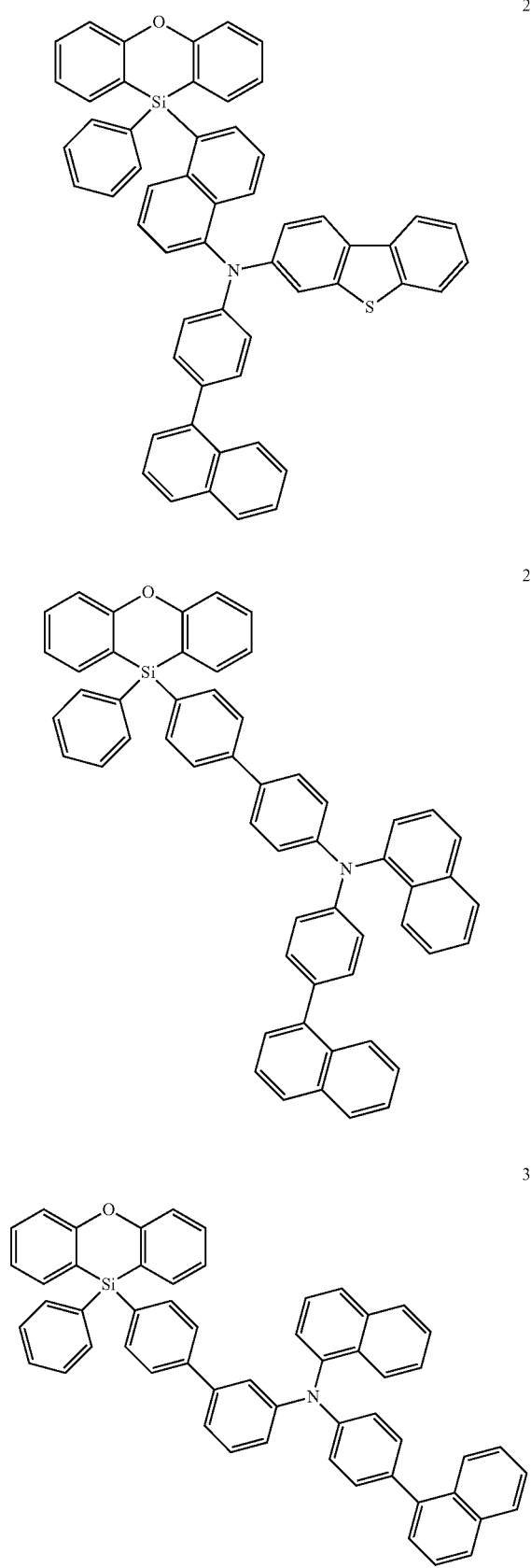
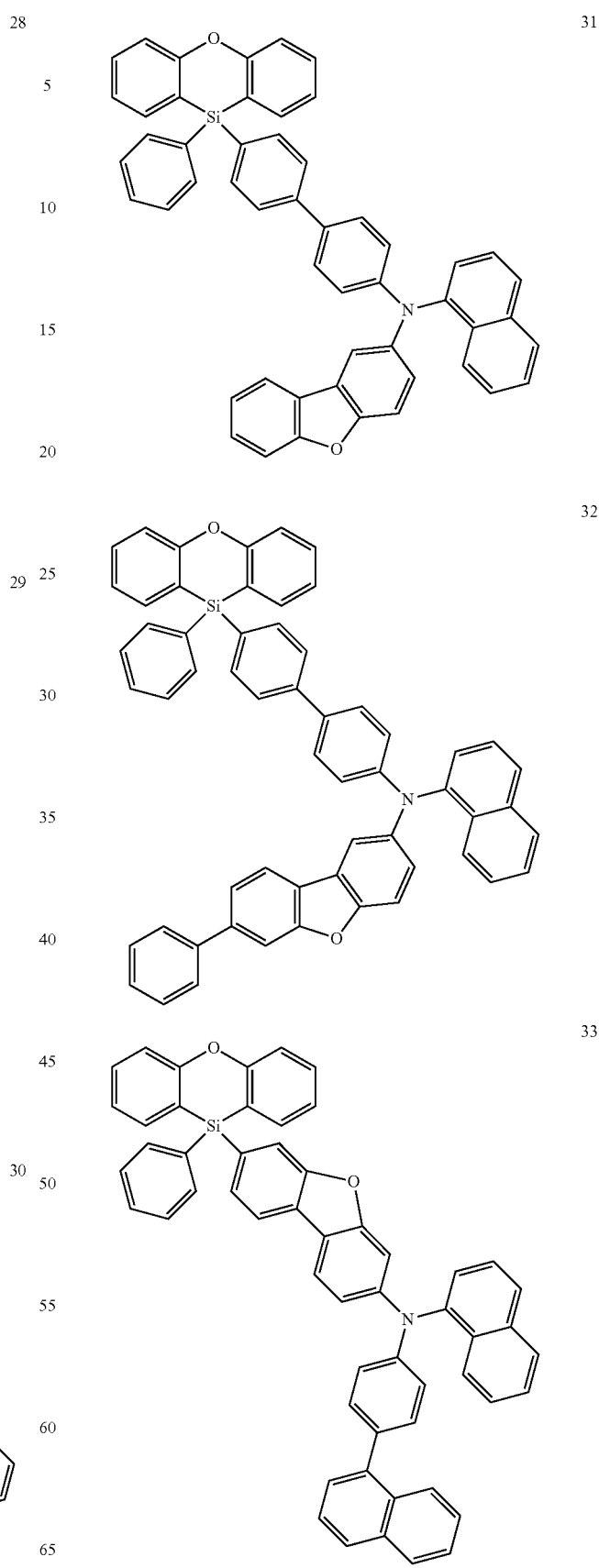

-continued

34

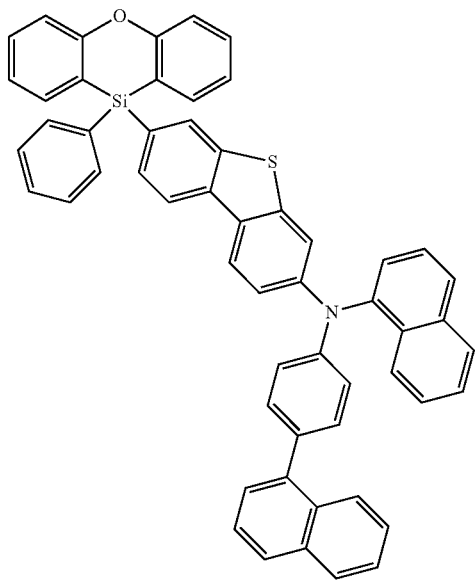

35

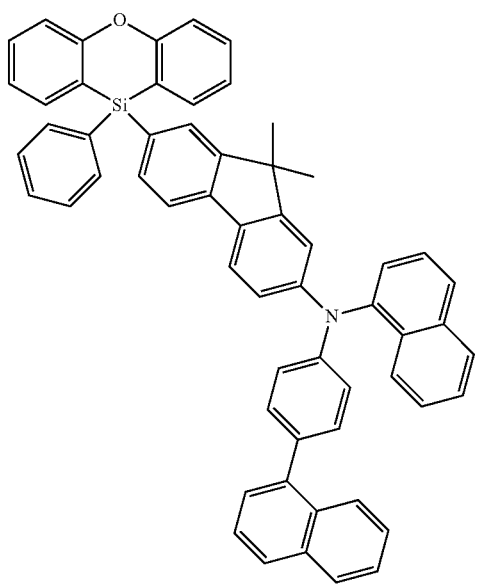

36

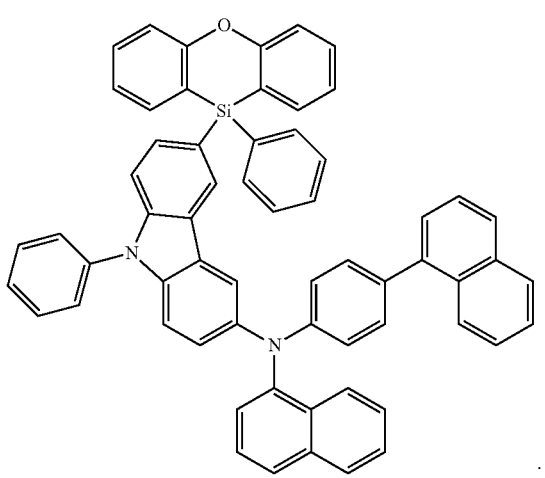

12. An organic electroluminescence device, comprising:
a first electrode;
a hole transport region on the first electrode;
an emission layer on the hole transport region;
an electron transport region on the emission layer; and
a second electrode on the electron transport region,
wherein the hole transport region includes a heterocyclic compound represented by the following Formula 1:

[Formula 1]

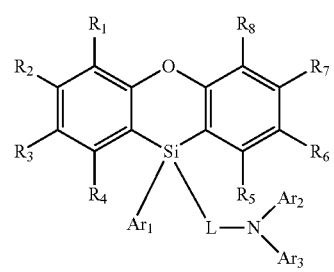

wherein, in Formula 1,
$R_1$ to $R_8$ are each independently a hydrogen atom, a deuterium atom, a halogen atom, a substituted or unsubstituted silyl group, a substituted or unsubstituted alkyl group having 1 to 30 carbon atoms, a substituted or unsubstituted alkenyl group having 2 to 30 carbon atoms, a substituted or unsubstituted alkynyl group having 2 to 30 carbon atoms, a substituted or unsubstituted aryl group having 6 to 30 ring carbon atoms, or a substituted or unsubstituted heteroaryl group having 2 to 30 ring carbon atoms, $R_1$ to $R_8$ being separate or forming a ring by combining adjacent groups with each other, $Ar_1$ to $Ar_3$ are each independently a substituted or unsubstituted aryl group having 6 to 30 ring carbon atoms or a substituted or unsubstituted heteroaryl group having 2 to 30 ring carbon atoms, and L is a direct linkage, a substituted or unsubstituted arylene group having 6 to 30 ring carbon atoms, or a substituted or unsubstituted heteroarylene group having 2 to 30 ring carbon atoms.

13. The organic electroluminescence device as claimed in claim 12, wherein the hole transport region includes:
a hole injection layer on the first electrode; and
a hole transport layer on the hole injection layer, and
the hole transport layer the heterocyclic compound represented by Formula 1.

14. The organic electroluminescence device as claimed in claim 12, wherein $Ar_1$ is a substituted or unsubstituted aryl group having 6 to 30 ring carbon atoms.

15. The organic electroluminescence device as claimed in claim 12, wherein L is a group represented by one of the following Formulae L-1 to L-4:

L-1

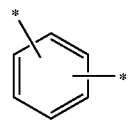

L-2

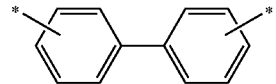

-continued

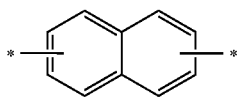
L-3

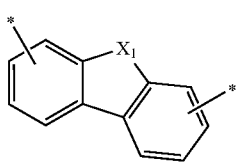
L-4 wherein, in Formula L-4,
X$_1$ is O, S, NR, or CR$_{10}$R$_{11}$, and
R$_9$ to R$_{11}$ are each independently a hydrogen atom, a deuterium atom, a halogen atom, a substituted or unsubstituted alkyl group having 1 to 30 carbon atoms, a substituted or unsubstituted aryl group having 6 to 30 ring carbon atoms, or a substituted or unsubstituted heteroaryl group having 2 to 30 ring carbon atoms.

16. The organic electroluminescence device as claimed in claim 12, wherein at least one of Ar$_2$ or Ar$_3$ is a substituted or unsubstituted aryl group having 6 to 30 ring carbon atoms.

17. The organic electroluminescence device as claimed in claim 12, wherein at least one of Ar$_2$ or Ar$_3$ is a group represented by the following Formula 2:

*-A-B   [Formula 2]

wherein, in Formula 2,
A is a substituted or unsubstituted phenylene group, and
B is a substituted or unsubstituted polycyclic aryl group having 6 to 30 ring carbon atoms.

18. The organic electroluminescence device as claimed in claim 12, wherein Ar$_2$ and Ar$_3$ are different from each other.

19. The organic electroluminescence device as claimed in claim 12, wherein:
one of Ar$_2$ and Ar$_3$ is a substituted or unsubstituted aryl group having 6 to 30 ring carbon atoms, and
the other of Ar$_2$ and Ar$_3$ is a substituted or unsubstituted aryl group having 6 to 30 ring carbon atoms or a group represented by the following Formula 3:

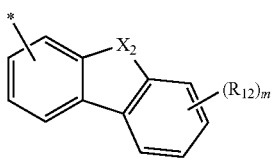
[Formula 3]

wherein, in Formula 3,
X$_2$ is O or S,
m is an integer of 1 to 4, and
R$_{12}$ is a hydrogen atom, a deuterium atom, or a substituted or unsubstituted aryl group having 6 to 30 ring carbon atoms.

20. The organic electroluminescence device as claimed in claim 12, wherein the heterocyclic compound represented by Formula 1 is a compound the following Compound Group 1:

[Compound Group 1]

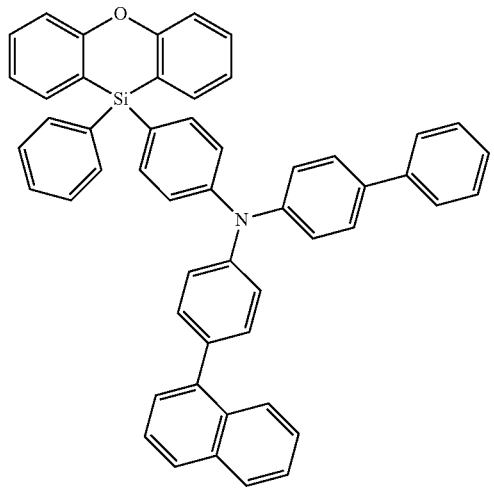
1

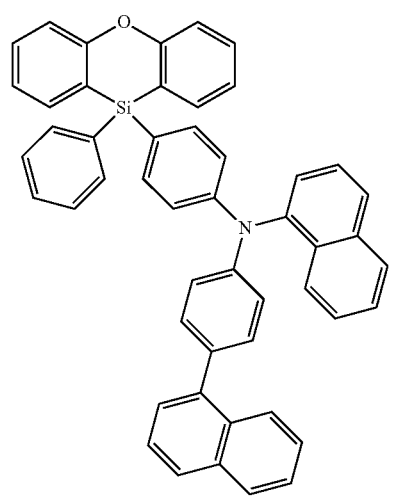
2

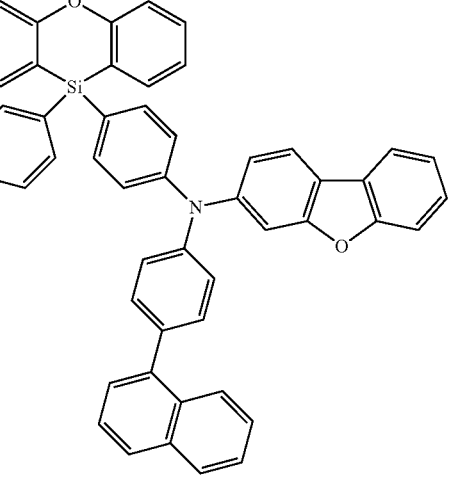
3

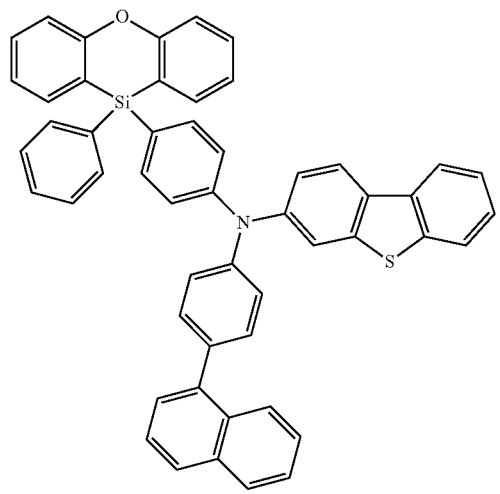
4
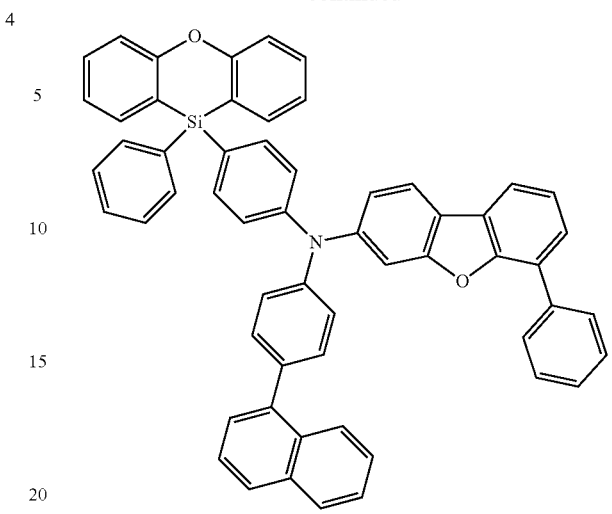
7
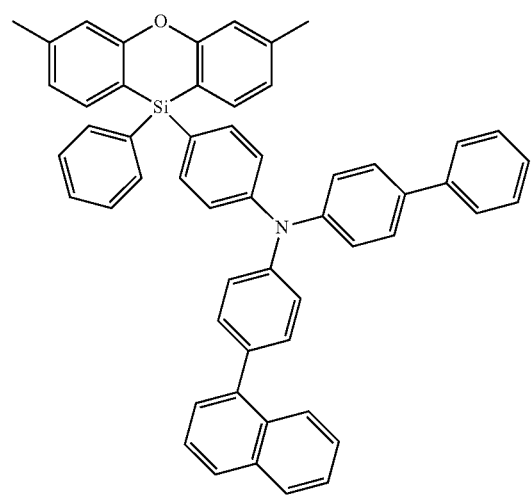
5
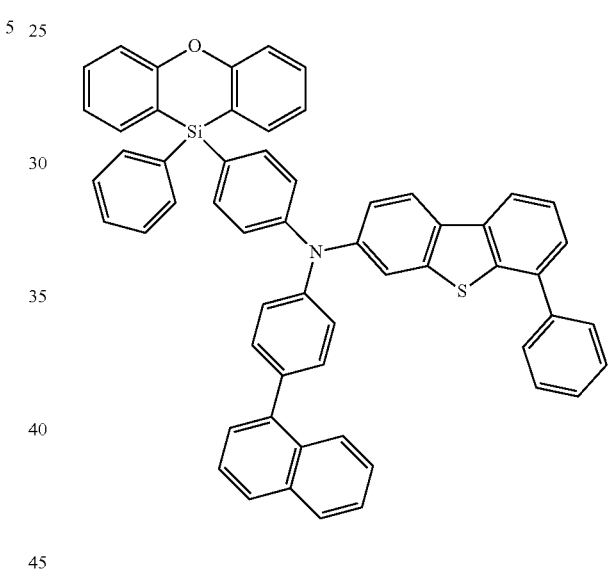
8
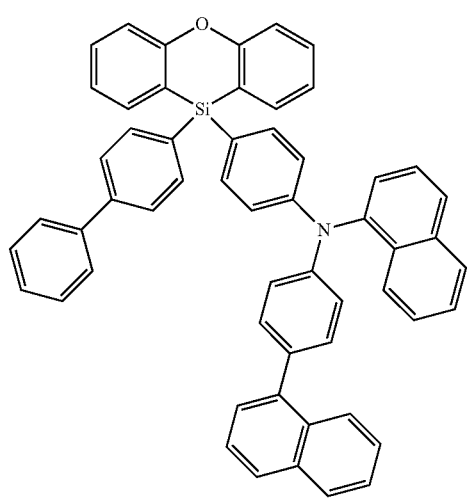
6
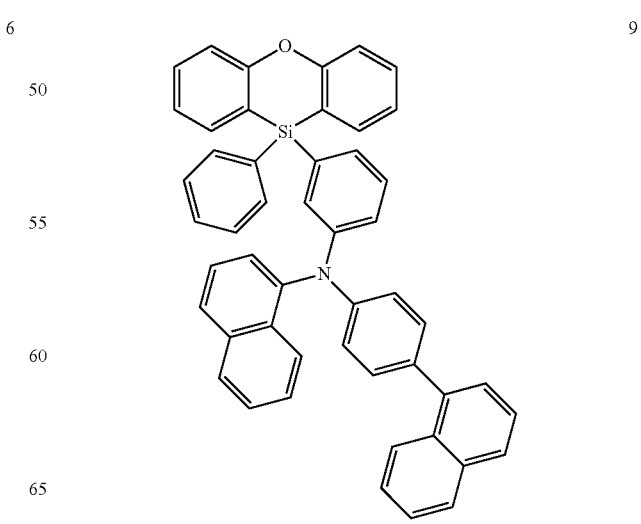
9

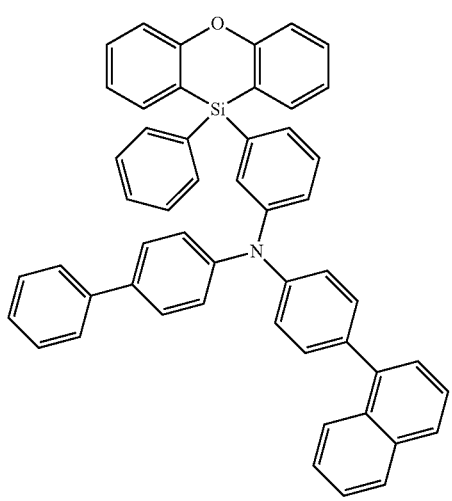
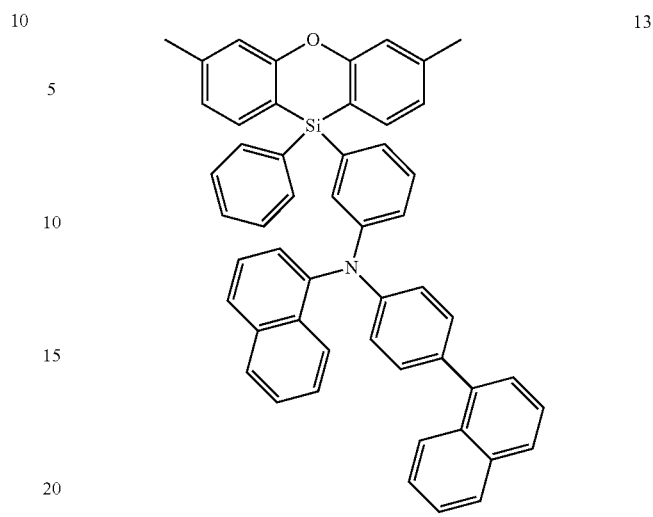

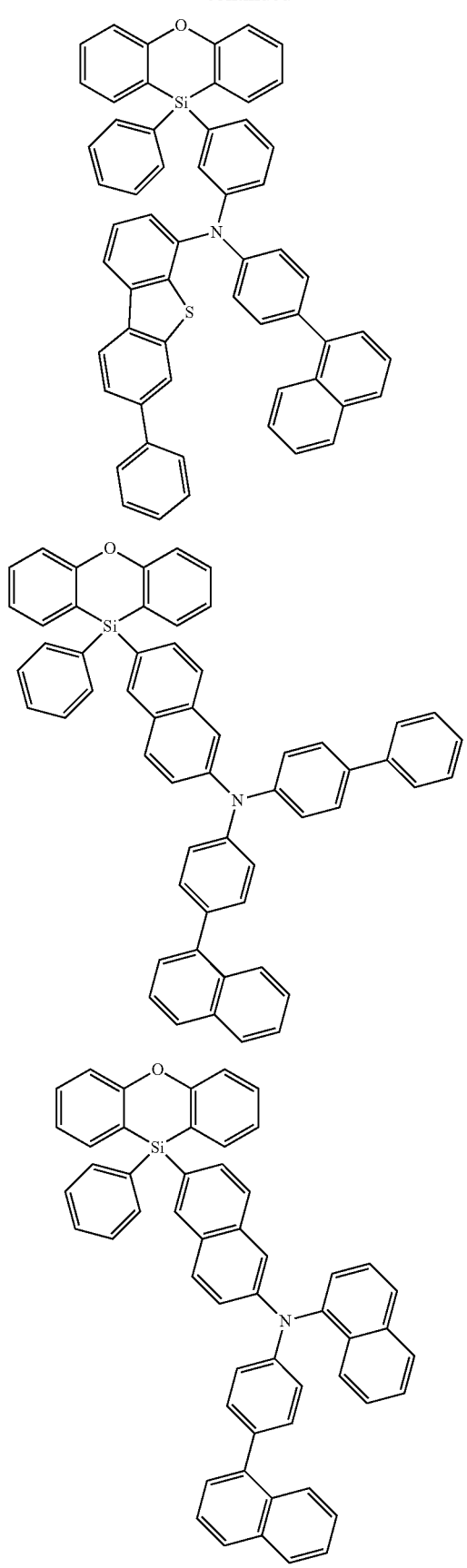
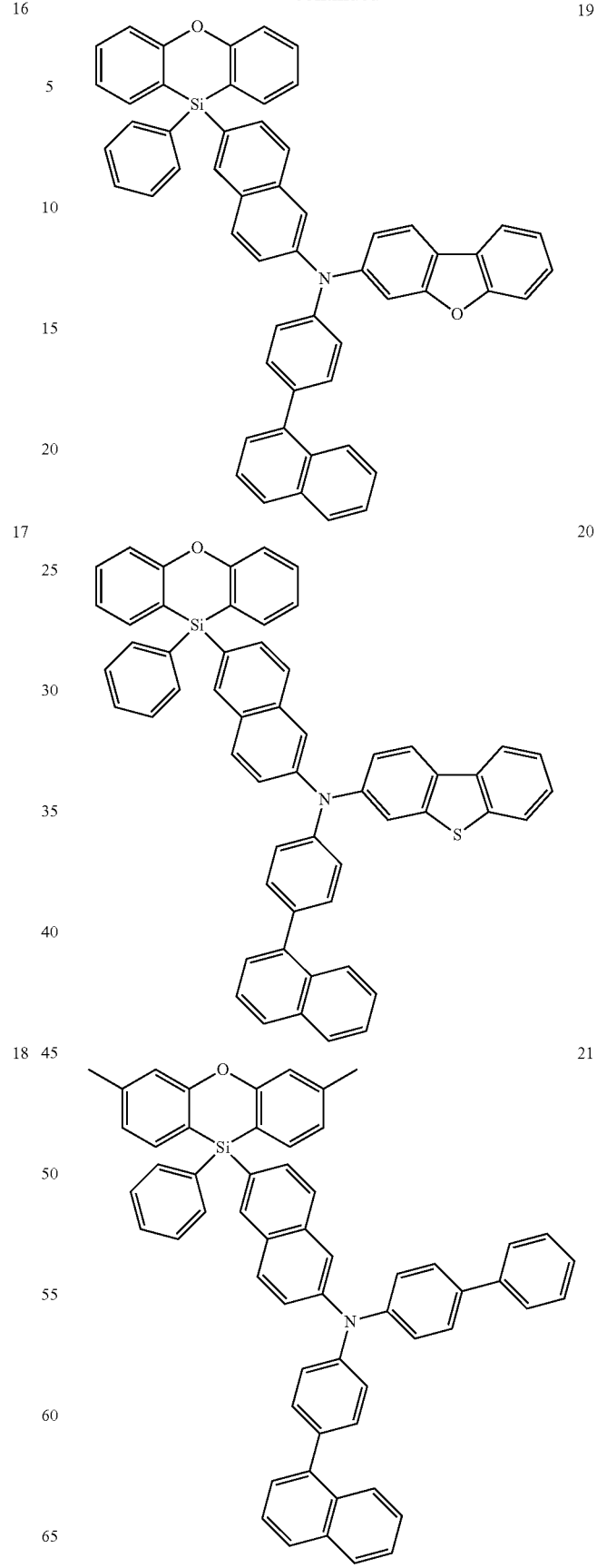

22
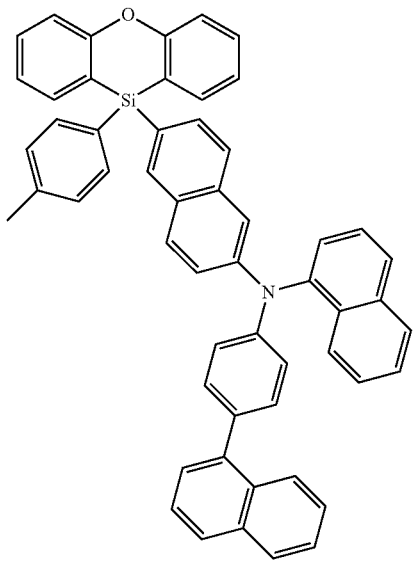
23
25
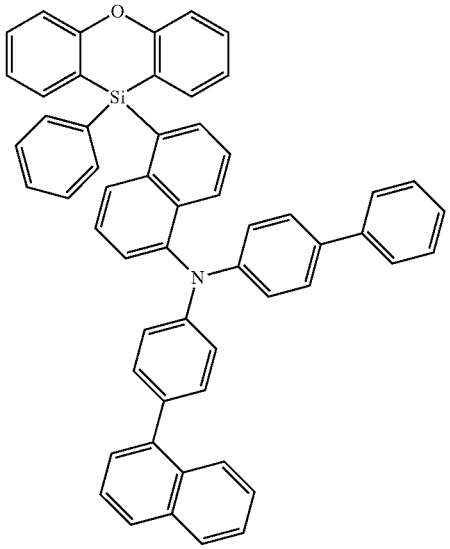
24
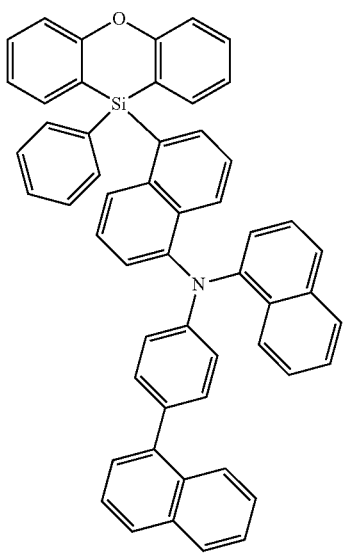
26

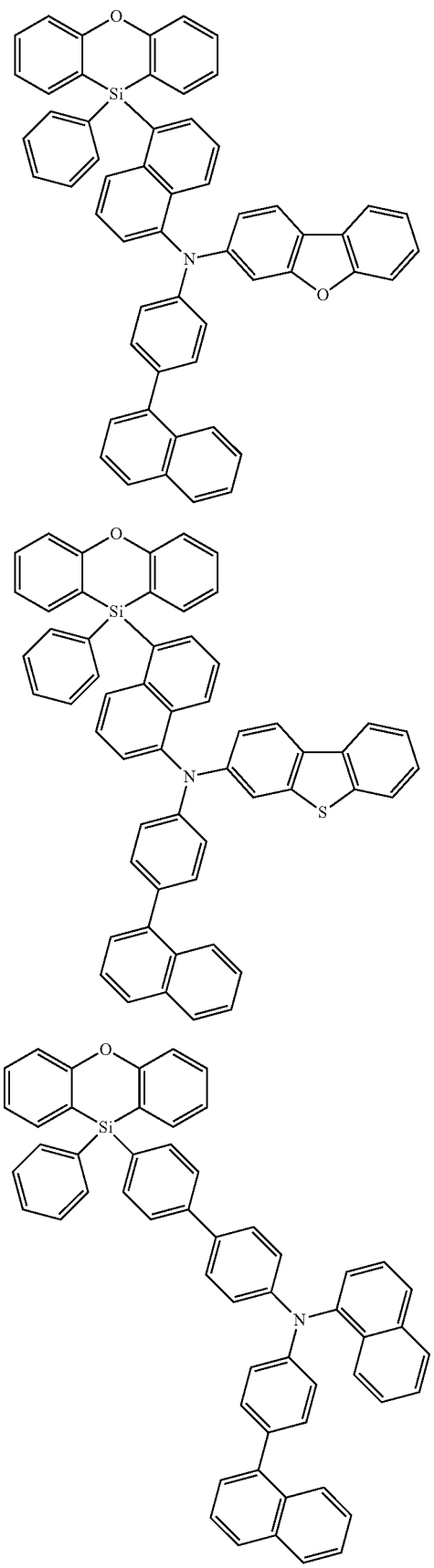
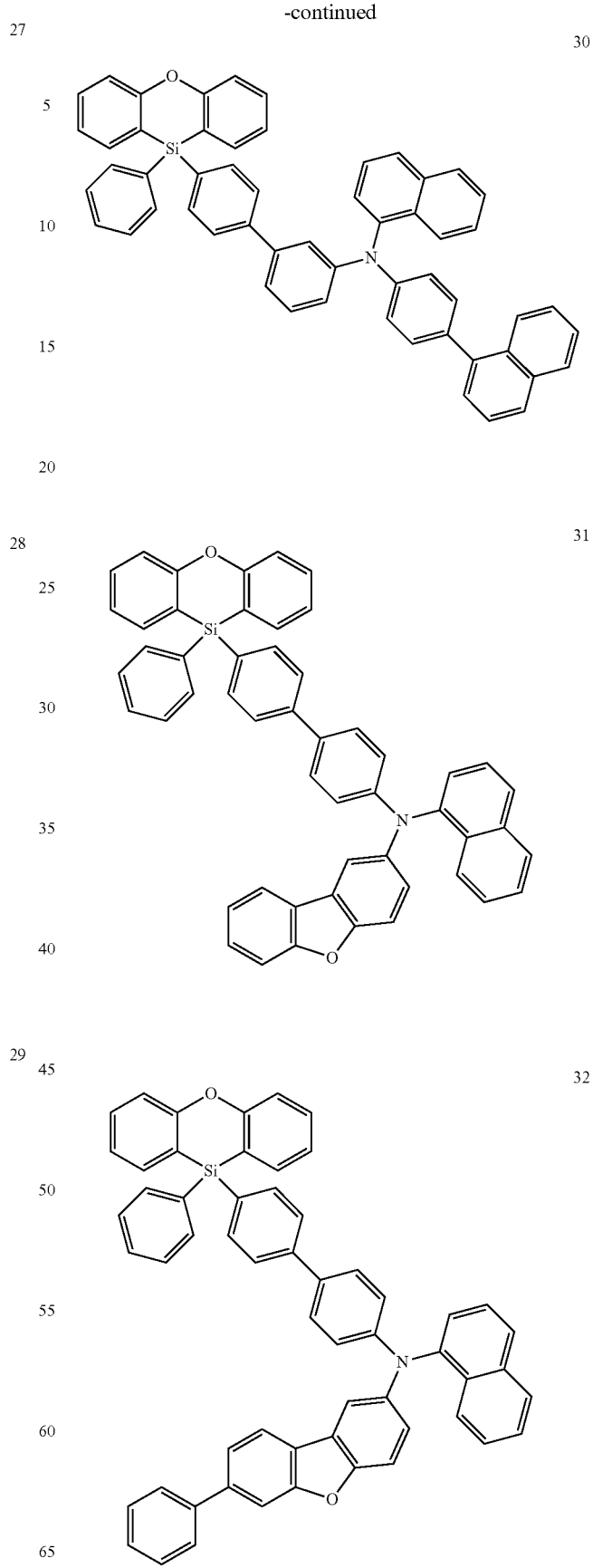

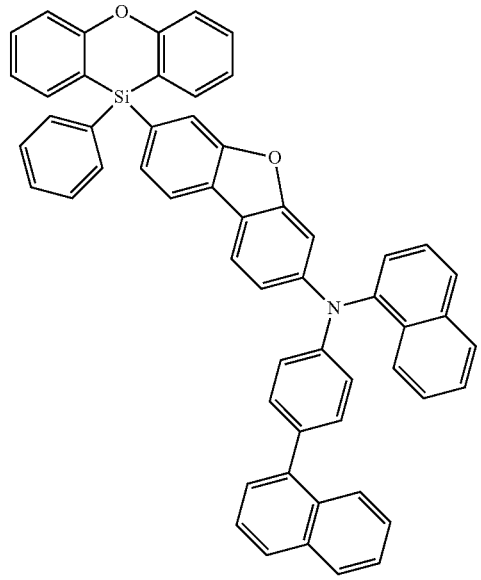
33
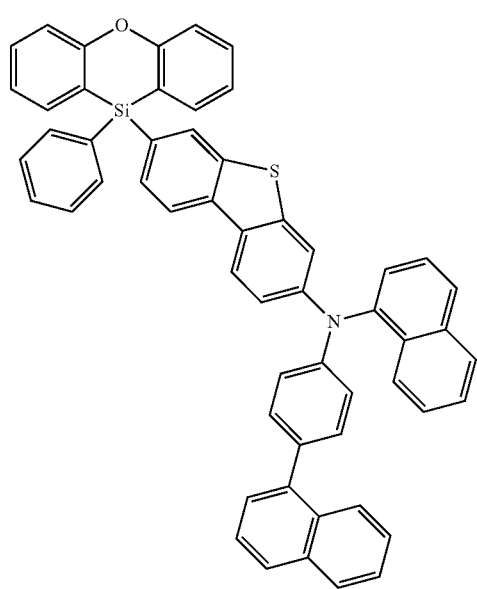
34
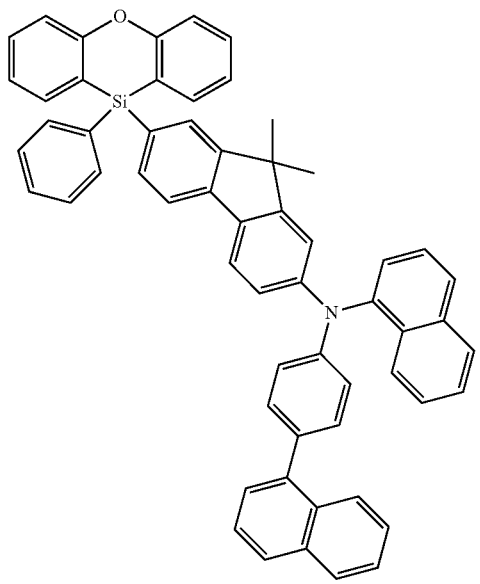
35
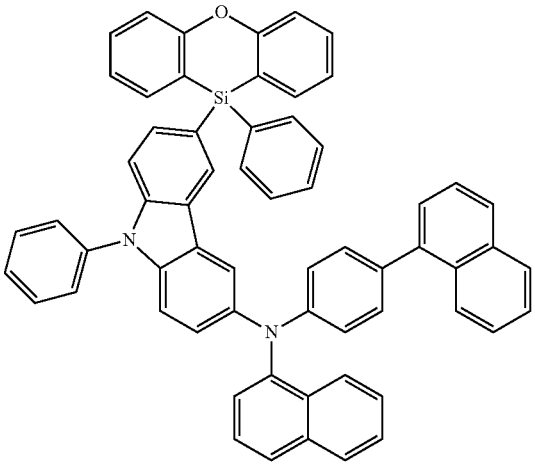
36
* * * * *

UNITED STATES PATENT AND TRADEMARK OFFICE
CERTIFICATE OF CORRECTION

PATENT NO. : 10,550,134 B2  
APPLICATION NO. : 15/801606  
DATED : February 4, 2020  
INVENTOR(S) : Asami Sakamoto et al.

Page 1 of 1

It is certified that error appears in the above-identified patent and that said Letters Patent is hereby corrected as shown below:

In the Claims

Column 67, Line 54, Claim 9    delete "X," and insert -- $X_2$ --

Signed and Sealed this  
Nineteenth Day of January, 2021

Andrei Iancu  
*Director of the United States Patent and Trademark Office*